US012780786B2

(12) United States Patent
Breitenbucher

(10) Patent No.: US 12,780,786 B2
(45) Date of Patent: Nov. 3, 2026

(54) HETEROCYCLIC TRPML1 AGONISTS AND USES THEREOF

(71) Applicant: Libra Therapeutics, Inc., San Diego, CA (US)

(72) Inventor: James Guy Breitenbucher, Escondido, CA (US)

(73) Assignee: LIBRA THERAPEUTICS, INC., Del Mar, CA (US)

(*) Notice: Subject to any disclaimer, the term of this patent is extended or adjusted under 35 U.S.C. 154(b) by 365 days.

(21) Appl. No.: 18/559,288

(22) PCT Filed: May 11, 2022

(86) PCT No.: PCT/US2022/028776
§ 371 (c)(1),
(2) Date: Nov. 6, 2023

(87) PCT Pub. No.: WO2022/240992
PCT Pub. Date: Nov. 17, 2022

(65) Prior Publication Data

US 2024/0254083 A1 Aug. 1, 2024

Related U.S. Application Data

(60) Provisional application No. 63/187,733, filed on May 12, 2021.

(51) Int. Cl.

| | |
|---|---|
| ***C07D 211/46*** | (2006.01) |
| ***A61K 31/395*** | (2006.01) |
| ***A61K 31/45*** | (2006.01) |
| ***A61K 31/4545*** | (2006.01) |
| ***A61K 31/495*** | (2006.01) |
| ***A61K 31/5375*** | (2006.01) |
| ***C07D 241/28*** | (2006.01) |
| ***C07D 265/30*** | (2006.01) |
| ***C07D 401/12*** | (2006.01) |

(52) U.S. Cl.
CPC ............ *C07D 211/46* (2013.01); *A61K 31/45* (2013.01); *A61K 31/4545* (2013.01); *A61K 31/495* (2013.01); *A61K 31/5375* (2013.01); *A61K 31/5545* (2017.08); *C07D 241/28* (2013.01); *C07D 265/30* (2013.01); *C07D 401/12* (2013.01)

(58) Field of Classification Search
CPC ..................................................... C07D 211/46
See application file for complete search history.

(56) References Cited

FOREIGN PATENT DOCUMENTS

| | | | |
|---|---|---|---|
| WO | WO-9824771 | A1 | 6/1998 |
| WO | WO-03045393 | A1 | 6/2003 |
| WO | WO-2004089905 | A1 | 10/2004 |
| WO | WO-2005115146 | A1 | 12/2005 |
| WO | WO-2006111560 | A2 | 10/2006 |
| WO | WO-2007123516 | A1 | 11/2007 |
| WO | WO-2012117000 | A1 | 9/2012 |
| WO | WO-2018005713 | A1 | 1/2018 |
| WO | WO-2018183145 | A1 | 10/2018 |
| WO | WO-2019063996 | A1 | 4/2019 |
| WO | WO-2019201283 | A1 | 10/2019 |
| WO | WO-2021041866 | A1 | 3/2021 |
| WO | WO-2021094974 | A1 | 5/2021 |
| WO | WO-2021127337 | A1 | 6/2021 |
| WO | WO-2022150461 | A1 | 7/2022 |
| WO | WO-2022240992 | A1 | 11/2022 |

OTHER PUBLICATIONS

American Chemical Society. Chemical Abstract Service. RN 2654028-09-6. Entered into STN: Jul. 13, 2021. (Year: 2021).*

Chen et al. A small molecule restores function to TRPML1 mutant isoforms responsible for mucolipidosis type IV. Nat Commun 5:4681 (2014).

PCT/US2022/028776 International Search Report and Written Opinion dated Aug. 3, 2022.

Schwickert et al. Synthesis, X-ray Structure Determination, and Comprehensive Photochemical Characterization of (Trifluoromethyl)diazirine-Containing TRPML1 Ligands. J Org Chem 86(9):6169-6183 (2021).

Yu et al. Small-molecule activation of lysosomal TRP channels ameliorates Duchenne muscular dystrophy in mouse models. Sci Adv 6(6):eaaz2736 (2020).

* cited by examiner

*Primary Examiner* — John S Kenyon
(74) *Attorney, Agent, or Firm* — WILSON SONSINI GOODRICH & ROSATI

(57) ABSTRACT

Described herein are oxazole TRPML1 agonists and pharmaceutical compositions comprising said agonists. The subject compounds and compositions are useful for the treatment of TRPML1-mediated disorders or diseases.

20 Claims, No Drawings

HETEROCYCLIC TRPML1 AGONISTS AND USES THEREOF

CROSS-REFERENCE

This patent application is a national stage entry of PCT/US2022/028776, filed on May 11, 2022, which claims the benefit of U.S. Provisional Application No. 63/187,733, filed May 12, 2021; which are hereby incorporated by reference in their entirety.

BACKGROUND OF THE INVENTION

TRPML1, also named Mucolipin-1, is a ligand-gated cation channel expressed mostly in intracellular organelles like the late endosome and lysosome of many mammalian cells. This channel is member of the large family of Transient receptor potential (TRP) channels and has, with TRPML2 and TRPML3, two close analogues. Loss-of-function mutations in the gene encoding for TRPML1, the 12,000 base pair gene MCOLN-1 located in human chromosome 19p13, are the direct cause of Type IV mucolipidosis (MLIV), an autosomal recessive lysosomal storage disease.

At the molecular level, TRPML1 is a Ca2+-permeable, non-selective cation channel formed of four six-transmembrane spanning proteins each of 580 amino acids. The channel opens upon binding of its endogenous ligand phosphatidylinositol-3,5-bisphosphate (PtdIns(3,5)P2)) to its pore region. Channel activity is modulated by pH and PtdIns(4,5)P2 levels. TRPML1 is an inwardly rectifying channel permeable for different mono- and divalent cations, including Na+, K+, Ca2+ and Fe2+. Its N-terminal AP1 sequence targets the channel to the lysosome while a C-terminal AP2 sequence is responsible for intracellular trafficking and internalization. In addition, TRPML1 has four putative N-linked glycosylation sites in its luminal loop between TM1 and 2. It is reported that TRPML channels can be formed as homo-tetramers (e.g. TRPML1, TRPML2, TRPML3) but also in some cases as hetero-tetramers where one channel is composed of different members of the TRPML family.

TRPML1 is found in all mammalian tissues with highest expression levels in brain, spleen, liver, kidney and heart. Expression is found in many cell types, including neurons, myeloid cells, macrophages, microglia, podocytes and muscle cells. TRPML1 is involved in function of late endosome/lysosomes (LELs), more specifically in protein trafficking and lysis as well as autophagy.

Lysosomes are organelles filled with hydrolytic enzymes, characterized by low luminal pH of about 5, a high luminal Ca2+ concentration of about 0.5 mM and a membrane polarization of about +60 mV.

TRPML1 in LELs is reported to be responsible for the formation of transport vesicles and required for the reformation of lysosomes from LEL hybrid organelles and autolysosomes, mostly due to its Ca2+ permeability. It seems also important for iron release from the lysosome after degradation of iron-binding proteins like cytochrome C. In addition, TRPML1 is reported to regulate autophagy, probably in an mTOR-independent manner, by promoting TFEB translocation to the nucleus via calcineurin activation.

SUMMARY OF THE INVENTION

In MLIV, the lack of functional TRPML1 leads to severe intellectual disability, motor deficits, retinal degeneration and systemic symptoms leading to a strongly reduced life expectancy. Cells from MLIV patients show increased autophagosomes, accumulation of lysofuscin and lipid accumulation in the lysosomes.

Failure of TRPML1-dependent autophagosome-lysosome fusion is also thought to impair clearance of apoptotic neurons by macrophages and microglia cells. Experimental results suggest involvement of TRPML1 in neurodegenerative diseases like Alzheimer's and amyotrophic lateral sclerosis (ALS). For example, Alzheimer's disease related loss-of-function mutations in presenilin 1 lead to dysregulation of lysosomal Ca2+ homeostasis via TRPML1 modulation. On the other side, over-expression of TRPML1 in rodent Alzheimer's models reduced neuronal apoptosis and rescued memory impairments. Pharmacological activation of TRPML1 showed similar effects, clearing accumulated sphingolipids and Aβ peptides from lysosomes. In another study TRPML1 activation was sufficient to upregulate lysosomal exocytosis, rescue defective α-syn secretion and prevent α-syn accumulation in iPSC-derived dopaminergic neurons from patients expressing mutant PARK9. Similarly, TRPML1 activation rescued motor neurons from death and ER stress induced by the cycad neurotoxin beta-methyl-amino-L-alanine, L-BMAA as a model for ALS.

Therefore, it is desired to develop TRPML1 modulators to rescue impaired lysosomal function and cellular autophagy in neurodegenerative diseases.

WO2018005713, WO20210411866, and Nature Communications, 2014 (DOI: 10.1038/ncomms5681) describe TRPML1 agonist molecules. Unfortunately, despite widespread interest for several years across the pharmaceutical industry, currently described small molecule TRPML1 agonists are not optimized for functional activity and drug like properties. Consequently, there is still an unmet need for compounds which can efficiently stimulate TRPML1 and that can be delivered to the different target organs which are sites of any TRPML1-mediated pathology.

Disclosed herein is a compound of Formula (I), or a pharmaceutically acceptable salt, solvate, or stereoisomer thereof:

Formula (I)

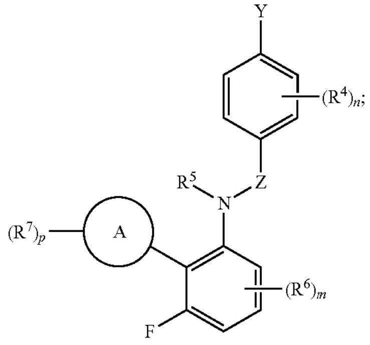

wherein:

Y is $C_1$-$C_6$haloalkyl, $OC_1$-$C_6$haloalkyl, —S(═O)$_2$NR$^1$R$^2$, or —S(═O)$_2$R$^3$;

R$^1$ and R$^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or R$^1$ and R$^2$ are taken together to form a heterocycloalkyl optionally substituted with deuterium, halogen, —CN, —OH, —OR$^a$, —NR$^c$R$^d$, —C(═O)R$^a$, —C(═O)

$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^4$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —C(=O)— or —S(=O)$_2$—;

$R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-3;

Ring A is heterocycloalkyl;

each $R^7$ is independently deuterium, halogen, —CN, —$NO_2$, —OH, —$OR^{10}$, —OC(=O)$R^{10}$, —OC(=O)$OR^{11}$, —OC(=O)$NR^{12}R^{13}$, —SH, —$SR^{10}$, —S(=O)$R^{10}$, —S(=O)$_2R^{10}$, —S(=O)$_2NR^{12}R^{13}$, —$NR^{12}R^{13}$, —$NR^{11}$C(=O)$NR^{12}R^{13}$, —$NR^{11}$C(=O)$R^{10}$, —$NR^{11}$C(=O)$OR^{11}$, —$NR^{11}$S(=O)$_2R^{10}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{7a}$;

each $R^{7a}$ is independently deuterium, halogen, —CN, —$NO_2$, —OH, —$OR^a$, —OC(=O)$R^a$, —OC(=O)$OR^b$, —OC(=O)$NR^cR^d$, —$NR^cR^d$, —$NR^b$C(=O)$NR^cR^d$, —$NR^b$C(=O)$R^a$, —$NR^b$C(=O)$OR^b$, —$NR^b$S(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{7a}$ on the same atom are taken together to form an oxo;

p is 1-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; and each $R^{12}$ and $R^{13}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or $R^{12}$ and $R^{13}$ are taken together with the atom to which they are attached to form a heterocycloalkyl optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Disclosed herein is a compound of Formula (II), or a pharmaceutically acceptable salt, solvate, or stereoisomer thereof:

Formula (II)

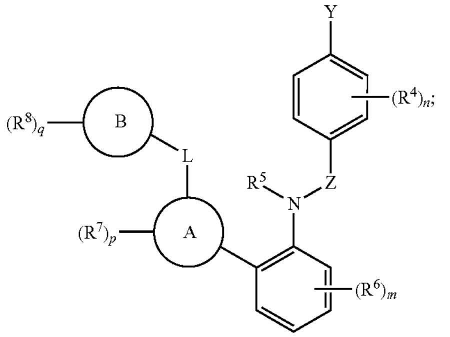

wherein:

Y is $C_1$-$C_6$haloalkyl, $OC_1$-$C_6$haloalkyl, —$S(=O)_2NR^1R^2$, or —$S(=O)_2R^3$;

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^1$ and $R^2$ are taken together to form a heterocycloalkyl optionally substituted with deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^4$ is independently deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —$C(=O)$— or —$S(=O)_2$—;

$R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 1-4;

Ring A is heterocycloalkyl;

each $R^7$ is independently deuterium, halogen, —CN, —$NO_2$, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

p is 0-4;

L is absent or —O—;

Ring B is cycloalkyl, heterocycloalkyl, aryl, or heteroaryl;

each $R^8$ is independently deuterium, halogen, —CN, —$NO_2$, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

q is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Disclosed herein is a compound of Formula (III), or a pharmaceutically acceptable salt, solvate, or stereoisomer thereof:

Formula (III)

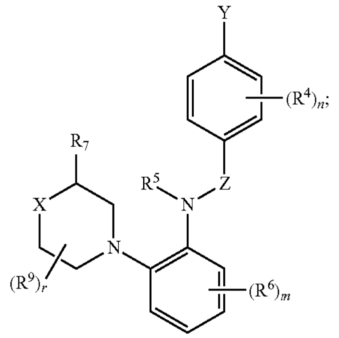

wherein:

Y is —$S(=O)_2NR^1R^2$, —$S(=O)_2R^3$, halogen, $C_1$-$C_6$alkyl, $C_1$-$C_6$haloalkyl, $C_1$-$C_6$deuteroalkyl, $OC_1$-$C_6$alkyl, $OC_1$-$C_6$haloalkyl, or $OC_1$-$C_6$deuteroalkyl;

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^1$ and $R^2$ are taken together to form a heterocycloalkyl optionally substituted with deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^4$ is independently deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —$C(=O)$— or —$S(=O)_2$—;

$R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-4;

X is —O—, —S—, —$S(=O)_2$—, —$NR^9$—, or —$C(R^9)_2$—;

$R^7$ is —W—$OR^{10}$, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, heterocycloalkyl, $C_1$-$C_6$alkyl(cycloalkyl), or $C_1$-$C_6$alkyl(heterocycloalkyl);

W is absent or $C_1$-$C_3$alkylene;

$R^{10}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^9$ is independently hydrogen, deuterium, halogen, —CN, —$NO_2$, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

r is 0-6;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Disclosed herein is a compound of Formula (IV), or a pharmaceutically acceptable salt, solvate, or stereoisomer thereof:

Formula (IV)

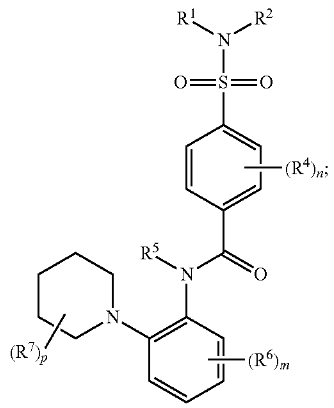

wherein:

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^1$ and $R^2$ are taken together to form a heterocycloalkyl optionally substituted with deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^4$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

$R^5$ is $C_2$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-4;

each $R^7$ is independently deuterium, halogen, —CN, —$NO_2$, —OH, —$OR^{10}$, —OC(=O)$R^{10}$, —OC(=O)$OR^{11}$, —OC(=O)$NR^{12}R^{13}$, —SH, —$SR^{10}$, —S(=O)$R^{10}$, —S(=O)$_2R^{10}$, —S(=O)$_2NR^{12}R^{13}$, —$NR^{12}R^{13}$, —$NR^{11}$C(=O)$NR^{12}R^{13}$, —$NR^{11}$C(=O)$R^{10}$, —$NR^{11}$C(=O)$OR^{11}$, —$NR^{11}$S(=O)$_2R^{10}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{7a}$;

each $R^{7a}$ is independently deuterium, halogen, —CN, —$NO_2$, —OH, —$OR^a$, —OC(=O)$R^a$, —OC(=O)$OR^b$, —OC(=O)$NR^cR^d$, —$NR^cR^d$, —$NR^b$C(=O)$NR^cR^d$, —$NR^b$C(=O)$R^a$, —$NR^b$C(=O)$OR^b$, —$NR^b$S(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{7a}$ on the same atom are taken together to form an oxo;

p is 0-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; and each $R^{12}$ and $R^{13}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or $R^{12}$ and $R^{13}$ are taken together with the atom to which they are attached to form a heterocycloalkyl optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Also disclosed herein is a pharmaceutical composition comprising a compound disclosed herein, or a pharmaceutically acceptable salt, solvate, or stereoisomer thereof, and a pharmaceutically acceptable excipient.

Also disclosed herein is a method of treating a TRPML1-mediated disorder or disease in a subject in need thereof, the method comprising administering a compound disclosed herein, or a pharmaceutically acceptable salt, solvate, or stereoisomer thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —$NH_2$, or —$NO_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —$NH_2$, or —$NO_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —$NH_2$, or —$NO_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —$NH_2$, or —$NO_2$. In some embodiments, the alkylene is optionally substituted with halogen, —CN, —OH, or —OMe. In some embodiments, the alkylene is optionally substituted with halogen.

"Alkoxy" refers to a radical of the formula —$OR^a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —$NH_2$, or —$NO_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —$CF_3$, —OH, —OMe, —$NH_2$, or —$NO_2$. In some embodiments, the aryl is optionally substituted with halogen, methyl, ethyl, —CN, —$CF_3$, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms ($C_3$-$C_{15}$ cycloalkyl or $C_3$-$C_{15}$ cycloalkenyl), from three to ten carbon atoms ($C_3$-$C_{10}$ cycloalkyl or $C_3$-$C_{10}$ cycloalkenyl), from three to eight carbon atoms ($C_3$-$C_8$ cycloalkyl or $C_3$-$C_8$ cycloalkenyl), from three to six carbon atoms ($C_3$-$C_6$ cycloalkyl or $C_3$-$C_6$ cycloalkenyl), from three to five carbon atoms ($C_3$-$C_5$ cycloalkyl or $C_3$-$C_5$ cycloalkenyl), or three to four carbon atoms ($C_3$-$C_4$ cycloalkyl or $C_3$-$C_4$ cycloalkenyl). In some embodiments, the cycloalkyl is a 3- to 10-membered cycloalkyl or a 3- to 10-membered cycloalkenyl. In some embodiments, the cycloalkyl is a 3- to 6-membered cycloalkyl or a 3- to 6-membered cycloalkenyl. In some embodiments, the cycloalkyl is a 5- to 6-membered cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —$CH_2OCH_3$, —$CH_2CH_2OCH_3$, —$CH_2CH_2OCH_2CH_2OCH_3$, —$CH(CH_3)OCH_3$, —$CH_2NHCH_3$, —$CH_2N(CH_3)_2$, —$CH_2CH_2NHCH_3$, or —$CH_2CH_2N(CH_3)_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl or $C_2$-$C_{15}$ heterocycloalkenyl), from two to ten carbon atoms ($C_2$-$C_{10}$ heterocycloalkyl or $C_2$-$C_{10}$ heterocycloalkenyl), from two to eight carbon atoms ($C_2$-$C_8$ heterocycloalkyl or $C_2$-$C_8$ heterocycloalkenyl), from two to seven carbon atoms ($C_2$-$C_7$ heterocycloalkyl or $C_2$-$C_7$ heterocycloalkenyl), from two to six carbon atoms ($C_2$-$C_6$ heterocycloalkyl or $C_2$-$C_7$ heterocycloalkenyl), from two to five carbon atoms ($C_2$-$C_5$ heterocycloalkyl or $C_2$-$C_5$ heterocycloalkenyl), or two to four carbon atoms ($C_2$-$C_4$ heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, $—CF_3$, —OH, —OMe, $—NH_2$, or $—NO_2$. In some embodiments, the heterocycloalkyl is optionally substituted with halogen, methyl, ethyl, —CN, $—CF_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, $—CF_3$, —OH, —OMe, $—NH_2$, or $—NO_2$. In some embodiments, the heteroaryl is optionally substituted with halogen, methyl, ethyl, —CN, $—CF_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., $—CH_2CH_3$), fully substituted (e.g., $—CF_2CF_3$), mono-substituted (e.g., $—CH_2CH_2F$) or substituted at a level anywhere in-between fully substituted and mono-substituted (e.g., $—CH_2CHF_2$, $—CH_2CF_3$, $—CF_2CH_3$, $—CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

"Synergy" or "synergize" refers to an effect of a combination that is greater than additive of the effects of each component alone at the same doses.

As used herein, a "disease or disorder associated with TRPML1" or, alternatively, "a TRPML1-mediated disease or disorder" means any disease or other deleterious condition in which TRPML1, or a mutant thereof, is known or suspected to play a role.

Compounds

Described herein are compounds, or a pharmaceutically acceptable salt, solvate, or stereoisomer thereof useful in the treatment of a TRPML1-mediated disease or disorder.

Disclosed herein is a compound of Formula (I), or a pharmaceutically acceptable salt, solvate, or stereoisomer thereof:

Formula (I)

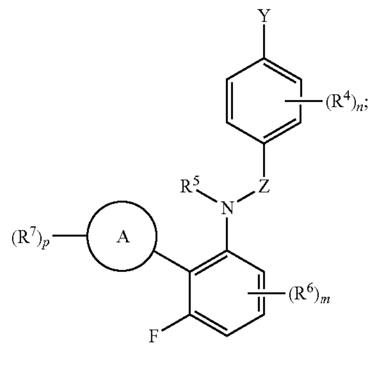

wherein:

Y is $C_1$-$C_6$haloalkyl, —S(═O)$_2$NR$^1$R$^2$, or —S(═O)$_2$R;

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^1$ and $R^2$ are taken together to form a heterocycloalkyl optionally substituted with deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^4$ is independently deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —C(═O)— or —S(═O)$_2$—;

$R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-3;

Ring A is heterocycloalkyl;

each $R^7$ is independently deuterium, halogen, —CN, —NO$_2$, —OH, —OR$^{10}$, —OC(═O)R$^{10}$, —OC(═O)OR$^{11}$, —OC(═O)NR$^{12}$R$^{13}$, —SH, —SR$^{10}$, —S(═O)R$^{10}$, —S(═O)$_2$R$^{10}$, —S(═O)$_2$NR$^{12}$R$^{13}$, —NR$^{12}$R$^{13}$, —NR$^{11}$C(═O)NR$^{12}$R$^{13}$, —NR$^{11}$C(═O)R$^{10}$, —NR$^{11}$C(═O)OR$^{11}$, —NR$^{11}$S(═O)$_2$R$^{10}$, —C(═O)R$^{10}$, —C(═O)OR$^{11}$, —C(═O)NR$^{12}$R$^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{7a}$;

each $R^{7a}$ is independently deuterium, halogen, —CN, —NO$_2$, —OH, —OR$^a$, —OC(═O)R$^a$, —OC(═O)OR$^b$, —OC(═O)NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{7a}$ on the same atom are taken together to form an oxo;

p is 1-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —OR$^a$, —NR$^c$R$^d$, —C(═O)R$^a$, —C(═O)OR, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; and each $R^{12}$ and $R^{13}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or $R^{12}$ and $R^{13}$ are taken together with the atom to which they are attached to form a heterocycloalkyl optionally substituted with one or more deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Also disclosed herein is a compound of Formula (I), or a pharmaceutically acceptable salt, solvate, or stereoisomer thereof:

Formula (I)

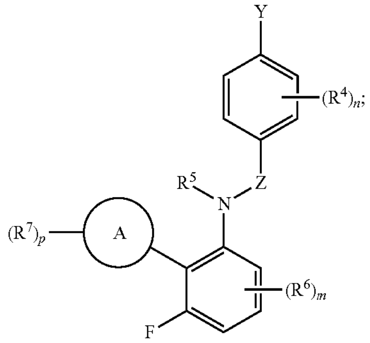

wherein:

Y is $C_1$-$C_6$haloalkyl, $OC_1$-$C_6$haloalkyl, —S(=O)$_2NR^1R^2$, or —S(=O)$_2R^3$;

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^4$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —C(═O)— or —$S(═O)_2$—;

$R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-3;

Ring A is heterocycloalkyl;

each $R^7$ is independently deuterium, halogen, —CN, —$NO_2$, —OH, —$OR^{10}$, —OC(═O)$R^{10}$, —OC(═O)$OR^{11}$, —OC(═O)$NR^{12}R^{13}$, —SH, —$SR^{10}$, —S(═O)$R^{10}$, —$S(═O)_2R^{10}$, —$S(═O)_2NR^{12}R^{13}$, —$NR^{12}R^{13}$, —$NR^{11}$C(═O)$NR^{12}R^{13}$, —$NR^{11}$C(═O)$R^{10}$, —$NR^{11}$C(═O)$OR^{11}$, —$NR^{11}S(═O)_2R^{10}$, —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{7a}$;

each $R^{7a}$ is independently deuterium, halogen, —CN, —$NO_2$, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, or $C_2$-$C_6$alkynyl;

or two $R^{7a}$ on the same atom are taken together to form an oxo;

p is 1-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$;

each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$; and each $R^{12}$ and $R^{13}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$;

or $R^{12}$ and $R^{13}$ are taken together with the atom to which they are attached to form a heterocycloalkyl optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^a$ is independently $C_1$-$C_6$alkyl, $C_1$-$C_6$haloalkyl, or $C_1$-$C_6$deuteroalkyl;

each $R^b$ is independently hydrogen, $C_1$-$C_6$alkyl, $C_1$-$C_6$haloalkyl, or $C_1$-$C_6$deuteroalkyl; and each $R^c$ and $R^d$ are independently hydrogen, $C_1$-$C_6$alkyl, $C_1$-$C_6$haloalkyl, or $C_1$-$C_6$deuteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(═O)$CH_3$, —$S(═O)_2CH_3$, —$S(═O)_2NH_2$, —$S(═O)_2NHCH_3$, —$S(═O)_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (I), Y is $C_1$-$C_6$haloalkyl. In some embodiments of a compound of Formula (I), Y is —$S(═O)_2NR^1R^2$. In some embodiments of a compound of Formula (I), Y is —$S(═O)_2R^3$. In some embodiments of a compound of Formula (I), Y is —$S(═O)_2NR^1R^2$ or —$S(═O)_2R^3$. In some embodiments of a compound of Formula (I), Y is $OC_1$-$C_6$haloalkyl. In some embodiments of a compound of Formula (I), Y is $C_1$-$C_6$haloalkyl or $OC_1$-$C_6$haloalkyl.

In some embodiments of a compound of Formula (I), $R^1$ and $R^2$ are independently hydrogen or $C_1$-$C_6$alkyl. In some embodiments of a compound of Formula (I), $R^1$ and $R^2$ are independently $C_1$-$C_6$alkyl.

In some embodiments of a compound of Formula (I), $R^3$ is $C_1$-$C_6$alkyl.

In some embodiments of a compound of Formula (I), n is 3. In some embodiments of a compound of Formula (I), n is 2. In some embodiments of a compound of Formula (I), n is 1. In some embodiments of a compound of Formula (I), n is 0. In some embodiments of a compound of Formula (I), n is 0 or 1. In some embodiments of a compound of Formula (I), n is 0-2. In some embodiments of a compound of Formula (I), n is 1 or 2.

In some embodiments of a compound of Formula (I), each $R^4$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (I), each $R^4$ is independently deuterium, halogen, $C_1$-$C_6$alkyl, $C_1$-$C_6$haloalkyl, or $C_1$-$C_6$deuteroalkyl. In some embodiments of a compound of Formula (I), each $R^4$ is independently deuterium, halogen, or $C_1$-$C_6$alkyl.

In some embodiments of a compound of Formula (I), Z is —C(═O)—. In some embodiments of a compound of Formula (I), Z is —$S(═O)_2$—.

In some embodiments of a compound of Formula (I), $R^5$ is hydrogen, $C_1$-$C_6$alkyl, $C_1$-$C_6$heteroalkyl, or cycloalkyl. In some embodiments of a compound of Formula (I), $R^5$ is hydrogen or $C_1$-$C_6$alkyl. In some embodiments of a compound of Formula (I), $R^5$ is hydrogen. In some embodiments of a compound of Formula (I), $R^5$ is $C_1$-$C_6$alkyl.

In some embodiments of a compound of Formula (I), m is 3. In some embodiments of a compound of Formula (I), m is 2. In some embodiments of a compound of Formula (I), m is 1. In some embodiments of a compound of Formula (I), m is 0. In some embodiments of a compound of Formula (I), m is 0 or 1. In some embodiments of a compound of Formula (I), m is 0-2. In some embodiments of a compound of Formula (I), m is 1 or 2.

In some embodiments of a compound of Formula (I), each $R^6$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (I), each $R^6$ is independently deuterium, halogen, $C_1$-$C_6$alkyl, $C_1$-$C_6$haloalkyl, or $C_1$-$C_6$deuteroalkyl. In some embodiments of a compound of Formula (I), each $R^6$ is independently deuterium, halogen, or $C_1$-$C_6$alkyl.

In some embodiments of a compound of Formula (I), Ring A is N-linked heterocycloalkyl. In some embodiments of a compound of Formula (I), Ring A is a 5- or 6-membered heterocycloalkyl. In some embodiments of a compound of Formula (I), Ring A is a 5-membered heterocycloalkyl. In some embodiments of a compound of Formula (I), Ring A is a 6-membered heterocycloalkyl. In some embodiments of a compound of Formula (I), Ring A is piperidinyl, morpholinyl, or piperazinyl. In some embodiments of a compound of Formula (I), Ring A is piperidinyl.

In some embodiments of a compound of Formula (I), each $R^7$ is independently deuterium, halogen, —CN, —OH, —$OR^{10}$, —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein the alkyl, cycloalkyl, heterocycloalkyl, aryl, and heteroaryl is optionally and independently substituted with one or more $R^a$. In some embodiments of a compound of Formula (I), each $R^7$ is independently —$OR^{10}$, $C_1$-$C_6$alkyl, $C_1$-$C_6$haloalkyl, $C_1$-$C_6$deuteroalkyl, aryl, or heteroaryl; wherein the alkyl, aryl, and heteroaryl is optionally and independently substituted with one or more $R^{7a}$. In some embodiments of a compound of Formula (I), each $R^7$ is independently —$OR^{10}$ or $C_1$-$C_6$alkyl optionally and independently substituted with one or more $R^{7a}$. In some embodiments of a compound of Formula (I), $R^7$ is —$OR^{10}$. In some embodiments of a compound of Formula (I), each $R^7$ is independently $C_1$-$C_6$alkyl, aryl, or heteroaryl; wherein the alkyl, aryl, and heteroaryl is optionally and independently substituted with one or more $R^{7a}$. In some embodiments of a compound of Formula (I), each $R^7$ is independently $C_1$-$C_6$alkyl or aryl; wherein the alkyl and aryl is optionally and independently substituted with one or more $R^{7a}$. In some embodiments of a compound of Formula (I), each $R^7$ is independently $C_1$-$C_6$alkyl or heteroaryl; wherein the alkyl and heteroaryl is optionally and independently substituted with one or more $R^{7a}$.

In some embodiments of a compound of Formula (I), each $R^{7a}$ is independently deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; or two $R^{7a}$ on the same atom are taken together to form an oxo. In some embodiments of a compound of Formula (I), each $R^{7a}$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl; or two $R^{7a}$ on the same atom are taken together to form an oxo. In some embodiments of a compound of Formula (I), each $R^{7a}$ is independently deuterium, halogen, —OH, —$OR^a$, $C_1$-$C_6$alkyl, $C_1$-$C_6$haloalkyl, or $C_1$-$C_6$deuteroalkyl.

In some embodiments of a compound of Formula (I), p is 3. In some embodiments of a compound of Formula (I), p is 2. In some embodiments of a compound of Formula (I), p is 1. In some embodiments of a compound of Formula (I), p is 1 or 2.

In some embodiments of a compound of Formula (I), each $R^{10}$ is independently aryl or heteroaryl; wherein each aryl and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I), each $R^{10}$ is independently aryl or heteroaryl; wherein each aryl and heteroaryl is independently optionally substituted with one or more deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (I), each $R^{10}$ is independently aryl optionally substituted with one or more deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (I), each $R^{10}$ is independently heteroaryl optionally substituted with one or more deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (I), each $R^{10}$ is independently aryl optionally substituted with one or more deuterium, halogen, $C_1$-$C_6$alkyl, $C_1$-$C_6$haloalkyl, or $C_1$-$C_6$deuteroalkyl. In some embodiments of a compound of Formula (I), each $R^{10}$ is independently heteroaryl optionally substituted with one or more deuterium, halogen, $C_1$-$C_6$alkyl, $C_1$-$C_6$haloalkyl, or $C_1$-$C_6$deuteroalkyl.

In some embodiments of a compound of Formula (I), each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I), each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; wherein each alkyl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl.

In some embodiments of a compound of Formula (I), each $R^{12}$ and $R^{13}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I), each $R^{12}$ and $R^{13}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; wherein each alkyl is independently optionally substituted with one or more deuterium, halogen, —CN, —OH, —OR$^a$, —NR$^c$R$^d$, —C(=O)R$^a$, —C(=O)OR, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl.

Also disclosed herein is a compound of Formula (II), or a pharmaceutically acceptable salt, solvate, or stereoisomer thereof:

Formula (II)

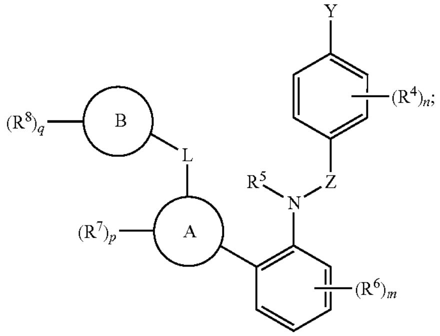

wherein:

- Y is $C_1$-$C_6$haloalkyl, O$C_1$-$C_6$haloalkyl, —S(=O)$_2$NR$^1$R$^2$, or —S(=O)$_2$R$^3$;
- $R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
- or $R^1$ and $R^2$ are taken together to form a heterocycloalkyl optionally substituted with deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
- $R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
- each $R^4$ is independently deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
- n is 0-4;
- Z is —C(=O)— or —S(=O)$_2$—;
- $R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
- each $R^6$ is independently deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
- m is 1-4;
- Ring A is heterocycloalkyl;
- each $R^7$ is independently deuterium, halogen, —CN, —$NO_2$, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
- p is 0-4;
- L is absent or —O—;
- Ring B is cycloalkyl, heterocycloalkyl, aryl, or heteroaryl;
- each $R^8$ is independently deuterium, halogen, —CN, —$NO_2$, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
- q is 0-4;
- each R$^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
- each R$^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and
- each R$^c$ and R$^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Also disclosed herein is a compound of Formula (II), or a pharmaceutically acceptable salt, solvate, or stereoisomer thereof:

Formula (II)

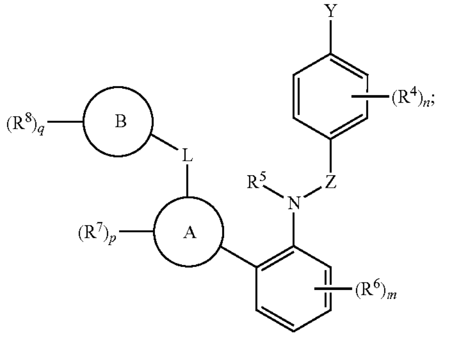

wherein:

Y is $C_1$-$C_6$haloalkyl, O$C_1$-$C_6$haloalkyl, —S(=O)$_2NR^1R^2$, or —S(=O)$_2R^3$, $R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^4$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —C(=O)— or —S(=O)$_2$—;

$R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 1-4;

Ring A is heterocycloalkyl;

each $R^7$ is independently deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

p is 0-4;

L is absent or —O—;

Ring B is cycloalkyl, heterocycloalkyl, aryl, or heteroaryl;

each $R^8$ is independently deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

q is 0-4;

each $R^a$ is independently $C_1$-$C_6$alkyl, $C_1$-$C_6$haloalkyl, $C_1$-$C_6$deuteroalkyl, or $C_1$-$C_6$hydroxyalkyl;

each $R^b$ is independently hydrogen, $C_1$-$C_6$alkyl, $C_1$-$C_6$haloalkyl, $C_1$-$C_6$deuteroalkyl, or $C_1$-$C_6$hydroxyalkyl; and each $R^c$ and $R^d$ are independently hydrogen, $C_1$-$C_6$alkyl, $C_1$-$C_6$haloalkyl, $C_1$-$C_6$deuteroalkyl, or $C_1$-$C_6$hydroxyalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (II), Y is $C_1$-$C_6$haloalkyl. In some embodiments of a compound of Formula (II), Y is —S(=O)$_2NR^1R^2$. In some embodiments of a compound of Formula (II), Y is —S(=O)$_2R^3$. In some embodiments of a compound of Formula (II), Y is —S(=O)$_2NR^1R^2$ or —S(=O)$_2R^3$. In some embodiments of a compound of Formula (I), Y is O$C_1$-$C_6$haloalkyl. In some embodiments of a compound of Formula (II), Y is $C_1$-$C_6$haloalkyl or O$C_1$-$C_6$haloalkyl.

In some embodiments of a compound of Formula (II), $R^1$ and $R^2$ are independently hydrogen or $C_1$-$C_6$alkyl. In some embodiments of a compound of Formula (II), $R^1$ and $R^2$ are independently $C_1$-$C_6$alkyl.

In some embodiments of a compound of Formula (II), $R^3$ is $C_1$-$C_6$alkyl.

In some embodiments of a compound of Formula (II), n is 3. In some embodiments of a compound of Formula (II), n is 2. In some embodiments of a compound of Formula (II), n is 1. In some embodiments of a compound of Formula (II), n is 0. In some embodiments of a compound of Formula (II), n is 0 or 1. In some embodiments of a compound of Formula (II), n is 0-2. In some embodiments of a compound of Formula (II), n is 1 or 2.

In some embodiments of a compound of Formula (II), each $R^4$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (II), each $R^4$ is independently deuterium, halogen, $C_1$-$C_6$alkyl, $C_1$-$C_6$haloalkyl, or $C_1$-$C_6$deuteroalkyl. In some embodiments of a compound of Formula (II), each $R^4$ is independently deuterium, halogen, or $C_1$-$C_6$alkyl.

In some embodiments of a compound of Formula (II), Z is —C(=O)—. In some embodiments of a compound of Formula (II), Z is —S(=O)$_2$—.

In some embodiments of a compound of Formula (II), $R^5$ is hydrogen, $C_1$-$C_6$alkyl, $C_1$-$C_6$heteroalkyl, or cycloalkyl. In some embodiments of a compound of Formula (II), $R^5$ is hydrogen or $C_1$-$C_6$alkyl. In some embodiments of a compound of Formula (II), $R^5$ is hydrogen. In some embodiments of a compound of Formula (II), $R^5$ is $C_1$-$C_6$alkyl.

In some embodiments of a compound of Formula (II), m is 3. In some embodiments of a compound of Formula (II), m is 2. In some embodiments of a compound of Formula (II), m is 1. In some embodiments of a compound of Formula (II), m is 1 or 2.

In some embodiments of a compound of Formula (II), each $R^6$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (II), each $R^6$ is independently deuterium, halogen, $C_1$-$C_6$alkyl, $C_1$-$C_6$haloalkyl, or $C_1$-$C_6$deuteroalkyl. In some embodiments of a compound of Formula (II), each $R^6$ is independently deuterium, halogen, or $C_1$-$C_6$alkyl. In some embodiments of a compound of Formula (II), each $R^6$ is independently deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (II), each $R^6$ is independently halogen or $C_1$-$C_6$alkyl.

In some embodiments of a compound of Formula (II), Ring A is an N-linked heterocycloalkyl. In some embodiments of a compound of Formula (II), Ring A is a 5- or 6-membered heterocycloalkyl. In some embodiments of a compound of Formula (II), Ring A is a 5-membered heterocycloalkyl. In some embodiments of a compound of Formula (II), Ring A is a 6-membered heterocycloalkyl. In some embodiments of a compound of Formula (II), Ring A is piperidinyl, morpholinyl, or piperazinyl. In some embodiments of a compound of Formula (II), Ring A is piperidinyl.

In some embodiments of a compound of Formula (II), p is 3. In some embodiments of a compound of Formula (II), p is 2. In some embodiments of a compound of Formula (II), p is 1. In some embodiments of a compound of Formula (II), p is 0. In some embodiments of a compound of Formula (II), p is 0 or 1. In some embodiments of a compound of Formula (II), p is 0-2. In some embodiments of a compound of Formula (II), p is 1 or 2.

In some embodiments of a compound of Formula (II), each $R^7$ is independently $C_1$-$C_6$alkyl, $C_1$-$C_6$haloalkyl, or $C_1$-$C_6$deuteroalkyl. In some embodiments of a compound of Formula (II), each $R^7$ is independently $C_1$-$C_6$alkyl.

In some embodiments of a compound of Formula (II), L is absent. In some embodiments of a compound of Formula (II), L is —O—.

In some embodiments of a compound of Formula (II), Ring B is aryl or heteroaryl. In some embodiments of a compound of Formula (II), Ring B is phenyl. In some embodiments of a compound of Formula (II), Ring B is 6-membered heteroaryl. In some embodiments of a compound of Formula (II), Ring B is pyridinyl.

In some embodiments of a compound of Formula (II), each $R^8$ is independently deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (II), each $R^8$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (II), each $R^8$ is independently deuterium, halogen, $C_1$-$C_6$alkyl, $C_1$-$C_6$haloalkyl, or $C_1$-$C_6$deuteroalkyl.

In some embodiments of a compound of Formula (II), q is 3. In some embodiments of a compound of Formula (II), q is 2. In some embodiments of a compound of Formula (II), q is 1. In some embodiments of a compound of Formula (II), q is 0. In some embodiments of a compound of Formula (II), q is 0 or 1. In some embodiments of a compound of Formula (II), q is 0-2. In some embodiments of a compound of Formula (II), q is 1 or 2. In some embodiments of a compound of Formula (II), q is 0-3.

Also disclosed herein is a compound of Formula (III), or a pharmaceutically acceptable salt, solvate, or stereoisomer thereof:

Formula (III)

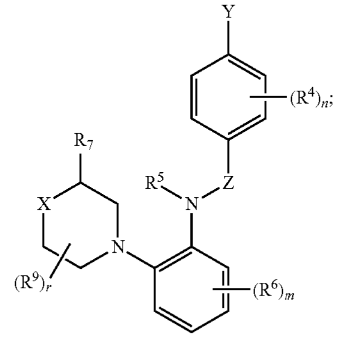

wherein:

Y is —$S(=O)_2NR^1R^2$, —$S(=O)_2R^3$, halogen, $C_1$-$C_6$alkyl, $C_1$-$C_6$haloalkyl, $C_1$-$C_6$deuteroalkyl, $OC_1$-$C_6$alkyl, $OC_1$-$C_6$haloalkyl, or $OC_1$-$C_6$deuteroalkyl;

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^1$ and $R^2$ are taken together to form a heterocycloalkyl optionally substituted with deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^4$ is independently deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —$C(=O)$— or —$S(=O)_2$—;

$R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-4;

X is —O—, —S—, —$S(=O)_2$—, —$NR^9$—, or —$C(R^9)_2$—;

$R^7$ is —W—$OR^{10}$, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, heterocycloalkyl, $C_1$-$C_6$alkyl(cycloalkyl), or $C_1$-$C_6$alkyl(heterocycloalkyl);

W is absent or $C_1$-$C_3$alkylene;

$R^{10}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^9$ is independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

r is 0-6;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Also disclosed herein is a compound of Formula (III), or a pharmaceutically acceptable salt, solvate, or stereoisomer thereof:

Formula (III)

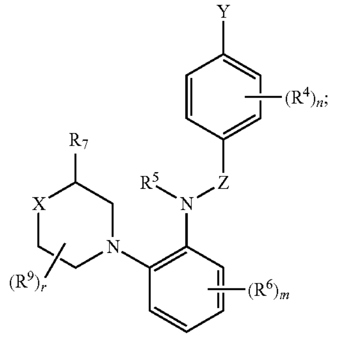

wherein:

Y is —S(═O)$_2NR^1R^2$, —S(═O)$_2R^3$, halogen, $C_1$-$C_6$alkyl, $C_1$-$C_6$haloalkyl, $C_1$-$C_6$deuteroalkyl, $OC_1$-$C_6$alkyl, $OC_1$-$C_6$haloalkyl, or $OC_1$-$C_6$deuteroalkyl;

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^4$ is independently deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —C(═O)— or —S(═O)$_2$—;

$R^5$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-4;

X is —O—, —S—, —S(=O)$_2$—, —NR$^9$—, or —C(R$^9$)$_2$—;

R$^7$ is —W—OR$^{10}$, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, heterocycloalkyl, $C_1$-$C_6$alkyl(cycloalkyl), or $C_1$-$C_6$alkyl(heterocycloalkyl);

W is absent or $C_1$-$C_3$alkylene;

R$^{10}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each R$^9$ is independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

r is 0-6;

each R$^a$ is independently $C_1$-$C_6$alkyl, $C_1$-$C_6$haloalkyl, $C_1$-$C_6$deuteroalkyl, or $C_1$-$C_6$hydroxyalkyl;

each R$^b$ is independently hydrogen, $C_1$-$C_6$alkyl, $C_1$-$C_6$haloalkyl, $C_1$-$C_6$deuteroalkyl, or $C_1$-$C_6$hydroxyalkyl; and each R$^c$ and R$^d$ are independently hydrogen, $C_1$-$C_6$alkyl, $C_1$-$C_6$haloalkyl, $C_1$-$C_6$deuteroalkyl, or $C_1$-$C_6$hydroxyalkyl;

or R$^c$ and R$^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (III), Y is —S(=O)$_2$NR$^1$R$^2$. In some embodiments of a compound of Formula (III), Y is —S(=O)$_2$R$^3$. In some embodiments of a compound of Formula (III), Y is —S(=O)$_2$NR$^1$R$^2$ or —S(=O)$_2$R$^3$. In some embodiments of a compound of Formula (III), Y is $C_1$-$C_6$alkyl, $C_1$-$C_6$haloalkyl, $C_1$-$C_6$deuteroalkyl, OC$_1$-$C_6$alkyl, OC$_1$-$C_6$haloalkyl, or OC$_1$-$C_6$deuteroalkyl. In some embodiments of a compound of Formula (III), Y is halogen. In some embodiments of a compound of Formula (III), Y is $C_1$-$C_6$alkyl, $C_1$-$C_6$haloalkyl, $C_1$-$C_6$deuteroalkyl. In some embodiments of a compound of Formula (III), Y is OC$_1$-$C_6$alkyl, OC$_1$-$C_6$haloalkyl, or OC$_1$-$C_6$deuteroalkyl. In some embodiments of a compound of Formula (III), Y is $C_1$-$C_6$haloalkyl. In some embodiments of a compound of Formula (III), Y is OC$_1$-$C_6$haloalkyl.

In some embodiments of a compound of Formula (III), R$^1$ and R$^2$ are independently hydrogen or $C_1$-$C_6$alkyl. In some embodiments of a compound of Formula (III), R$^1$ and R$^2$ are independently $C_1$-$C_6$alkyl.

In some embodiments of a compound of Formula (III), R$^3$ is $C_1$-$C_6$alkyl.

In some embodiments of a compound of Formula (III), n is 3. In some embodiments of a compound of Formula (III), n is 2. In some embodiments of a compound of Formula (III), n is 1. In some embodiments of a compound of Formula (III), n is 0. In some embodiments of a compound of Formula (III), n is 0 or 1. In some embodiments of a compound of Formula (III), n is 0-2. In some embodiments of a compound of Formula (III), n is 1 or 2.

In some embodiments of a compound of Formula (III), each R$^4$ is independently deuterium, halogen, —CN, —OH, —OR$^a$, —NR$^c$R$^d$, $C_1$-$C_6$alkyl, $C_1$-$C_6$haloalkyl, or $C_1$-$C_6$deuteroalkyl. In some embodiments of a compound of Formula (III), each R$^4$ is independently deuterium, halogen, $C_1$-$C_6$alkyl, $C_1$-$C_6$haloalkyl, or $C_1$-$C_6$deuteroalkyl. In some embodiments of a compound of Formula (III), each R$^4$ is independently deuterium, halogen, or $C_1$-$C_6$alkyl.

In some embodiments of a compound of Formula (III), Z is —C(=O)—. In some embodiments of a compound of Formula (III), Z is —S(=O)$_2$—.

In some embodiments of a compound of Formula (III), R$^5$ is hydrogen, $C_1$-$C_6$alkyl, $C_1$-$C_6$heteroalkyl, or cycloalkyl. In some embodiments of a compound of Formula (III), R$^5$ is hydrogen or $C_1$-$C_6$alkyl. In some embodiments of a compound of Formula (III), R$^5$ is hydrogen. In some embodiments of a compound of Formula (III), R$^5$ is $C_1$-$C_6$alkyl.

In some embodiments of a compound of Formula (III), m is 3. In some embodiments of a compound of Formula (III), m is 2. In some embodiments of a compound of Formula (III), m is 1. In some embodiments of a compound of Formula (III), m is 0. In some embodiments of a compound of Formula (III), m is 0 or 1. In some embodiments of a compound of Formula (III), m is 0-2. In some embodiments of a compound of Formula (III), m is 1 or 2.

In some embodiments of a compound of Formula (III), each R$^6$ is independently deuterium, halogen, —CN, —OH, —OR$^a$, —NR$^c$R$^d$, $C_1$-$C_6$alkyl, $C_1$-$C_6$haloalkyl, or $C_1$-$C_6$deuteroalkyl. In some embodiments of a compound of Formula (III), each R$^6$ is independently deuterium, halogen, $C_1$-$C_6$alkyl, $C_1$-$C_6$haloalkyl, or $C_1$-$C_6$deuteroalkyl. In some embodiments of a compound of Formula (III), each R$^6$ is independently deuterium, halogen, or $C_1$-$C_6$alkyl. In some embodiments of a compound of Formula (III), each R$^6$ is independently deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (III), each R$^6$ is independently halogen or $C_1$-$C_6$alkyl.

In some embodiments of a compound of Formula (III), X is —O—. In some embodiments of a compound of Formula (III), X is —C(R$^9$)$_2$—. In some embodiments of a compound of Formula (III), X is —CH$_2$—. In some embodiments of a compound of Formula (III), X is —NR$^9$—. In some embodiments of a compound of Formula (III), X is —NH—. In some embodiments of a compound of Formula (III), X is —S—. In some embodiments of a compound of Formula (III), X is —S(=O)$_2$—.

In some embodiments of a compound of Formula (III), R$^7$ is —W—OR$^{10}$, $C_2$-$C_6$alkynyl, or cycloalkyl. In some embodiments of a compound of Formula (III), R$^7$ is —W—OR$^{10}$. In some embodiments of a compound of Formula (III), $R^7$ is $C_2$-$C_6$alkynyl. In some embodiments of a compound of Formula (III), $R^7$ is cycloalkyl.

In some embodiments of a compound of Formula (III), W is absent. In some embodiments of a compound of Formula (III), W is C1 alkylene.

In some embodiments of a compound of Formula (III), $R^{10}$ is aryl or $C_1$-$C_6$alkyl(aryl).

In some embodiments of a compound of Formula (III), each $R^9$ is independently hydrogen, deuterium, halogen, $C_1$-$C_6$alkyl, $C_1$-$C_6$haloalkyl, or $C_1$-$C_6$deuteroalkyl. In some embodiments of a compound of Formula (III), each $R^9$ is hydrogen.

In some embodiments of a compound of Formula (III), r is 3. In some embodiments of a compound of Formula (III), r is 2. In some embodiments of a compound of Formula (III), r is 1. In some embodiments of a compound of Formula (III), r is 0. In some embodiments of a compound of Formula (III), r is 0 or 1. In some embodiments of a compound of Formula (III), r is 0-2. In some embodiments of a compound of Formula (III), r is 1 or 2.

Also disclosed herein is a compound of Formula (IV), or a pharmaceutically acceptable salt, solvate, or stereoisomer thereof:

Formula (IV)

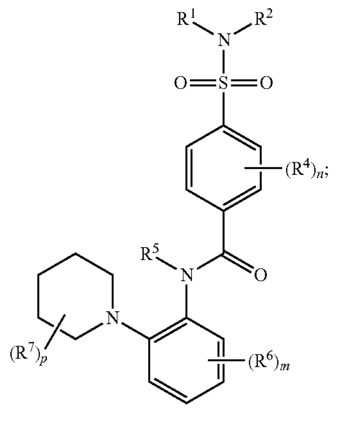

wherein:

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^1$ and $R^2$ are taken together to form a heterocycloalkyl optionally substituted with deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^4$ is independently deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

$R^5$ is $C_2$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-4;

each $R^7$ is independently deuterium, halogen, —CN, —$NO_2$, —OH, —$OR^{10}$, —OC(═O)$R^{10}$, —OC(═O)$OR^{11}$, —OC(═O)$NR^{12}R^{13}$, —SH, —$SR^{10}$, —S(═O)$R^{10}$, —S(═O)$_2R^{10}$, —S(═O)$_2NR^{12}R^{13}$, —$NR^{12}R^{13}$, —$NR^{11}$C(═O)$NR^{12}R^{13}$, —$NR^{11}$C(═O)$R^{10}$, —$NR^{11}$C(═O)$OR^{11}$, —$NR^{11}$S(═O)$_2R^{10}$, —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{7a}$;

each $R^{7a}$ is independently deuterium, halogen, —CN, —$NO_2$, —OH, —$OR^a$, —OC(═O)$R^a$, —OC(═O)$OR^b$, —OC(═O)$NR^cR^d$, —$NR^cR^d$, —$NR^b$C(═O)$NR^cR^d$, —$NR^b$C(═O)$R^a$, —$NR^b$C(═O)$OR^b$, —$NR^b$S(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{7a}$ on the same atom are taken together to form an oxo;

p is 0-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; and each $R^{12}$ and $R^{13}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or $R^{12}$ and $R^{13}$ are taken together with the atom to which they are attached to form a heterocycloalkyl optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (IV), $R^1$ and $R^2$ are independently hydrogen or $C_1$-$C_6$alkyl. In some embodiments of a compound of Formula (IV), $R^1$ and $R^2$ are independently $C_1$-$C_6$alkyl.

In some embodiments of a compound of Formula (IV), n is 3. In some embodiments of a compound of Formula (IV), n is 2. In some embodiments of a compound of Formula (IV), n is 1. In some embodiments of a compound of Formula (IV), n is 0. In some embodiments of a compound of Formula (IV), n is 0 or 1. In some embodiments of a compound of Formula (IV), n is 0-2. In some embodiments of a compound of Formula (IV), n is 1 or 2.

In some embodiments of a compound of Formula (IV), each $R^4$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (IV), each $R^4$ is independently deuterium, halogen, $C_1$-$C_6$alkyl, $C_1$-$C_6$haloalkyl, or $C_1$-$C_6$deuteroalkyl. In some embodiments of a compound of Formula (IV), each $R^4$ is independently deuterium, halogen, or $C_1$-$C_6$alkyl.

In some embodiments of a compound of Formula (IV), $R^5$ is $C_2$-$C_6$alkyl, $C_1$-$C_6$haloalkyl, $C_1$-$C_6$deuteroalkyl, $C_1$-$C_6$heteroalkyl, cycloalkyl, or heterocycloalkyl. In some embodiments of a compound of Formula (IV), $R^5$ is $C_2$-$C_6$alkyl, $C_1$-$C_6$heteroalkyl, or cycloalkyl. In some embodiments of a compound of Formula (IV), $R^5$ is $C_2$-$C_6$alkyl. In some embodiments of a compound of Formula (IV), $R^5$ is $C_1$-$C_6$heteroalkyl. In some embodiments of a compound of Formula (IV), $R^5$ is cycloalkyl.

In some embodiments of a compound of Formula (IV), m is 3. In some embodiments of a compound of Formula (IV), m is 2. In some embodiments of a compound of Formula (IV), m is 1. In some embodiments of a compound of Formula (IV), m is 0. In some embodiments of a compound of Formula (IV), m is 0 or 1. In some embodiments of a compound of Formula (IV), m is 0-2. In some embodiments of a compound of Formula (IV), m is 1 or 2.

In some embodiments of a compound of Formula (IV), each $R^6$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (IV), each $R^6$ is independently deuterium, halogen, $C_1$-$C_6$alkyl, $C_1$-$C_6$haloalkyl, or $C_1$-$C_6$deuteroalkyl. In some embodiments of a compound of Formula (IV), each $R^6$ is independently deuterium, halogen, or $C_1$-$C_6$alkyl. In some embodiments of a compound of Formula (IV), each $R^6$ is independently deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (IV), each $R^6$ is independently halogen or $C_1$-$C_6$alkyl.

In some embodiments of a compound of Formula (IV), each $R^7$ is independently deuterium, halogen, —CN, —OH, —$OR^{10}$, —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein the alkyl, cycloalkyl, heterocycloalkyl, aryl, and heteroaryl is optionally and independently substituted with one or more $R^{7a}$. In some embodiments of a compound of Formula (IV), each $R^7$ is independently —$OR^{10}$, $C_1$-$C_6$alkyl, $C_1$-$C_6$haloalkyl, $C_1$-$C_6$deuteroalkyl, aryl, or heteroaryl; wherein the alkyl, aryl, and heteroaryl is optionally and independently substituted with one or more $R^{7a}$. In some embodiments of a compound of Formula (IV), each $R^7$ is independently —$OR^{10}$ or $C_1$-$C_6$alkyl optionally and independently substituted with one or more $R^{7a}$. In some embodiments of a compound of Formula (IV), $R^7$ is —$OR^{10}$. In some embodiments of a compound of Formula (IV), each $R^7$ is independently $C_1$-$C_6$alkyl, aryl, or heteroaryl; wherein the alkyl, aryl, and heteroaryl is optionally and independently substituted with one or more $R^{7a}$. In some embodiments of a compound of Formula (IV), each $R^7$ is independently $C_1$-$C_6$alkyl or aryl; wherein the alkyl and aryl is optionally and independently substituted with one or more $R^{7a}$. In some embodiments of a compound of Formula (IV), each $R^7$ is independently $C_1$-$C_6$alkyl or heteroaryl; wherein the alkyl and heteroaryl is optionally and independently substituted with one or more $R^{7a}$.

In some embodiments of a compound of Formula (IV), each $R^{7a}$ is independently deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; or two $R^{7a}$ on the same atom are taken together to form an oxo. In some embodiments of a compound of Formula (IV), each $R^{7a}$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl; or two $R^{7a}$ on the same atom are taken together to form an oxo. In some embodiments of a compound of Formula (IV), each $R^{7a}$ is independently deuterium, halogen, —OH, —$OR^a$, $C_1$-$C_6$alkyl, $C_1$-$C_6$haloalkyl, or $C_1$-$C_6$deuteroalkyl.

In some embodiments of a compound of Formula (IV), p is 3. In some embodiments of a compound of Formula (IV), p is 2. In some embodiments of a compound of Formula (IV), p is 1. In some embodiments of a compound of Formula (IV), p is 0. In some embodiments of a compound of Formula (IV), p is 1 or 2. In some embodiments of a compound of Formula (IV), p is 0-2.

In some embodiments of a compound of Formula (IV), each $R^{10}$ is independently aryl or heteroaryl; wherein each aryl and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (IV), each $R^{10}$ is independently aryl or heteroaryl; wherein each aryl and heteroaryl is independently optionally substituted with one or more deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (IV), each $R^{10}$ is independently aryl optionally substituted with one or more deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (IV), each $R^{10}$ is independently heteroaryl optionally substituted with one or more deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (IV), each $R^{10}$ is independently aryl optionally substituted with one or more deuterium, halogen, $C_1$-$C_6$alkyl, $C_1$-$C_6$haloalkyl, or $C_1$-$C_6$deuteroalkyl. In some embodiments of a compound of Formula (IV), each $R^{10}$ is independently heteroaryl optionally substituted with one or more deuterium, halogen, $C_1$-$C_6$alkyl, $C_1$-$C_6$haloalkyl, or $C_1$-$C_6$deuteroalkyl.

In some embodiments of a compound of Formula (IV), each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, cycloalkyl, heterocycloalkyl, aryl, and heteroaryl is independently optionally substituted with one or more deuterium, halogen, —CN, —OH, —OH, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (IV), each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; wherein each alkyl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl.

In some embodiments of a compound of Formula (IV), each $R^{12}$ and $R^{13}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (IV), each $R^{12}$ and $R^{13}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; wherein each alkyl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl.

In some embodiments of a compound disclosed herein, each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl.

In some embodiments of a compound disclosed herein, each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^b$ is independently hydrogen, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^b$ is independently hydrogen, $C_1$-$C_6$alkyl, $C_1$-$C_6$haloalkyl, cycloalkyl, or heterocycloalkyl. In some embodiments of a compound disclosed herein, each $R^b$ is independently hydrogen, $C_1$-$C_6$alkyl, or $C_1$-$C_6$haloalkyl. In some embodiments of a compound disclosed herein, each $R^b$ is independently hydrogen or $C_1$-$C_6$alkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^c$ and $R^d$ are independently hydrogen, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^c$ and $R^d$ are independently hydrogen, $C_1$-$C_6$alkyl, $C_1$-$C_6$haloalkyl, cycloalkyl, or heterocycloalkyl. In some embodiments of a compound disclosed herein, each $R^c$ and $R^d$ are independently hydrogen, $C_1$-$C_6$alkyl, or $C_1$-$C_6$haloalkyl. In some embodiments of a compound disclosed herein, each $R^c$ and $R^d$ are independently hydrogen or $C_1$-$C_6$alkyl.

In some embodiments of a compound disclosed herein, $R^c$ and $R^d$ are taken together with the atom to which they are attached to form a heterocycloalkyl optionally substituted with one or more oxo, deuterium, halogen, —CN, —OH, —$OCH_3$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound disclosed herein, each $R^7$, $R^{10}$, $R^{11}$, $R^{12}$, $R^{13}$, $R^a$, $R^b$, $R^c$, $R^a$, the heterocycloalkyl formed when $R^{12}$ and $R^{13}$ are taken together, the heterocycloalkyl formed when $R^c$ and $R^d$ are taken together, is independently substituted with one, two, three, or four substituents as defined herein. In some embodiments of a compound disclosed herein, each $R^7$, $R^1$, $R^{11}$, $R^{12}$, $R^{13}$, $R^b$, $R^c$, $R^d$, the heterocycloalkyl formed when $R^{12}$ and $R^{13}$ are taken together, the heterocycloalkyl formed when $R^c$ and $R^d$ are taken together, is independently substituted with one, two, or three substituents as defined herein. In some embodiments of a compound disclosed herein, each $R^7$, $R^{10}$, $R^{11}$, $R^{12}$, $R^{13}$, $R^a$, $R^b$, $R^c$, $R^d$, the heterocycloalkyl formed when $R^{12}$ and $R^{13}$ are taken together, the heterocycloalkyl formed when $R^c$ and $R^d$ are taken together, is independently substituted with one or two substituents as defined herein. In some embodiments of a compound disclosed herein, each $R^7$, $R^{10}$, $R^{11}$, $R^{12}$, $R^{13}$, $R^a$, $R^b$, $R^c$, $R^d$, the heterocycloalkyl formed when $R^{12}$ and $R^{13}$ are taken together, the heterocycloalkyl formed when $R^c$ and $R^d$ are taken together, is independently substituted with one substituent as defined herein.

Any combination of the groups described above for the various variables is contemplated herein. Throughout the specification, groups and substituents thereof are chosen by one skilled in the field to provide stable moieties and compounds.

In some embodiments, the compound is selected from a compound found in table 1:
| Ex. # | Structure | Chemical Name |
| --- | --- | --- |
| 1 | 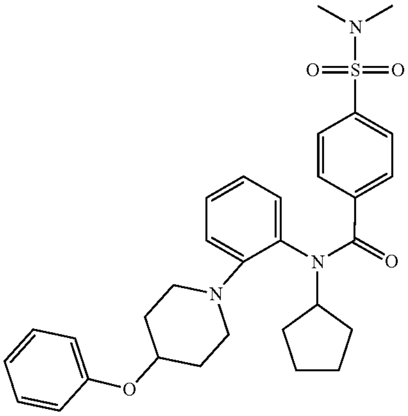 [SMILES: CN(C)S(=O)(=O)c1ccc(C(=O)N(c2ccccc2N2CCC(Oc3ccccc3)CC2)C2CCCC2)cc1] | N-cyclopentyl-4-(N,N-dimethylsulfamoyl)-N-(2-(4-phenoxypiperidin-1-yl)phenyl)benzamide |
| 2 | 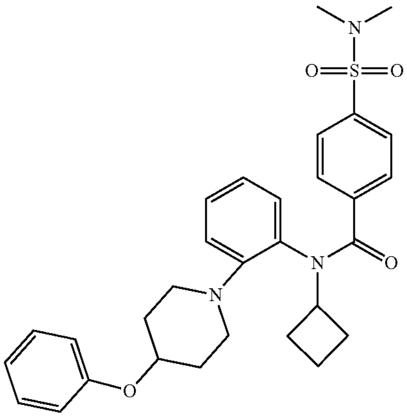 [SMILES: CN(C)S(=O)(=O)c1ccc(C(=O)N(c2ccccc2N2CCC(Oc3ccccc3)CC2)C2CCC2)cc1] | N-cyclobutyl-4-(N,N-dimethylsulfamoyl)-N-(2-(4-phenoxypiperidin-1-yl)phenyl)benzamide |
| 3 | 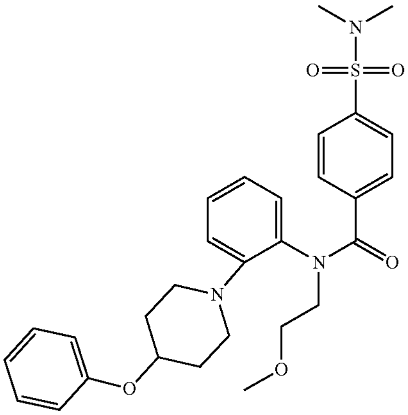 [SMILES: COCCN(C(=O)c1ccc(S(=O)(=O)N(C)C)cc1)c1ccccc1N1CCC(Oc2ccccc2)CC1] | 4-(N,N-dimethylsulfamoyl)-N-(2-methoxyethyl)-N-(2-(4-phenoxypiperidin-1-yl)phenyl)benzamide |

-continued
| Ex. # | Structure | Chemical Name |
|---|---|---|
| 4 | 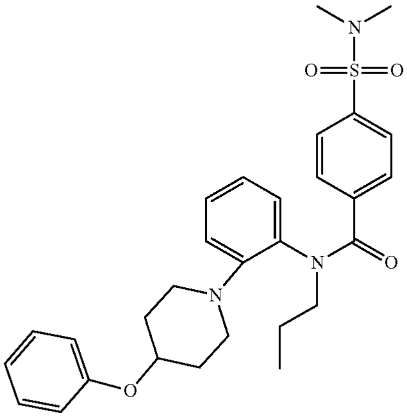 [SMILES: CCCN(C(=O)c1ccc(S(=O)(=O)N(C)C)cc1)c1ccccc1N1CCC(Oc2ccccc2)CC1] | 4-(N,N-dimethylsulfamoyl)-N-(2-(4-phenoxypiperidin-1-yl)phenyl)-N-propylbenzamide |
| 5 | 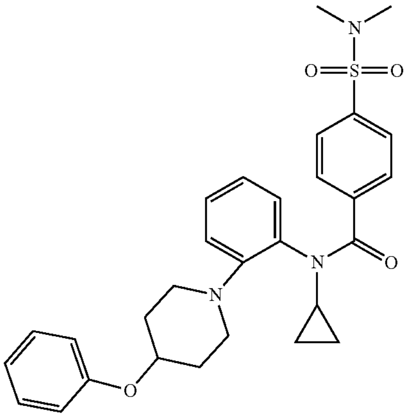 [SMILES: CN(C)S(=O)(=O)c1ccc(C(=O)N(c2ccccc2N2CCC(Oc3ccccc3)CC2)C2CC2)cc1] | N-cyclopropyl-4-(N,N-dimethylsulfamoyl)-N-(2-(4-phenoxypiperidin-1-yl)phenyl)benzamide |
| 6 | 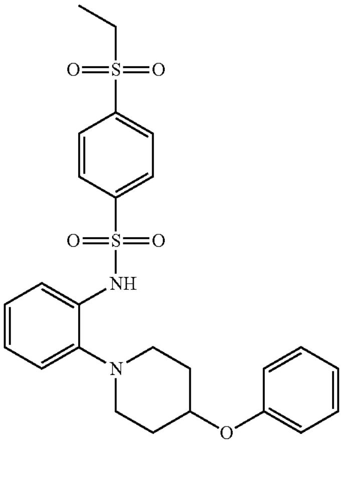 [SMILES: CCS(=O)(=O)c1ccc(S(=O)(=O)Nc2ccccc2N2CCC(Oc3ccccc3)CC2)cc1] | 4-(ethylsulfonyl)-N-(2-(4-phenoxypiperidin-1-yl)phenyl)benzenesulfonamide |

-continued
| Ex. # | Structure | Chemical Name |
|---|---|---|
| 7 | 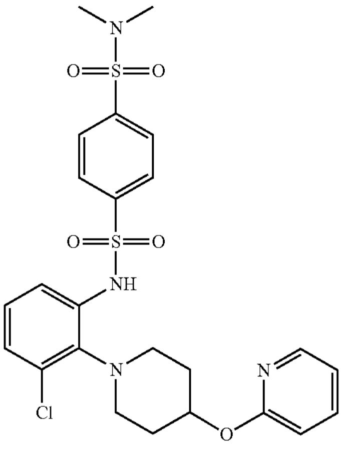 [SMILES: CN(C)S(=O)(=O)c1ccc(S(=O)(=O)Nc2cccc(Cl)c2N2CCC(Oc3ccccn3)CC2)cc1] | $N^1$-(3-chloro-2-(4-(pyridin-2-yloxy)piperidin-1-yl)phenyl)-$N^4$,$N^4$-dimethylbenzene-1,4-disulfonamide |
| 8 | 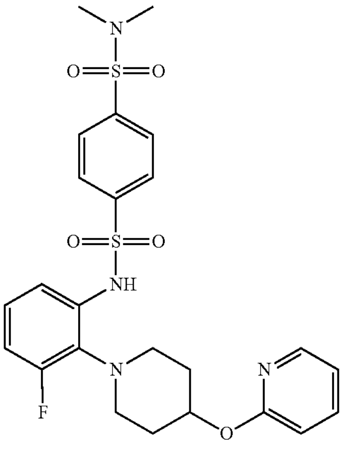 [SMILES: CN(C)S(=O)(=O)c1ccc(S(=O)(=O)Nc2cccc(F)c2N2CCC(Oc3ccccn3)CC2)cc1] | $N^1$-(3-fluoro-2-(4-(pyridin-2-yloxy) piperidin-1-yl)phenyl)-$N^4$,$N^4$-dimethylbenzene-1,4-disulfonamide |
| 9 | 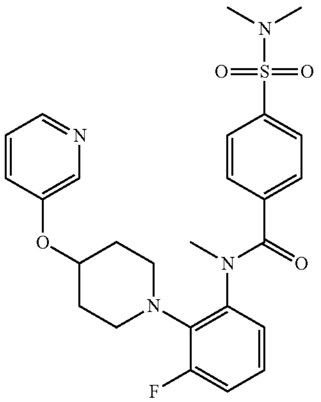 [SMILES: CN(C(=O)c1ccc(S(=O)(=O)N(C)C)cc1)c1cccc(F)c1N1CCC(Oc2cccnc2)CC1] | 4-(N,N-dimethylsulfamoyl)-N-(3-fluoro-2-(4-(pyridin-2-yloxy)piperidin-1-yl)phenyl)-N-methylbenzamide |

-continued
| Ex. # | Structure | Chemical Name |
|---|---|---|
| 10 | 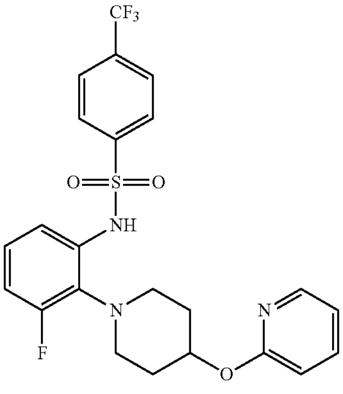 [SMILES: O=S(=O)(Nc1cccc(F)c1N1CCC(Oc2ccccn2)CC1)c1ccc(C(F)(F)F)cc1] | N-(3-fluoro-2-(4-(pyridin-2-yloxy)piperidin-1-yl)phenyl)-4-(trifluoromethyl)benzenesulfonamide |
| 11 | 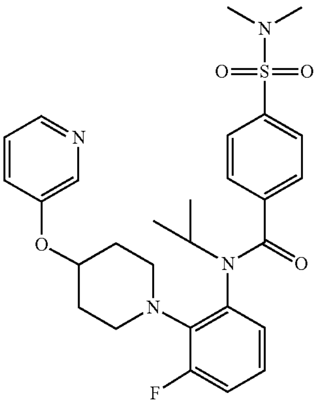 [SMILES: CC(C)N(C(=O)c1ccc(S(=O)(=O)N(C)C)cc1)c1cccc(F)c1N1CCC(Oc2cccnc2)CC1] | 4-(N,N-dimethylsulfamoyl)-N-(3-fluoro-2-(4-(pyridin-2-yloxy)piperidin-1-yl)phenyl)-N-isopropylbenzamide |
| 12 | 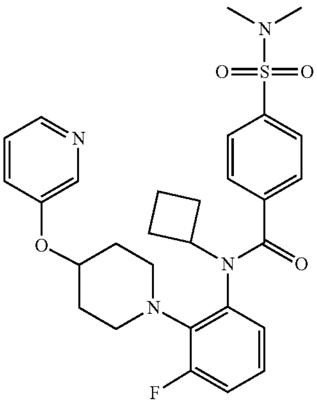 [SMILES: CN(C)S(=O)(=O)c1ccc(C(=O)N(c2cccc(F)c2N2CCC(Oc3cccnc3)CC2)C2CCC2)cc1] | N-cyclobutyl-4-(N,N-dimethylsulfamoyl)-N-(3-fluoro-2-(4-(pyridin-2-yloxy)piperidin-1-yl)phenyl)benzamide |

-continued
| Ex. # | Structure | Chemical Name |
|---|---|---|
| 13 | 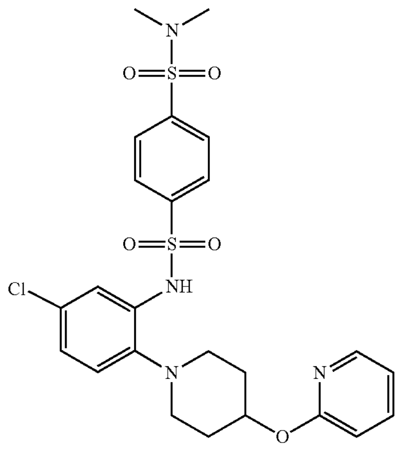 [SMILES: CN(C)S(=O)(=O)c1ccc(S(=O)(=O)Nc2cc(Cl)ccc2N2CCC(Oc3ccccn3)CC2)cc1] | $N^1$-(5-chloro-2-(4-(pyridin-2-yloxy) piperidin-1-yl)phenyl)-$N^4$,$N^4$-dimethylbenzene-1,4-disulfonamide |
| 14 | 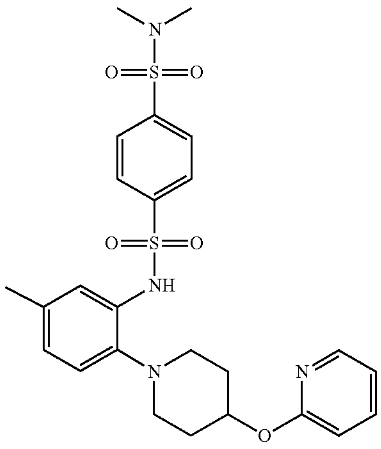 [SMILES: Cc1ccc(N2CCC(Oc3ccccn3)CC2)c(NS(=O)(=O)c2ccc(S(=O)(=O)N(C)C)cc2)c1] | $N^1$,$N^1$-dimethyl-$N^4$-(5-methyl-2-(4-(pyridin-2-yloxy)piperidin-1-yl)phenyl)benzene-1,4-disulfonamide |
| 15 | 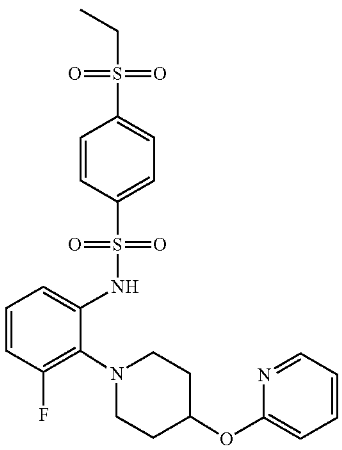 [SMILES: CCS(=O)(=O)c1ccc(S(=O)(=O)Nc2cccc(F)c2N2CCC(Oc3ccccn3)CC2)cc1] | 4-(ethylsulfonyl)-N-(3-fluoro-2-(4-(pyridin-2-yloxy)piperidin-1-yl)phenyl)benzenesulfonamide |

-continued
| Ex. # | Structure | Chemical Name |
|---|---|---|
| 16 | 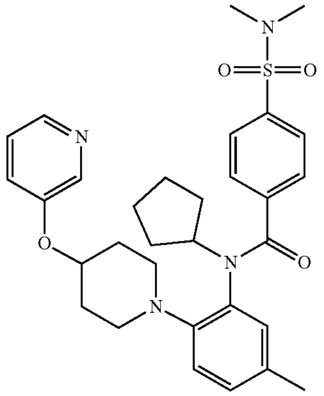 [SMILES: Cc1ccc(N2CCC(Oc3cccnc3)CC2)c(N(C(=O)c2ccc(S(=O)(=O)N(C)C)cc2)C2CCCC2)c1] | N-cyclopentyl-4-(N,N-dimethylsulfamoyl)-N-(5-methyl-2-(4-(pyridin-2-yloxy)piperidin-1-yl)phenyl)benzamide |
| 17 | 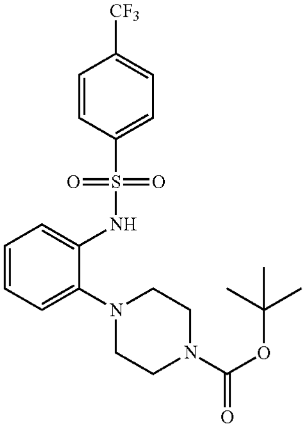 [SMILES: CC(C)(C)OC(=O)N1CCN(c2ccccc2NS(=O)(=O)c2ccc(C(F)(F)F)cc2)CC1] | tert-butyl 4-(2-((4-(trifluoromethyl)phenyl)sulfonamido)phenyl) piperazine-1-carboxylate |
| 18 | 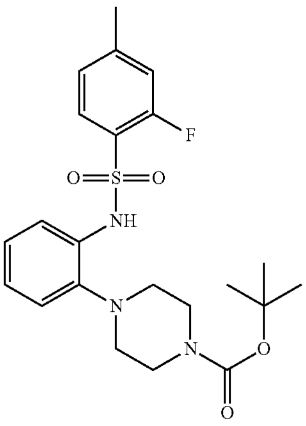 [SMILES: Cc1ccc(S(=O)(=O)Nc2ccccc2N2CCN(C(=O)OC(C)(C)C)CC2)c(F)c1] | tert-butyl 4-(2-((2-fluoro-4-methylphenyl)sulfonamido)phenyl)piperazine-1-carboxylate |

-continued
| Ex. # | Structure | Chemical Name |
|---|---|---|
| 19 | 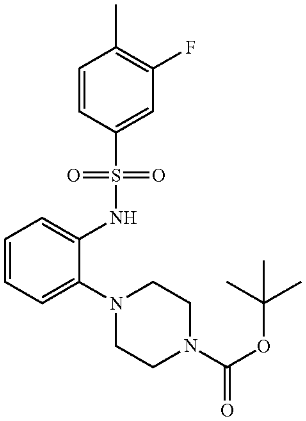 [SMILES: Cc1ccc(S(=O)(=O)Nc2ccccc2N2CCN(C(=O)OC(C)(C)C)CC2)cc1F] | tert-butyl 4-(2-((3-fluoro-4-methylphenyl)sulfonamido)phenyl)piperazine-1-carboxylate |
| 20 | 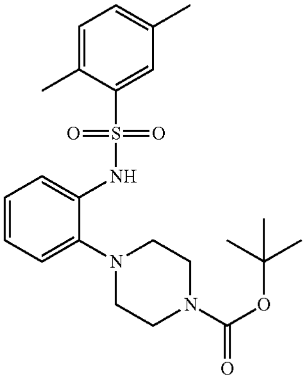 [SMILES: Cc1ccc(C)c(S(=O)(=O)Nc2ccccc2N2CCN(C(=O)OC(C)(C)C)CC2)c1] | tert-butyl 4-(2-((2,5-dimethylphenyl)sulfonamido)phenyl)piperazine-1-carboxylate |
| 21 | 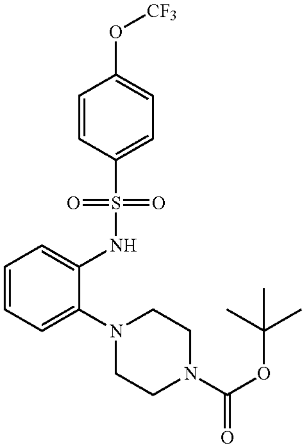 [SMILES: CC(C)(C)OC(=O)N1CCN(c2ccccc2NS(=O)(=O)c2ccc(OC(F)(F)F)cc2)CC1] | tert-butyl 4-(2-((4-(trifluoromethoxy)phenyl)sulfonamido)phenyl) piperazine-1-carboxylate |

-continued
| Ex. # | Structure | Chemical Name |
|---|---|---|
| 22 | 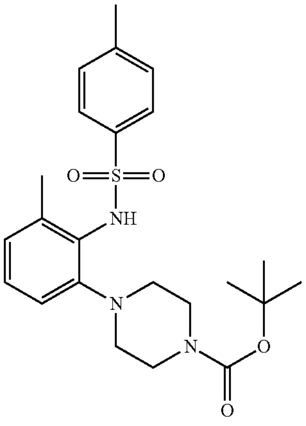 [SMILES: Cc1ccc(S(=O)(=O)Nc2c(C)cccc2N2CCN(C(=O)OC(C)(C)C)CC2)cc1] | tert-butyl 4-(3-methyl-2-((4-methylphenyl)sulfonamido)phenyl)piperazine-1-carboxylate |
| 23 | 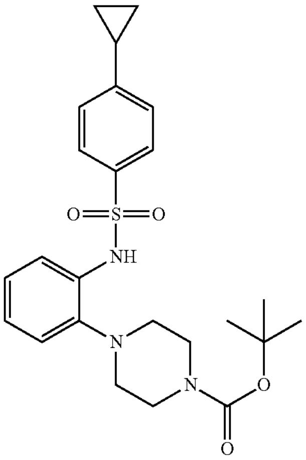 [SMILES: CC(C)(C)OC(=O)N1CCN(c2ccccc2NS(=O)(=O)c2ccc(C3CC3)cc2)CC1] | tert-butyl 4-(2-((4-cyclopropylphenyl)sulfonamido)phenyl) piperazine-1-carboxylate |
| 24 | 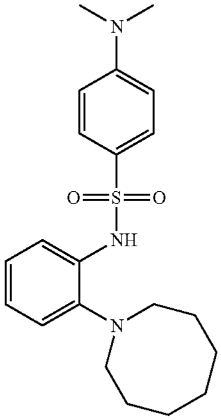 [SMILES: CN(C)c1ccc(S(=O)(=O)Nc2ccccc2N2CCCCCCC2)cc1] | N1-(2-(azocan-1-yl)phenyl)-N4,N4-dimethylbenzene-1,4-disulfonamide |

-continued
| Ex. # | Structure | Chemical Name |
|---|---|---|
| 25 | 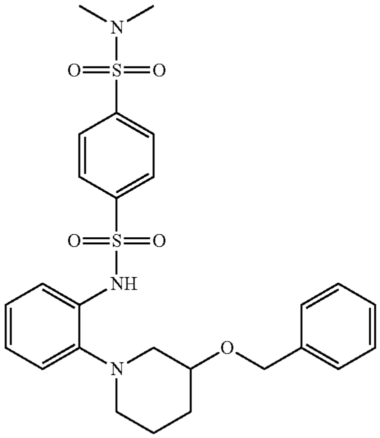 [SMILES: CN(C)S(=O)(=O)c1ccc(S(=O)(=O)Nc2ccccc2N2CCCC(OCc3ccccc3)C2)cc1] | $N^1$-(2-(3-(benzyloxy)piperidin-1-yl)phenyl)-$N^4$,$N^4$-dimethylbenzene-1,4-disulfonamide |
| 26 | 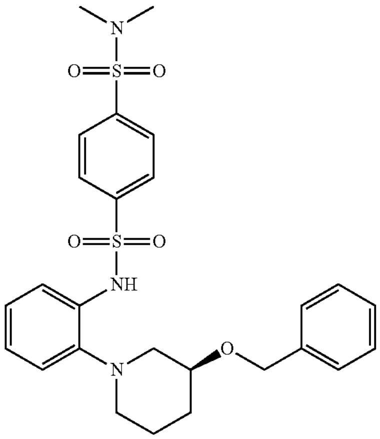 [SMILES: CN(C)S(=O)(=O)c1ccc(S(=O)(=O)Nc2ccccc2N2CCC[C@H](OCc3ccccc3)C2)cc1] | (S)-$N^1$-(2-(3-(benzyloxy)piperidin-1-yl)phenyl)-$N^4$,$N^4$-dimethylbenzene-1,4-disulfonamide |
| 27 | 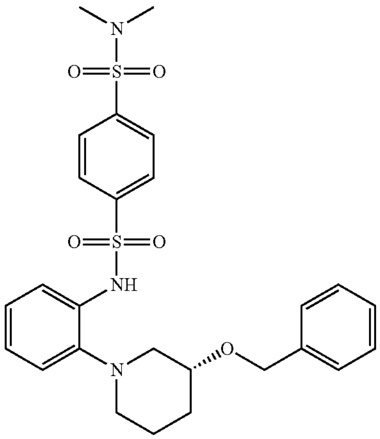 [SMILES: CN(C)S(=O)(=O)c1ccc(S(=O)(=O)Nc2ccccc2N2CCC[C@@H](OCc3ccccc3)C2)cc1] | (R)-$N^1$-(2-(3-(benzyloxy)piperidin-1-yl)phenyl)-$N^4$,$N^4$-dimethylbenzene-1,4-disulfonamide |

-continued
| Ex. # | Structure | Chemical Name |
|---|---|---|
| 28 | 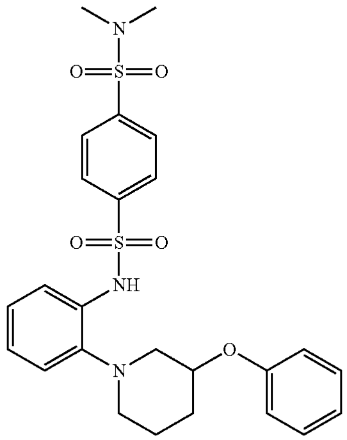 | $N^1$,$N^1$-dimethyl-$N^4$-(2-(3-phenoxypiperidin-1-yl)phenyl)benzene-1,4-disulfonamide |
| 29 | 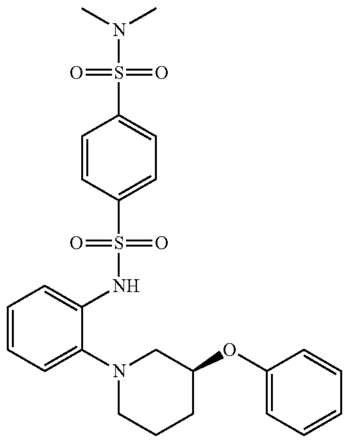 [SMILES: CN(C)S(=O)(=O)c1ccc(S(=O)(=O)Nc2ccccc2N2CCC[C@H](Oc3ccccc3)C2)cc1] | (S)-$N^1$,$N^1$-dimethyl-$N^4$-(2-(3-phenoxypiperidin-1-yl)phenyl)benzene-1,4-disulfonamide |
| 30 | 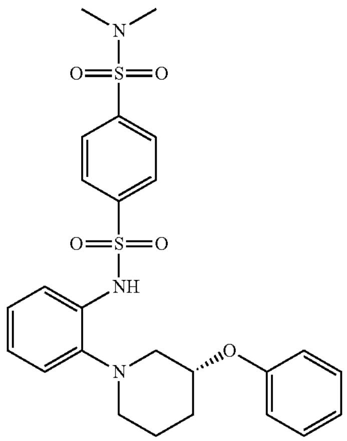 [SMILES: CN(C)S(=O)(=O)c1ccc(S(=O)(=O)Nc2ccccc2N2CCC[C@@H](Oc3ccccc3)C2)cc1] | (R)-$N^1$,$N^1$-dimethyl-$N^4$-(2-(3-phenoxypiperidin-1-yl)phenyl)benzene-1,4-disulfonamide |

-continued
| Ex. # | Structure | Chemical Name |
|---|---|---|
| 31 | 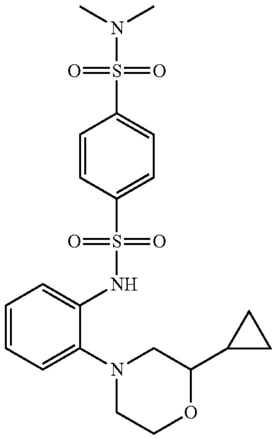 [SMILES: CN(C)S(=O)(=O)c1ccc(S(=O)(=O)Nc2ccccc2N2CCOC(C3CC3)C2)cc1] | $N^1$-(2-(2-cyclopropylmorpholino) phenyl)-$N^4$, $N^4$-dimethylbenzene-1,4-disulfonamide |
| 32 | 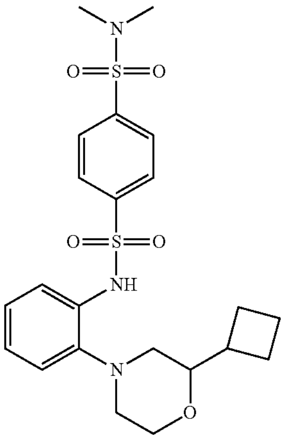 [SMILES: CN(C)S(=O)(=O)c1ccc(S(=O)(=O)Nc2ccccc2N2CCOC(C3CCC3)C2)cc1] | $N^1$-(2-(2-cyclobutylmorpholino)phenyl)-$N^4$,$N^4$-dimethylbenzene-1,4-disulfonamide |
| 33 | 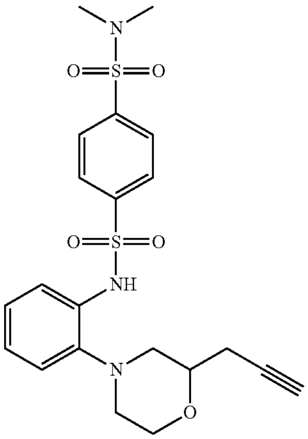 [SMILES: C#CCC1CN(c2ccccc2NS(=O)(=O)c2ccc(S(=O)(=O)N(C)C)cc2)CCO1] | $N^1$,$N^1$-dimethyl-$N^4$-(2-(2-(prop-2-yn-1-yl) morpholino)phenyl)benzene-1,4-disulfonamide |

-continued
| Ex. # | Structure | Chemical Name |
|---|---|---|
| 34 | 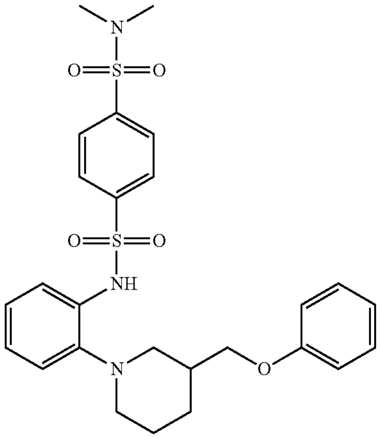 [SMILES: CN(C)S(=O)(=O)c1ccc(S(=O)(=O)Nc2ccccc2N2CCCC(COc3ccccc3)C2)cc1] | $N^1$,$N^1$-dimethyl-$N^4$-(2-(3-(phenoxymethyl)piperidin-1-yl)phenyl)benzene-1,4-disulfonamide |
| 35 | 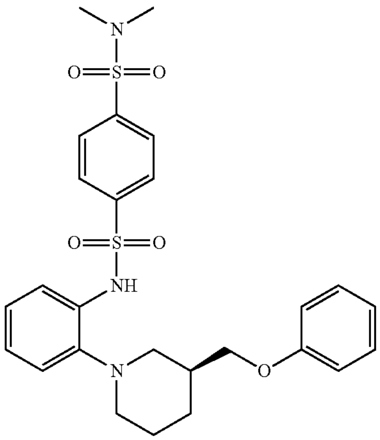 [SMILES: CN(C)S(=O)(=O)c1ccc(S(=O)(=O)Nc2ccccc2N2CCC[C@H](COc3ccccc3)C2)cc1] | (S)-$N^1$,$N^1$-dimethyl-$N^4$-(2-(3-(phenoxymethyl)piperidin-1-yl)phenyl)benzene-1,4-disulfonamide |
| 36 | 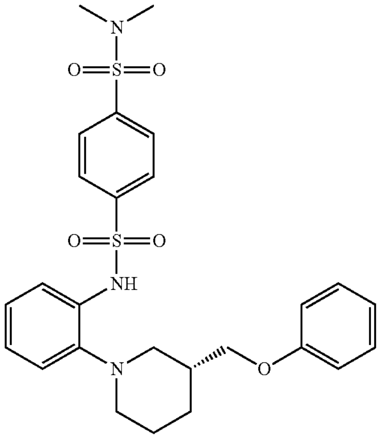 [SMILES: CN(C)S(=O)(=O)c1ccc(S(=O)(=O)Nc2ccccc2N2CCC[C@@H](COc3ccccc3)C2)cc1] | (R)-$N^1$,$N^1$-dimethyl-$N^4$-(2-(3-(phenoxymethyl) piperidin-1-yl)phenyl)benzene-1,4-disulfonamide |

-continued
| Ex. # | Structure | Chemical Name |
|---|---|---|
| 37 | 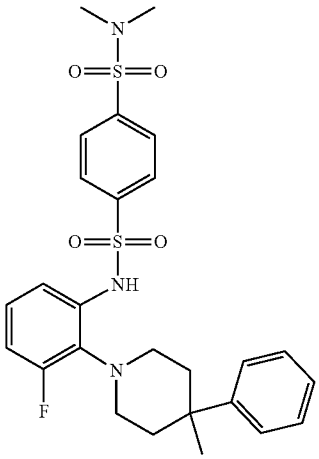 [SMILES: CN(C)S(=O)(=O)c1ccc(S(=O)(=O)Nc2cccc(F)c2N2CCC(C)(c3ccccc3)CC2)cc1] | $N^1$-(3-fluoro-2-(4-methyl-4-phenylpiperidin-1-yl) phenyl)-$N^4$,$N^4$-dimethylbenzene-1,4 disulfonamide |
| 38 | 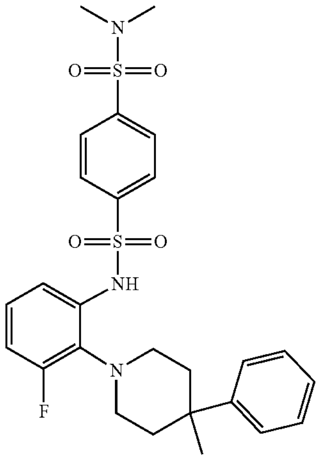 [SMILES: CN(C)S(=O)(=O)c1ccc(S(=O)(=O)Nc2cccc(F)c2N2CCC(C)(c3ccccc3)CC2)cc1] | $N^1$,$N^1$-dimethyl-$N^4$-(2-(4-methyl-4-phenylpiperidin-1-yl)phenyl)benzene-1,4-disulfonamide |
| 39 | 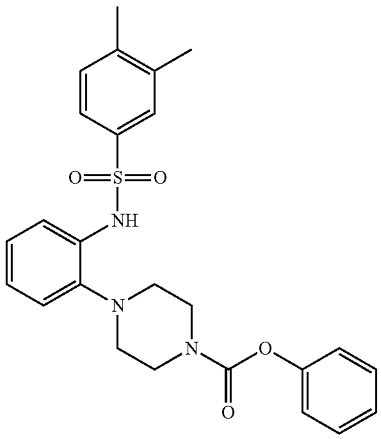 [SMILES: Cc1ccc(S(=O)(=O)Nc2ccccc2N2CCN(C(=O)Oc3ccccc3)CC2)cc1C] | phenyl 4-(2-((3,4-dimethylphenyl)sulfonamido)phenyl) piperazine-1-carboxylate |

-continued
| Ex. # | Structure | Chemical Name |
|---|---|---|
| 40 | 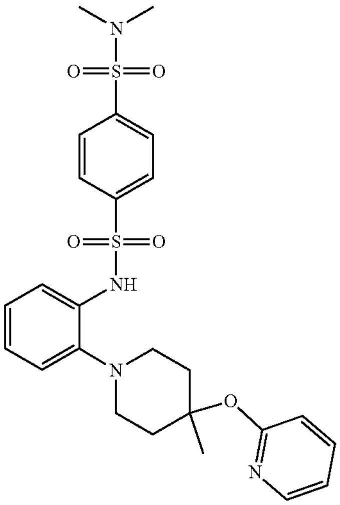 [SMILES: CN(C)S(=O)(=O)c1ccc(S(=O)(=O)Nc2ccccc2N2CCC(C)(Oc3ccccn3)CC2)cc1] | $N^1$,$N^1$-dimethyl-$N^4$-(2-(4-methyl-4-(pyridin-2-yloxy)piperidin-1-yl)phenyl)benzene-1,4-disulfonamide |
| 41 | 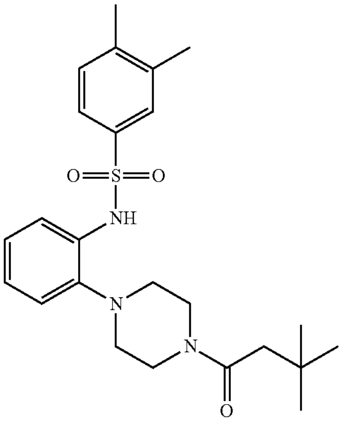 [SMILES: Cc1ccc(S(=O)(=O)Nc2ccccc2N2CCN(C(=O)CC(C)(C)C)CC2)cc1C] | N-(2-(4-(3,3-dimethylbutanoyl)piperazin-1-yl)phenyl)-3,4-dimethylbenzenesulfonamide |
| 42 | 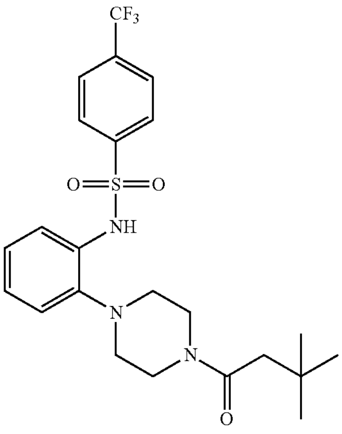 [SMILES: CC(C)(C)CC(=O)N1CCN(c2ccccc2NS(=O)(=O)c2ccc(C(F)(F)F)cc2)CC1] | N-(2-(4-(3,3-dimethylbutanoyl)piperazin-1-yl)phenyl)-4-(trifluoromethyl)benzenesulfonamide |

-continued

| Ex. # | Structure | Chemical Name |
|---|---|---|
| 43 | 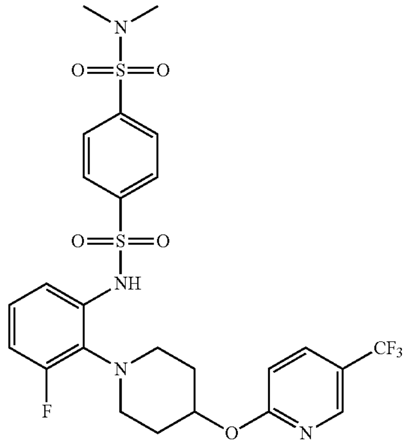 [SMILES: CN(C)S(=O)(=O)c1ccc(S(=O)(=O)Nc2cccc(F)c2N2CCC(Oc3ccc(C(F)(F)F)cn3)CC2)cc1] | $N^1$-(3-fluoro-2-(4-((5-(trifluoromethyl)pyridin-2-yl)oxy)piperidin-1-yl)phenyl)-$N^4$,$N^4$-dimethylbenzene-1,4-disulfonamide |
| 44 | 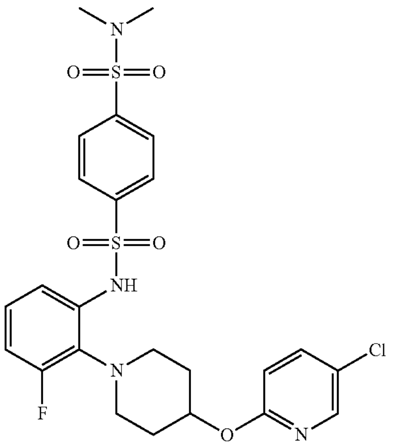 [SMILES: CN(C)S(=O)(=O)c1ccc(S(=O)(=O)Nc2cccc(F)c2N2CCC(Oc3ccc(Cl)cn3)CC2)cc1] | $N^1$-(2-(4-((5-chloropyridin-2-yl)oxy)piperidin-1-yl)-3-fluorophenyl)-$N^4$,$N^4$-dimethylbenzene-1,4-disulfonamide |
| 45 | 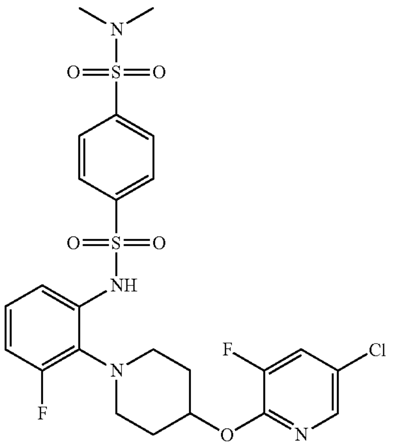 [SMILES: CN(C)S(=O)(=O)c1ccc(S(=O)(=O)Nc2cccc(F)c2N2CCC(Oc3ncc(Cl)cc3F)CC2)cc1] | $N^1$-(2-(4-((5-chloro-3-fluoropyridin-2-yl)oxy)piperidin-1-yl)-3-fluorophenyl)-$N^4$,$N^4$-dimethylbenzene-1,4-disulfonamide |

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^{+}(C_{1-4}\ alkyl)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Provided herein are methods for treating TRPML1-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. Certain embodiments provide therapeutic compositions comprising at least one compound disclosed herein in combination with one or more additional agents for the treatment of TRPML1-mediated disorders.

Also provided herein are compounds for use in the manufacture of a medicament for the treatment of a TRPML1 mediated disease. Further provided herein is a method of treatment of a disease mediated by TRPML1 activity, in a mammalian subject, which comprising administering a therapeutically effective amount of a compound disclosed herein.

TRPML1-mediated diseases include proliferative disorders such as cancers, inflammatory disorders, pain, neurodegenerative disorders, cognitive and psychiatric disorders, and other diseases as disclosed below.

TRPML1-mediated disorder or disease is aging, bone diseases, cardiovascular diseases, congenital developmental disorders, eye diseases, hematological and solid malignancies, infectious diseases, inflammatory diseases, liver diseases, metabolic diseases, neurological or neurodegenerative diseases, pancreatitis, renal diseases, skeletal muscle disorders, obesity, lysosomal storage diseases, hypertrophic cardiomyopathy, dilated cardiomyopathy, inclusion body myositis, Paget's disease, or pulmonary diseases In some embodiments, the TRPML1-mediated disorder or disease is Aicardi-Goutières syndrome, Alzheimer's Disease, amyotrophic lateral sclerosis, ataxia-telangiectasia, autism spectrum disorders, Batten Disease, bipolar disorder, cerebral ataxia, Charcot-Marie-Tooth variant diseases, Chronic Wasting Disease, corticobasal degeneration, corticobasal syndrome, bovine spongiform encephalopathy, Creutzfeldt-Jacob Disease, Danon Disease, Duchenne Muscular Dystrophy, Exotic ungulate encephalopathy, Fabre Disease, Fatal Familial insomnia, Friedreich Ataxia, Feline spongiform Encephalopathy, Fragile X, Frontal temporal dementia, Gaucher Disease, Gerstmann-Straussler-Scheinker Disease, Giant axonal neuropathy, GM1 and GM2 gangliosidosis, Huntington's Disease, Infantile Refsum Disease, JUNQ and IPOD, Kuru, Leukoencephalopathy, Lewy Body Dementia, locomotor ataxia, Lyme disease, Machado Joseph Disease, major depressive disorder, MPS-III, Mucolipidosis, multiple sulfatase deficiency, multiple systems atrophy, myofibrillar myopathies, myotonic dystrophy, Niemann-Pick Disease, Parkinson's Disease, Parkinsonism, Pick's disease, polyglutamine diseases, Pompe Disease, pontocerebellar hypoplasia, prion diseases, progressive nuclear palsy, pyruvate dehydrogenase deficiency, Sandhoff Disease, Schizophrenia, Scrapie, Shy-Drager syndrome, spinal muscular atrophy, spinocerebellar ataxias, sporadic familial insomnia, subacute degeneration of the spinal cord, subacute sclerosing panencephalitis, Tay-Sachs disease, transneuronal degeneration, Progressive Supranuclear Palsy, Spinocerebellar Ataxia's, or vascular dementia.

Compounds disclosed herein are useful for the treatment of neurodegenerative disorders of various origins such as Alzheimer's disease and other dementia conditions such as Lewy body dementia, fronto-temporal dementia and other taupathies; amyotrophic lateral sclerosis, multiple sclerosis, Parkinson's disease and other parkinsonian syndromes; Huntington's disease; HIV-induced neuroinflammation; essential tremors; other spinocerebellar degenerations, neuropathies such as Charcot-Marie-Tooth neuropathy and other TRPML1-mediated diseases such as Type IV mucolipidosis (MLIV). The compounds disclosed herein are also useful for the treatment of neurological conditions such as epilepsy including simple partial seizure, complex partial seizure, secondary generalized seizure, further including absence seizure, myoclonic seizure, clonic seizure, tonic seizure, tonic clonic seizure and atonic seizure, and for prevention and treatment of status epilepticus (SE).

The compounds disclosed herein are also useful for the treatment of cognitive disorders and of psychiatric disorders. Psychiatric disorders include, and are not limited to major depression, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behavior, delusional disorders, brief psychotic disorders, shared psychotic disorders, psychotic disorder due to a general medical condition, substance-induced psychotic disorders or a psychotic disorder not otherwise specified, anxiety disorders such as generalized anxiety disorder, panic disorders, posttraumatic stress disorder, impulse control disorders, phobic disorders, dissociative states and moreover in smoke, drug addiction and alcoholism. In particular bipolar disorders, psychosis, anxiety and addiction.

The compounds disclosed herein are useful in the prevention or treatment of neuroinflammation and CNS damage induced by HIV infection and of HIV-associated neurocognitive deficits. The compounds disclosed herein are useful in the prevention or treatment of neuropathic pain. Neuropathic pain syndromes include, and are not limited to: chemotherapy-induced peripheral neuropathy, diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and peripheral forms of pain such as complex regional pain syndromes (CRPS) also called reflex sympathetic dystrophies.

The compounds disclosed herein are also useful for the treatment of pain, including chronic pain. Chronic pain includes, and is not limited to, chronic pain caused by inflammation or an inflammatory-related condition, osteoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds disclosed herein are also useful in the treatment of acute pain caused by acute injury, illness, sport-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis or surgery (such as open heart or bypass surgery), post-operative pain, kidney stone pain, gallbladder pain, gallstone pain, obstetric pain or dental pain.

The compounds disclosed herein are also useful in the treatment of headaches such as migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

Compounds disclosed herein are also useful in the treatment of diseases such as vertigo, tinnitus, muscle spasm, and other disorders including and not limited to cardiovascular diseases (such as cardiac arrhythmia, cardiac infarction or angina pectoris, hypertension, cardiac ischemia, cerebral ischemia) endocrine disorders (such as acromegaly or diabetes insipidus) diseases in which the pathophysiology of the disorder involves excessive or hypersecretory or otherwise inappropriate cellular secretion of an endogenous substance (such as catecholamine, a hormone or a growth factor).

The compounds disclosed herein are also useful in the selective treatment of liver disease, such as inflammatory liver diseases, for example chronic viral hepatitis B, chronic viral hepatitis C, alcoholic liver injury, primary biliary cirrhosis, autoimmune hepatitis, liver fibrosis, non-alcoholic steatohepatitis and liver transplant rejection.

The compounds disclosed herein inhibit inflammatory processes affecting all body systems. Therefore, they are useful in the treatment of inflammatory processes of the musculoskeletal system of which the following is a list of examples but it is not comprehensive of all target disorders: arthritic conditions such as ankylosing spondylitis, cervical arthritis, fibromyalgia, gout, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis nodosa, thyroiditis, aplastic anaemia, scleroderma, myasthenia gravis, multiple sclerosis and other demyelinating disorders, encephalomyelitis, sarcoidosis, nephritic syndrome, Bechet's syndrome, polymyositis, gingivitis.

Compounds disclosed herein are also useful in the treatment of gastrointestinal (GI) tract disorders such as inflammatory bowel disorders (IBD) including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varioliforme, ulcerative colitis, peptic ulceration, pyrosis, and other damage to the GI tract, for example, by *Helicobacter* pylon, gastroesophageal reflux disease, gastroparesis, such as diabetic gastroparesis; and other functional bowel disorders, such as non-ulcerative dyspepsia (NUD); pancreatitis, emesis, diarrhoea, and visceral inflammation.

Compounds disclosed herein are also useful in the treatment of disorders of the genito-urinary tract such as overactive bladder, prostatitis (chronic bacterial and chronic nonbacterial prostatitis), prostadynia, interstitial cystitis, urinary incontinence and benign prostatic hyperplasia, annexities, pelvic inflammation, bartholinities and vaginitis. In particular, overactive bladder and urinary incontinence.

Compounds disclosed herein are also useful in the treatment of renal disorders including diabetic nephropathy, renal allograft rejection, infectious renal diseases, IgA nephropathy, fibrotic kidney disease, lupus nephritis and glomerulonephritis, acute kidney injury and renal carcinoma.

The compounds disclosed herein are also useful in the treatment of ophthalmic diseases such as retinitis, retinopathies, uveitis and acute injury to the eye tissue, age-related macular degeneration or glaucoma, conjunctivitis.

The compounds disclosed herein are also useful in the treatment of eating disorders such as anorexia nervosa including the subtypes restricting type and binge-eating/purging type; bulimia nervosa including the subtypes purging type and non-purging type; obesity; compulsive eating disorders; binge eating disorder; and eating disorder not otherwise specified.

The compounds disclosed herein are also useful in the treatment of allergic dermatitis, hyper-responsiveness of the airway, chronic obstructive pulmonary disease (COPD), bronchitis, septic shock, Sjögren's syndrome, glomerulonephritis, atherosclerosis, growth and metastases of malignant cells, myoblastic leukaemia, diabetes, meningitis, osteoporosis, burn injury, ischaemic heart disease, stroke, peripheral vascular disease, varicose veins, glaucoma.

In some embodiments, the compounds and pharmaceutical compositions of the present disclosure are useful in the treatment or prevention of progression of cancer. In some embodiments, the cancer is a hematologic malignancy or solid tumor. Hematologic malignancies include leukemias, lymphomas, multiple myeloma, and subtypes thereof. Lymphomas can be classified various ways, often based on the underlying type of malignant cell, including Hodgkin's lymphoma (often cancers of Reed-Sternberg cells, but also sometimes originating in B cells; all other lymphomas are non-Hodgkin's lymphomas), B-cell lymphomas, T-cell lymphomas, mantle cell lymphomas, Burkitt's lymphoma, follicular lymphoma, and others as defined herein and known in the art.

B-cell lymphomas include, but are not limited to, diffuse large B-cell lymphoma (DLBCL), chronic lymphocytic leukemia (CLL)/small lymphocytic lymphoma (SLL), and others as defined herein and known in the art.

T-cell lymphomas include T-cell acute lymphoblastic leukemia/lymphoma (T-ALL), peripheral T-cell lymphoma (PTCL), T-cell chronic lymphocytic leukemia (T-CLL) Sezary syndrome, and others as defined herein and known in the art.

Leukemias include acute myeloid (or myelogenous) leukemia (AML), chronic myeloid (or myelogenous) leukemia (CML), acute lymphocytic (or lymphoblastic) leukemia (ALL), chronic lymphocytic leukemia (CLL) hairy cell leukemia (sometimes classified as a lymphoma) and others as defined herein and known in the art.

Plasma cell malignancies include lymphoplasmacytic lymphoma, plasmacytoma, and multiple myeloma.

Solid tumors include melanomas, neuroblastomas, gliomas or 5 carcinomas such as tumors of the brain, head and neck, breast, lung (e.g., non-small cell lung cancer, NSCLC), reproductive tract (e.g., ovary), upper digestive tract, pancreas, liver, renal system (e.g., kidneys), bladder, prostate and colorectum.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients or diluents, in a pharmaceutical composition, according to standard pharmaceutical practice. In one embodiment, the compounds disclosed herein may be administered to animals. The compounds can be administered orally or parenterally, including the intravenous, intramuscular, intraperitoneal, subcutaneous, rectal and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating a TRPML1-mediated disorder or disease using a compound disclosed herein, or a pharmaceutically acceptable salt, solvate, or stereoisomer thereof, in combination with an additional therapeutic agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

General Synthetic Methods Nomenclature and Structures

In general, the nomenclature used in this Application is based on ChemSketch™ (ACDLabs) and generated according to the IUPAC systematic nomenclature. Chemical structures shown herein were prepared using ISIS® version 2.2. Certain compounds were drawn using CambridgeSoft's ChemDraw 18.0. Any open valency appearing on a carbon, oxygen, sulfur, or nitrogen atom in the structures herein indicates the presence of a hydrogen atom unless indicated otherwise. Where a nitrogen-containing heteroaryl ring is shown with an open valency on a nitrogen atom and variables such as $R^1$, $R^2$, $R^3$ etc. are shown on the heteroaryl ring, such variables may be bound or joined to the open valency nitrogen.

Abbreviations

Abbreviations which are used in the description of the Schemes and the Examples that follows include: ACN: Acetonitrile; AcOEt: Ethyl acetate; $CH_3I$: Iodomethane; $CH_3CH_2I$: Iodoethane; $(CH_3)_2CHI$: 2-Iodopropane; DCM: Dichloromethane; DMF: Dimethylformamide; DMSO: Dimethylsulfoxide; ESI: Electrospray ionization; h: hour; HATU:1-[Bis(dimethylamino)methylene]-1H-1,2,3-triazolo [4,5-b]pyridinium-3-oxide; exafluorophosphate; $K_2CO_3$: Potassium carbonate; M: Molar; MeOH: Methanol; Min: Minute(s); NMR: Nuclear Magnetic Resonance; NaH: Sodium hydride; NaOH: Sodium hydroxide; $Na_2SO_4$: Sodium sulfate; on: overnight; rt: Room Temperature; TFA: Trifluoroacetic acid; THF: Tetrahydrofuran; TEA: Triethylamine; UPLC-MS: UltraPerformance Liquid Chromatography-Mass Spectrometry; y: yield or yields.

The following examples illustrate the present invention. Unless explicitly stated otherwise, all measurements (especially percentages and amounts) relate to the weight.

Preparation of Intermediates (XII)

Scheme 1

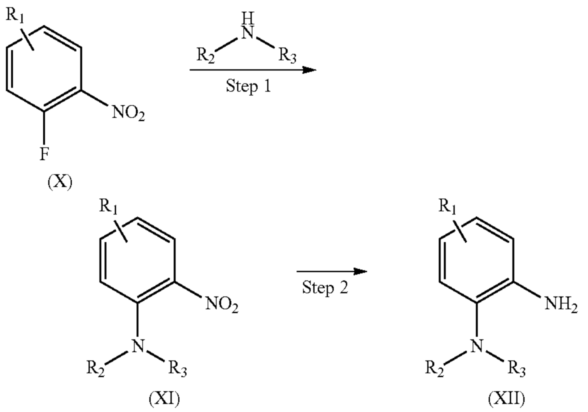

Intermediates of type XII were prepared utilizing the method described in Scheme I above by the general procedures described below.

Step 1. To a stirred solution of commercially available 2-Flouro-nitrobenze of type X (1.0 eq) in ACN (10 mL) was added $K_2CO_3$ (3 eq) followed by the addition of commercially available amine compound (1 eq). The reaction mixture was stirred at 80° C. for 4 h. After completion [Monitored with TLC] reaction mixture was diluted with water and extracted with EtOAc. Organic layer was separated, dried over sodium sulphate and concentrated under reduced pressure. Resultant crude material was purified by column chromatography using 0-10% ethyl acetate in hexane as eluting solvent to afford compounds of type XI as desired product.

Step 2. To a stirred solution of compound XI (1 eq) in 1,4-dioxane (9 mL) was added $NH_4Cl$ (7 eq) in $H_2O$ (3 mL). Then Zn dust (7 eq) was added to the reaction mixture at ice-cold condition, and the reaction was stirred at RT for 2 h. After completion [Monitored with TLC] insoluble part was filtered and filtrate part was concentrated under reduced pressure. The crude residue thus obtained was partitioned between EtOAc and water. Organic layer was separated, dried over sodium sulphate and concentrated under reduced pressure to afford amine intermediate XII as desired product. These compounds were used in the next step without further purification.

Preparation of Final Products of General Formula (XIII)

Final compounds of general formula XIII were generally synthesized according to the methods described below for Scheme 2.

Scheme 2

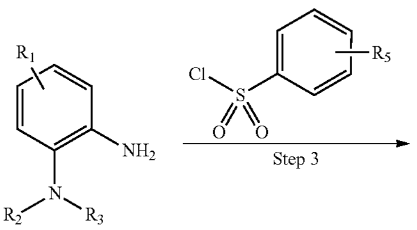

(XII)

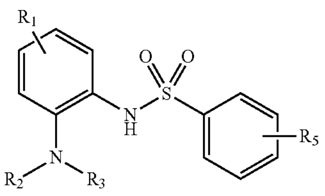

(XIII)

Step 3. To a stirred solution of amine intermediate XII (1.0 eq) in pyridine (2 mL) was added sulphonyl chloride (1.0 eq) and resultant reaction mixture was allowed to stir at room temperature for 1 h. After LC-MS analysis reaction mixture was concentrated under reduced pressure to remove excess pyridine. Resultant crude was subjected to silica chromatography to provide desired products of type XIII.

Preparation of Final Products of General Formula (XV)

Certain final examples of structure XV were synthesized by the general method below utilizing Scheme 3.

Scheme 3

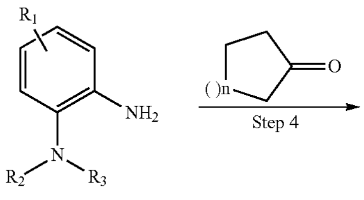

(XII)

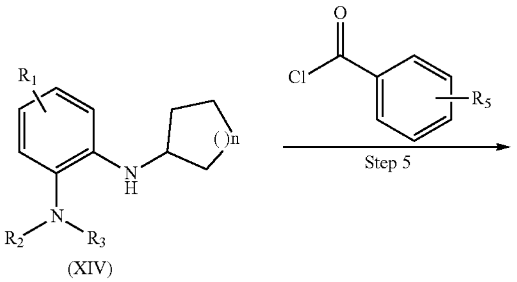

(XIV)

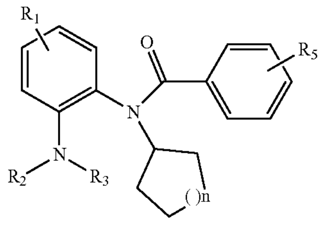

(XV)

Step 4. To a stirred solution of amine Intermediate (XII) (1 eq) and commercially available keto starting material (1.5 eq) in methanol (5 mL) was added acetic acid (0.3 mL) and stirred for 1 h. Then reaction mixture was cooled to 0° C. followed by addition of sodium cyanoborohydride (3 eq) and stirred overnight. After completion of reaction [Monitored with TLC], reaction mixture was quenched with water and evaporated under reduced pressure to remove MeOH. Then reaction mixture was partitioned between EtOAc and water. Organic layer was separated, washed with brine solution, dried over sodium sulphate and concentrated under reduced pressure. Crude compound was purified by column chromatography over silica gel to afford desired product (XIV).

Step 5. To a stirred solution of amine intermediate (XIV) (1 eq) and acyl chloride (1.5 eq) in THF (5 mL) was added $K_2CO_3$ (3 eq) and resultant reaction mixture was allowed to stir at room temperature for 16 h. After completion [monitored by TLC], reaction mixture was quenched with water and extracted by ethyl acetate. Combine organic layer was washed with brine solution, dried over sodium sulphate and concentrated under reduced pressure. Crude compound was purified by column chromatography to afford desired product (XV).

Preparation of Final Products of General Formula (XVII)

Certain compounds of formula XVII were synthesized by the method below described in Scheme 4.

Scheme 4

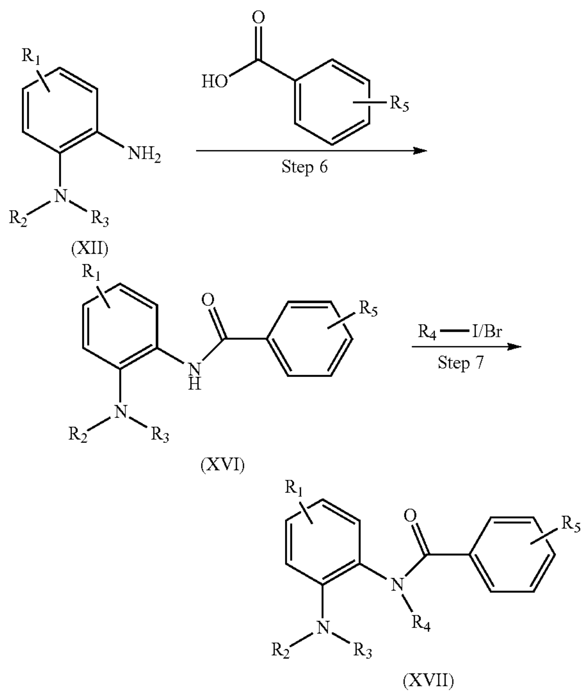

(XII) (XVI) (XVII)

Step 6. To an ice cooled solution of amine Intermediate XII (1 eq) in DMF (3.0 mL), DIPEA (6 eq) was added under nitrogen atmosphere. Afterwards, EDC (1.8 eq) and HOBT (1.8 eq) were added and the reaction stirred for 20 minutes. Then a solution of commercially available acid (1 eq) in DMF (2.0 mL) was added to it dropwise and stirred overnight at room temperature. After completion [Monitored with TLC], reaction mixture was diluted with ice water [100 mL] and extracted with EtOAc [75 mL×2]. Organic layer was separated, dried over sodium sulphate and concentrated under reduced pressure. Resultant crude was purified by column chromatography over silica gel using 0-10% ethyl acetate in hexane as eluting solvent to afford amide intermediate XVI.

Step 7. To a stirred solution of amide intermediate XVI (1.0 eq) in DMF (2 mL) was added NaH (4.0 eq) and an alkyl halide (1.0 eq) then resultant reaction mixture was allowed to stir at room temperature for 1 h. After LC-MS analysis reaction mixture was concentrated under reduced pressure to remove excess pyridine. Resultant crude was subjected to column chromatography over silica gel to provide desired product (XVII).

Example 1

Step-1. To a stirred solution of 4-phenoxypiperidine (500 mg, 2.89 mmol, 1 eq) in ACN (5 ml) was added 1-fluoro-2-nitrobenzene (488 mg, 3.17 mmol, 1.1 eq) followed by addition of caesium Carbonate (1.4 g, 4.3 mmol, 1.5 eq), resultant reaction mixture was allowed to stir at 90° C. temperature for 3 h. After completion [Monitored with TLC, Mobile Phase 10% EtOAc-Hexane, Rf-0.3], reaction mixture was quenched with water (100 ml) and extracted by ethyl acetate (100 ml×2). Combined organic layer was washed with brine solution (50 ml), dried over sodium sulphate and concentrated under reduced pressure. Resultant crude was purified by column chromatography using silica gel (100-200) as absorbent under gradient elution of 5-8% EtOAc/Hexane to afford 1-(2-nitrophenyl)-4-phenoxypiperidine (800 mg, 93%) as light brown liquid.

Step-2. To a stirred solution of 1-(2-nitrophenyl)-4-phenoxypiperidine (800 mg, 2.68 mmol, 1 eq) in ethanol (5 ml) was added 10% Pd—C (1.14 gm, 10.73 mmol, 4 eq) and allowed to stir overnight under hydrogen atmosphere. After completion [Monitored with TLC, Mobile Phase 20% EtOAc-Hexane, and Rf-0.4] heterogeneous reaction mixture was filtered through celite bed and celite bed was further washed with ethyl acetate (50 ml). The filtrate was concentrated under reduced pressure to afford crude 2-(4-phenoxypiperidin-1-yl) aniline (600 mg, 83%) as brown solid.

Step-3. To a stirred solution of 2-(4-phenoxypiperidin-1-yl) aniline (300 mg, 1.11 mmol, 1 eq) and cyclopentanone (0.157 ml, 1.67 mmol, 1.5 eq) in methanol (5 mL) was added acetic acid (0.3 mL) and stirred for 1 h. Then reaction mixture was cooled to 0° C. followed by addition of sodium cyanoborohydride (211 mg, 3.35 mmol, 3 eq) and stirred overnight at room temperature. After completion [Monitored with TLC, Mobile Phase 10% EtOAc-Hexane, and Rf-0.5], reaction mixture was quenched with water [10 mL] and evaporated under reduced pressure to remove MeOH. Then reaction mixture was partitioned between EtOAc (200 mL) and water (100 mL). Organic layer was separated, washed by brine solution (50 mL), dried over sodium sulphate and concentrated under reduced pressure. Crude compound was purified by column chromatography over silica gel (100-200), using 2-5% EtOAc/Hexane as eluting solvent to afford N-cyclopentyl-2-(4-phenoxypiperidin-1-yl) aniline (300 mg, 79%) as off white solid.

Step-4. To a stirred solution of N-cyclopentyl-2-(4-phenoxypiperidin-1-yl)aniline (70 mg, 0.21 mmol, 1 eq) and 4-(N,N-dimethylsulfamoyl)benzoyl chloride (CAS: 29171-70-8) (77 mg, 0.31 mmol, 1.1 eq) in THF (5 mL) was added $K_2CO_3$ (86 mg, 0.62 mmol, 3 eq) and resultant reaction mixture was allowed to stir at room temperature for 16 h. After completion [monitored by TLC, 20% EtOAc/Hexane Rf-0.3] reaction mixture was quenched with water (50 mL) and extracted by ethyl acetate (50 mL×2). Combined organic layer was washed by brine solution (50 mL), dried over sodium sulphate and concentrated under reduced pressure. Crude compound was purified by column chromatography over silica gel (100-200), using 0 to 20% EtOAc/Hexane to afford N-cyclopentyl-4-(N, N-dimethylsulfamoyl)-N-(2-(4-phenoxypiperidin-1-yl) phenyl)benzamide (40 mg, 35%) as a white solid.

Example 2

The title compound was prepared analogously to Example 1 utilizing cyclobutanone in step 3. And similar process was followed for step 4 and the crude was purified by column chromatography over silica gel (100-200), using 0 to 10% EtOAc/Hexane to afford N-cyclobutyl-4-(N, N-dimethylsulfamoyl)-N-(2-(4-phenoxypiperidin-1-yl) phenyl) benzamide (20 mg, 27%) as a white solid.

Example 3

Step 1. To a stirred solution of 4-phenoxypiperidine (5.0 g, 211.0 mmol, 1 eq) in ACN (50 mL) was added $K_2CO_3$ (9.82 g, 71.09 mmol, 3 eq) followed by the addition of 1-fluoro-2-nitrobenzene (6.68 g, 47.39 mmol, 2 eq). The reaction mixture was stirred at 80° C. temperature for 4 h. After completion [Monitored with TLC, Mobile Phase 5% EtOAc-Hexane, Rf-0.5] reaction mixture was concentrated and diluted with water [100 mL] and extracted with EtOAc [75 mL×2]. Organic layer was separated, dried over sodium sulphate and concentrated under reduced pressure. Resultant crude was purified by Combiflash column chromatography using 0-2% ethyl acetate in hexane as eluting solvent to afford 1-(2-nitrophenyl)-4-phenoxypiperidine (6.8 g, 97%) as pale yellow liquid.

Step 2. To a stirred solution 1-(2-nitrophenyl)-4-phenoxypiperidine (6.8 g, 22.81 mmol, 1 eq) in EtOH (70 mL) was added 10% Pd—C (7.6 g) under nitrogen atmosphere. Then the reaction was stirred at RT for 2 h. After completion [Monitored with TLC, Mobile Phase: 20% EtOAc-Hexane, Rf-0.4] insoluble part was filtered through glass sintered and filtrate part was concentrated under reduced pressure. The crude residue thus obtained was partitioned between EtOAc [150 mL] and water [50 mL]. Organic layer was separated, dried over sodium sulphate and concentrated under reduced pressure to afford 2-(4-phenoxypiperidin-1-yl)aniline (5.1 g, 74%) as brown solid. This compound was used in the next step without further purification.

Step 3. To an ice cooled solution of 4-(N,N-dimethylsulfamoyl)benzoic acid (394 mg, 1.316 mmol, 1 eq) in DMF (3.0 ml), DIPEA (1.4 ml, 7.895 mmol, 6 eq) was added under nitrogen atmosphere. Afterwards, EDC (454 mg, 2.368 mmol, 1.8 eq) and HOBT (322 mg, 2.368 mmol, 1.8 eq) was added to it and stirred for 20 mins. Then a solution of 2-(4-phenoxypiperidin-1-yl)aniline (350 mg, 1.3 mmol, 1 eq) in DMF (2.0 ml) was added to it drop wise and stirred overnight at room temperature. After completion [Monitored with TLC, Mobile Phase 20% EtOAc-Hexane, Rf-0.3] reaction mixture was diluted with ice water [100 mL] and extracted with EtOAc [75 mL×2]. Organic layer was separated, dried over sodium sulphate and concentrated under reduced pressure. Resultant crude was purified by Combiflash column chromatography using 5-10% ethyl acetate in hexane as eluting solvent to 4-(N,N-dimethylsulfamoyl)-N-(2-(4-phenoxypiperidin-1-yl)phenyl)benzamide (520 mg, 83%) as light yellow solid compound.

Step 4. To a solution of 4-(N,N-dimethylsulfamoyl)-N-(2-(4-phenoxypiperidin-1-yl)phenyl)benzamide (100 mg, 0.209 mmol) in DMF (2.0 ml), NaH (20 mg, 0.835 mmol) was added in ice cool condition under nitrogen atmosphere and stirred for 30 mins. Afterwards 1-bromo-2-methoxyethane (CAS: 6482-24-2) (87 mg, 0.626 mmol, 3 eq) was added to it. Again the reaction mixture was stirred for another 2 hrs.

TLC (20% EA in Hexane) confirmed complete consumption of starting material to new polar spot. Reaction was quenched with ice water and partitioned between water and EtOAc. Organic layer was diluted with water (25 mL×3) to remove DMF. Then the organic part was dried over anhydrous sodium sulphate and concentrated under reduced pressure. Crude was purified using 14% EA in Hexane by Combiflash column chromatography and finally the crude was purified by RP Preparative HPLC to afford 4-(N,N-dimethylsulfamoyl)-N-(2-methoxyethyl)-N-(2-(4-phenoxypiperidin-1-yl)phenyl)benzamide (65 mg, 64%) as white solid. RP Preparative HPLC method: Method-4

Example 4

The title compound was prepared analogously to Example 3 utilizing propyl bromide (CAS: 106-94-5) in step 4. Crude product was purified by Combiflash column [eluent 10-15% EtOAc-Hexane] to provide 4-(N,N-dimethylsulfamoyl)-N-(2-(4-phenoxypiperidin-1-yl)phenyl)-N-propylbenzamide (70 mg, 65%) as white solid.

Example 5

The title compound was prepared following Example-1, step-4 using 2-(4-phenoxypiperidin-1-yl)aniline.

Final step, to a stirred solution of 4-(N,N-dimethylsulfamoyl)-N-(2-(4-phenoxypiperidin-1-yl)phenyl)benzamide (100 mg, 0.21 mmol, 1 eq) in toluene (5 mL) was added $Cs_2CO_3$ (68 mg, 0.21 mmol, 1 eq), copper acetate (38 mg, 0.209 mmol, 1 eq), cyclopropylboronic acid (53 mg, 0.626 mmol, 3 eq), pyridine (0.049 ml) and resultant reaction mixture was allowed to stir at 140° C. for 48 h under oxygen atmosphere. After LCMS analysis reaction mixture was quenched with water (50 mL) and extracted by ethyl acetate (50 ml×2). Combine organic layer was washed by brine solution (50 mL) and dried over sodium sulphate and concentrated under reduced pressure. Crude compound was purified by column chromatography over silica gel (100-200), under 40-50% EtOAc/Hexane to provide N-cyclopropyl-4-(N,N-dimethylsulfamoyl)-N-(2-(4-phenoxypiperidin-1-yl)phenyl)benzamide (15 mg, 14%) as off white solid. RP Preparative HPLC method: Method-3

Example 6

Step 1. To a stirred solution of 4-phenoxypiperidine (5.0 g, 211 mmol, 1 eq) in ACN (50 mL) was added $K_2CO_3$ (9.82 g, 71.09 mmol, 3 eq) followed by the addition of 1-fluoro-2-nitrobenzene (6.69 g, 47.39 mmol, 2 eq). The reaction mixture was stirred at 80° C. temperature for 4 h. After completion [Monitored with TLC, Mobile Phase 5% EtOAc-Hexane, Rf-0.5], reaction mixture was concentrated and diluted with water [100 mL] and extracted with EtOAc [75 mL×2]. Organic layer was separated, dried over sodium sulphate and concentrated under reduced pressure. Resultant crude was purified by Combiflash column chromatography using 0-2% ethyl acetate in hexane as eluting solvent to afford 1-(2-nitrophenyl)-4-phenoxypiperidine (6.8 mg, 97%) as pale yellow liquid.

Step 2. To a stirred solution 1-(2-nitrophenyl)-4-phenoxypiperidine (6.8 g, 22.81 mmol, 1 eq) in EtOH (70 mL) was added 10% Pd—C (7.6 g) under nitrogen atmosphere. Then the reaction was stirred at RT for 2 h. After completion [Monitored with TLC, Mobile Phase:20% EtOAc-Hexane, Rf-0.4] insoluble part was filtered through glass sintered and filtrate part was concentrated under reduced pressure. The crude residue thus obtained was partitioned between EtOAc [150 mL] and water [50 mL]. Organic layer was separated, dried over sodium sulphate and concentrated under reduced pressure to afford 2-(4-phenoxypiperidin-1-yl) aniline (5.1 g, 74%) as brown solid. This compound was used in the next step without further purification.

Step-3. To a stirred solution of 2-(4-phenoxypiperidin-1-yl)aniline (100 mg, 0.37 mmol, 1.0 eq) in pyridine (2 mL) was added 4-(ethylsulfonyl)benzenesulfonyl chloride (CAS: 1099632-50-4) (100 mg, 0.37 mmol, 1.0 eq) and allowed to stir at room temperature for 1 h. After LC-MS analysis reaction mixture was concentrated under reduced pressure. Crude residue thus obtained was purified through a Combiflash column [eluent 25-30% EtOAc-Hexane] to afford 4-(ethylsulfonyl)-N-(2-(4-phenoxypiperidin-1-yl) phenyl) benzenesulfonamide (85 mg, 46%) as white solid.

Example 7

Step-1. To a stirred solution of commercially available 1-chloro-2-fluoro-3-nitrobenzene (263.0 mg, 1.5 mmol) in ACN (5 mL) was added $K_2CO_3$ ((1 g, 7.5 mmol, 5 eq) followed by the addition of 3-(piperidin-4-yloxy) pyridine (376.4 mg, 1.5 mmol, 1 eq). The reaction mixture was stirred at 80° C. temperature for 16 h. After completion [Monitored with TLC, Mobile Phase 5% EtOAc-Hexane, Rf-0.4] reaction mixture was diluted with water [200 mL] and extracted with EtOAc [50 mL×2]. Organic layer was separated, dried over sodium sulphate and concentrated under reduced pressure. Resultant crude was purified by Combiflash column chromatography using 0-10% ethyl acetate in hexane as eluting solvent to afford 3-((1-(2-chloro-6-nitrophenyl)piperidin-4-yl)oxy)pyridine as yellow gummy solid (294 mg, 59%).

Step 2. To a stirred solution of 3-((1-(2-chloro-6-nitrophenyl) piperidin-4-yl) oxy) pyridine (240 mg, 0.72 mmol, 1 eq) in 1, 4-dioxane (6 mL) was added $NH_4Cl$ (288 mg, 5.4 mmol, 7.5 eq) in $H_2O$ (2 mL). Then Zn dust (352 mg, 5.4 mmol, 7.5 eq) was added to the reaction mixture at ice-cold condition, and the reaction was stirred at RT for 2 h. After completion [Monitored with TLC, Mobile Phase: 10% EtOAc-Hexane, Rf-0.2] insoluble part was filtered through glass sintered and filtrate part was concentrated under reduced pressure. The crude residue thus obtained was partitioned between EtOAc [100 mL] and water [60 mL]. Organic layer was separated, dried over sodium sulphate and concentrated under reduced pressure and thus crude was obtained purified by column chromatography using 0-10% ethyl acetate in hexane as eluting solvent to provide 3-chloro-2-(4-(pyridin-3-yloxy) piperidin-1-yl) aniline as an off-white solid (200 mg, 91%).

Step 3. To a stirred solution of 3-chloro-2-(4-(pyridin-3-yloxy) piperidin-1-yl) aniline (61 mg, 0.2 mmol, 1 eq) in dichloromethane (2 mL) was added $Et_3N$ (0.05 mL, 0.5 mmol, 2 eq). Then 4-(Dimethylsulfamoyl) benzene-1-sulfonyl chloride (CAS: 677782-39-7) (68.4 mg, 0.24 mmol, 1.2 eq) was added to the reaction mixture at ice-cold condition, and the reaction was stirred at RT for 12 h. After completion [Monitored with TLC, Mobile Phase: 30% EtOAc-Hexane, Rf-0.4] reaction mixture was quenched with saturated $NaHCO_3$ and extracted in DCM [15 mL×2]. Combined organic layer was dried over anhydrous $Na_2SO_4$, solvent was removed under vacuum and purified by silica gel Combiflash column chromatography using 0-10% ethyl acetate/hexane as eluting solvent to get pure afford N1-(3-chloro-2-(4-(pyridin-3-yloxy)piperidin-1-yl)phenyl)-N4, N4-dimethylbenzene-1,4-disulfonamide as off white solid (30 mg, 27%).

Example 8

The title compound was prepared analogously to Example 7 utilizing 2, 3-diflouro-nitro-benzene in step 1.

Final step, to a stirred solution of 3-fluoro-2-(4-(pyridin-2-yloxy) piperidin-1-yl) aniline (200 mg, 0.69 mmol, 1.0 eq) in 7 ml DCM was added TEA (210 mg, 2.08 mmol, 3.0 eq) followed by the addition of 4-(N, N-dimethylsulfamoyl) benzene sulfonyl chloride (275 mg, 0.97 mmol, 1.4 eq) and catalytic amount of DMAP and resultant reaction mixture was allowed to stir at room temperature for 16 h. After completion of the reaction [Monitored with TLC, Mobile Phase 20% EtOAc-Hexane, Rf-0.4], it was diluted with 50 mL DCM and washed with 80 mL water. The organic layer was dried over sodium sulphate and concentrated under reduced pressure. The crude material was purified by Combiflash column chromatography to afford $N^1$-(3-fluoro-2-(4-(pyridin-2-yloxy) piperidin-1-yl)phenyl)-$N^4$,$N^4$-dimethylbenzene-1,4-disulfonamide as white solid (80 mg, 21%).

Example 9

The title compound was prepared analogously to Example 3 utilizing methyl iodide in step 4 and 4-(pyridin-2-yloxy) piperidine in step 1. The crude was purified by RP HPLC to obtain 4-(N,N-dimethylsulfamoyl)-N-(3-fluoro-2-(4-(pyridin-2-yloxy)piperidin-1-yl)phenyl)-N-methylbenzamide as white solid (60 mg, 65%). RP Preparative HPLC method: Method-4

Example 10

Final step, to a stirred solution of 3-fluoro-2-(4-(pyridin-2-yloxy)piperidin-1-yl)aniline (100 mg, 0.35 mmol, 1.0 eq) in Pyridine (7 mL) at 0° C. was added 4-(trifluoromethyl) benzenesulfonyl chloride (102 mg, 0.42 mmol, 1.2 eq) and the stirring was continued for 1 h. After completion [Monitored by LC-MS]reaction mixture was concentrated under red reduced pressure, resultant crude was passed through a flash column [10-15% EtOAc-Hexane eluting solvent] to afford desired compound N-(3-fluoro-2-(4-(pyridin-2-yloxy) piperidin-1-yl)phenyl)-4-(trifluoromethyl)benzenesulfonamide as off white solid (80 mg, 46%).

Example 11

Step 1. To a stirred solution of 4-(N,N-dimethylsulfamoyl)benzoic acid (320 mg, 1.4 mmol, 1.0 eq) in DMF (7 mL) at 0° C., EDC·HCl (481 mg, 2.51 mmol, 1.8 eq) and HOBT (340 mg, 2.5 mmol, 1.8 eq) were added. The solution was kept at 0° C. and DIPEA (0.73 mL, 4.18 mmol, 3.0 eq) was added on it. Then 3-fluoro-2-(4-(pyridin-2-yloxy)piperidin-1-yl)aniline (400 mg, 1.4 mmol, 1.0 eq) was added to the reaction mixture. Reaction was continued for 16 h from 0° C. to room temperature. After completion of the reaction [Monitored with TLC, Mobile Phase 30% EtOAc-Hexane, Rf-0.4], the reaction was diluted with 80 mL DCM and washed with water (40 mL) and saturated brine (40 mL). Then the organic layer was separated and dried over sodium sulphate then concentrated under reduced pressure. The crude residue was purified by column chromatography using Silica gel [100-200] under gradient elution of 20-25% EtOAc-Hexane to afford 4-(N,N-dimethylsulfamoyl)-N-(3-fluoro-2-(4-(pyridin-2-yloxy)piperidin-1-yl)phenyl)benzamide as white solid (450 mg, 75%)

Step 2. To a stirred solution of 4-(N,N-dimethylsulfamoyl)-N-(3-fluoro-2-(4-(pyridin-2-yloxy)piperidin-1-yl) phenyl)benzamide (250 mg, 0.50 mmol, 1.0 eq) in THF (15 mL) at ice-cool temperature 60% NaH (48 mg, 2.00 mmol, 1.5 eq) was added and stirring was continued from 0° C. to room temperature. To this solution 2-Iodopropane (0.25 mL, 2.51 mmol, 1.1 eq) was added. The reaction mixture was heated at 70° C. and continued for 16 h. After completion of the reaction ice-water was added and extracted with ethyl acetate. The organic part was separated, dried over sodium sulphate and concentrated under reduced pressure. The crude was purified by column chromatography using Silica gel [100-200] under gradient elution of 20-25% EtOAc-Hexane to afford desired product 4-(N,N-dimethylsulfamoyl)-N-(3-fluoro-2-(4-(pyridin-2-yloxy)piperidin-1-yl) phenyl)-N-isopropylbenzamide as white solid (110 mg, 40%).

Example 12

The title compound was prepared analogously to Example 2 utilizing 3-fluoro-2-(4-(pyridin-2-yloxy)piperidin-1-yl) aniline in step 3. The crude residue was purified by column chromatography using Silica gel [100-200] under gradient elution of 10-20% EtOAc-Hexane to get desired product N-cyclobutyl-4-(N,N-dimethylsulfamoyl)-N-(3-fluoro-2-(4-(pyridin-2-yloxy)piperidin-1-yl)phenyl)benzamide as white solid (180 mg, 80%).

Example 13

The title compound was prepared analogously to Example 7 utilizing 2-flouro-5-chloro-nitro-benzene in step 1.

Final step, To a stirred solution of 5-chloro-2-(4-(pyridin-2-yloxy)piperidin-1-yl)aniline (150 mg, 0.49 mmol, 1.0 eq) in pyridine (2 mL) was added 4-(N,N-dimethylsulfamoyl) benzenesulfonyl chloride (CAS: 677782-39-7) (196 mg, 0.69 mmol, 1.4 eq) and allowed to stir at room temperature for 1 h. After LC-MS analysis reaction mixture was concentrated under reduced pressure. Crude residue thus obtained was initially passed through a Combiflash column [eluent 20-25% EtOAc-Hexane]. Resultant impure compound was further purified by RP Preparative HPLC to provide $N^1$-(5-chloro-2-(4-(pyridin-2-yloxy) piperidin-1-yl) phenyl)-$N^4$,$N^4$-dimethylbenzene-1,4-disulfonamide (20 mg, 8%) as white solid. RP Preparative HPLC method: Method-1

Example 14

The title compound was prepared analogously to Example 7 utilizing 2-flouro-5-methyl-nitro-benzene in step 1. Final compound was prepared analogously to Example 17 utilizing 4-(N,N-dimethylsulfamoyl)benzenesulfonyl chloride (CAS: 677782-39-7) and crude compound passed through a Combiflash column [eluent 20-25% EtOAc-Hexane] to afford $N^1$, $N^1$-dimethyl-$N^4$-(5-methyl-2-(4-(pyridin-2-yloxy) piperidin-1-yl) phenyl) benzene-1, 4-disulfonamide (50 mg, 22%) as off white solid.

Example 15

The title compound was prepared analogously to Example 8 utilizing 4-(ethylsulfonyl)benzenesulfonyl chloride in step 3.

Final step, to a stirred solution of 3-fluoro-2-(4-(pyridin-2-yloxy)piperidin-1-yl)aniline (100 mg, 0.37 mmol, 1.0 eq) in pyridine (2 mL) was added 4-(ethylsulfonyl)benzenesulfonyl chloride (CAS: 1099632-50-4) (86 mg, 0.29 mmol, 0.8 eq) and allowed to stir at room temperature for 1 h. After LC-MS analysis reaction mixture was concentrated under reduced pressure. Crude residue thus obtained was initially passed through a Combiflash column [eluent 20-25% EtOAc-Hexane]. Resultant impure compound was further purified by RP Preparative HPLC to provide 4-(ethylsulfonyl)-N-(3-fluoro-2-(4-(pyridin-2-yloxy)piperidin-1-yl)phenyl)benzenesulfonamide (35 mg, 18%) as white solid. RP Preparative HPLC method: Method-4

Example 16

The title compound was prepared analogously to Example 1 utilizing 2-flouro-5-methylnitrobenzene in step 1. Highlight any specific differences in the procedure compared to Example 1. Final compound was purified by column chromatography through a Combiflash column [eluent 20-25% EtOAc-Hexane] to afford N-cyclopentyl-4-(N, N-dimethylsulfamoyl)-N-(5-methyl-2-(4-(pyridin-2-yloxy)piperidin-1-yl)phenyl)benzamide (50 mg, 31%) as white solid.

Example 17

Step 1. To a stirred solution of tert-butyl piperazine-1-carboxylate (500 mg, 2.69 mmol, 1 eq) in ACN (10 mL) was added $K_2CO_3$ (1.1 g, 8.06 mmol, 3 eq) followed by the addition of 1-fluoro-2-nitrobenzene (379 mg, 2.69 mmol, 1 eq). The reaction mixture was stirred at 80° C. temperature for 4 h. After completion [Monitored with TLC, Mobile Phase 10% EtOAc-Hexane, Rf-0.5] reaction mixture was diluted with water [200 mL] and extracted with EtOAc [50 mL×2]. Organic layer was separated, dried over sodium sulphate and concentrated under reduced pressure. Resultant crude was purified by Combiflash column chromatography using 0-10% ethyl acetate in hexane as eluting solvent to afford tert-butyl 4-(2-nitrophenyl) piperazine-1-carboxylate (720 mg, 87%) as pale yellow liquid.

Step 2. To a stirred solution tert-butyl 4-(2-nitrophenyl) piperazine-1-carboxylate (620 mg, 2.01 mmol, 1 eq) in 1, 4-dioxane (9 mL) was added $NH_4Cl$ (754 mg, 14.12 mmol, 7 eq) in $H_2O$ (3 mL). Then Zn dust (918 mg, 14.12 mmol, 7 eq) was added to the reaction mixture at ice-cold condition, and the reaction was stirred at RT for 2 h. After completion [Monitored with TLC, Mobile Phase: 10% EtOAc-Hexane, Rf-0.2] insoluble part was filtered through glass sintered and filtrate part was concentrated under reduced pressure. The crude residue thus obtained was partitioned between EtOAc [100 mL] and water [60 mL]. Organic layer was separated, dried over sodium sulphate and concentrated under reduced pressure to afford tert-butyl 4-(2-aminophenyl) piperazine-1-carboxylate (500 mg, 89%) as brown liquid. This compound was used in the next step without further purification.

Step 3. To a stirred solution of tert-butyl 4-(2-aminophenyl) piperazine-1-carboxylate (150 mg, 0.54 mmol, 1.0 eq) in pyridine (2 mL) was added 4-(Trifluoromethyl)benzenesulfonyl chloride (CAS: 2991-42-6) (132 mg, 0.54 mmol, 1.0 eq) and allowed to stir at room temperature for 1 h. After LC-MS analysis reaction mixture was concentrated under reduced pressure. Crude residue thus obtained was initially passed through a Combiflash column [eluent 15-20% EtOAc-Hexane]. Resultant impure compound was further purified by RP Preparative HPLC to provide tert-butyl 4-(2-((4 (trifluoromethyl) phenyl) sulfonamido) phenyl) piperazine-1-carboxylate (80 mg, 30%) as white solid. RP Preparative HPLC method: Method-4

Example 18

The title compound was prepared analogously to Example 17 utilizing 2-fluoro-4-methylbenzenesulfonyl chloride (CAS: 518070-29-6) in step 3 and the crude was purified by RP Preparative HPLC (170 mg, 70%). RP Preparative HPLC method: Method-4

Example 19

The title compound was prepared analogously to Example 17 utilizing 3-fluoro-4-methylbenzenesulfonyl chloride (CAS: 90260-13-2) in step 3 and the crude was purified by RP Preparative HPLC (170 mg, 70%). RP Preparative HPLC method: Method-4

Example 20

The title compound was prepared analogously to Example 17 utilizing 2,5-dimethylbenzenesulfonyl chloride (CAS: 19040-62-1) in step 3 and the crude was purified by Combiflash column [eluent 10-20% EtOAc-Hexaneto afford tert-butyl 4-(2-((2,5-dimethylphenyl)sulfonamido)phenyl)piperazine-1-carboxylate (127 mg, 53%).

Example 21

The title compound was prepared analogously to Example 17 utilizing 4-(trifluoromethoxy) benzenesulfonyl chloride (CAS: 94108-56-2) in step 3 and the crude was purified by RP Preparative HPLC (130 mg, 48%). RP Preparative HPLC method: Method-4

Example 22

Step 1. To a stirred solution of 1-fluoro-3-methyl-2-nitrobenzene (1.6 g, 10.32 mmol, 1 eq) in DMF (10 mL) was added $K_2CO_3$ (2.8 g, 20.64 mmol, 2 eq), tert-butyl piperazine-1-carboxylate (1.9 g, 10.32 mmol, 1 eq) and resultant reaction mixture was allowed to stir at RT for 16 h. After completion [Monitored with TLC, Mobile Phase 10% EtOAc-Hexane, and Rf-0.3] reaction mixture was quenched with water (100 ml) and extracted by ethyl acetate (100 ml×2). Combine organic layer was washed by brine solution (50 ml), dried over sodium sulphate and concentrated under reduced pressure. The crude residue thus obtained was purified by column chromatography over silica gel (100-200) using 2-5% EtOAc/Hexane as eluting solvent to afford tert-butyl 4-(3-methyl-2-nitrophenyl) piperazine-1-carboxylate (2 g, 60%) as light brown liquid.

Step 2. To a stirred solution of tert-butyl 4-(3-methyl-2-nitrophenyl) piperazine-1-carboxylate (1.4 g, 4.36 mmol, 1 eq) in ethanol (10 mL) was added 10% Pd—C [50% moisture] (140 mg) and resultant reaction mixture was allowed to stir at room temperature for 16 h under H2 balloon pressure. After completion [Monitored with TLC, Mobile Phase 20% EtOAc-Hexane, and Rf-0.5] reaction mixture was filtered through celite bed and celite bed was further washed with EtOAc [100 mL]. Filtrate was concentrated under reduced pressure to provide crude tert-butyl 4-(2-amino-3-methylphenyl) piperazine-1-carboxylate (1 g, 78%) as brown solid.

Step 3. To a stirred solution of tert-butyl 4-(2-amino-3-methylphenyl) piperazine-1-carboxylate (200 mg, 0.69 mmol, 1 eq) in DCM (5 mL) was added TEA (173 mg, 1.72 mmol, 2 eq), 4-methylbenzenesulfonyl chloride (196 mg, 1.03 mmol, 1.5 eq) and resultant reaction mixture was allowed to stir at RT for 16 h. After completion [monitored with LC-MS] reaction mixture was diluted with water (100 mL) and extracted by EtOAc (100 mL×2). Combined organic layer was washed by brine solution (50 mL) dried over sodium sulphate and concentrated under reduced pressure. Crude residue was purified by column chromatography over silica gel (100-200) using 5% EtOAc/Hexane eluting solvent then re purified by prep HPLC to afford tert-butyl 4-(3-methyl-2-((4-methylphenyl) sulfonamido)phenyl)piperazine-1-carboxylate (100 mg, 33%) as off white solid. RP Preparative HPLC method: Method-4

Example 23

The title compound was prepared analogously to Example 17 utilizing 4-cyclopropylbenzene-1-sulfonyl chloride (CAS: 167404-32-2) in step 3 and the crude was purified by RP Preparative HPLC to afford tert-butyl 4-(2-((4-cyclopropylphenyl)sulfonamido)phenyl)piperazine-1-carboxylate (93 mg, 56%). RP Preparative HPLC method: Method-1

Example 24

Step-1. To a stirred solution of 1-fluoro-2-nitrobenzene (200 mg, 1.42 mmol, 1 eq) in ACN (5 mL), $K_2CO_3$ (978 mg, 7.09 mmol, 5 eq) and azepane (318 mg, 149 mmol, 1 eq) was added and the reaction mixture was stirred for 3 hours at 90° C. After completion [Monitored with TLC, Mobile Phase 5% EtOAc-Hexane, Rf-0.5] reaction mixture was diluted with water [50 mL] and extracted with EtOAc [15 mL×2]. Organic layer was separated, dried over sodium sulphate and concentrated under reduced pressure. Resultant crude was purified by Combiflash column chromatography using 0-10% ethyl acetate in hexane as eluting solvent to afford 1-(2-nitrophenyl)azocane (300 mg, 90%) as yellow solid.

Step-2. To a stirred and degassed solution of 1-(2-nitrophenyl)azocane (325 mg, 1.70 mmol, 1 eq) in ethanol (5 mL) was added 10% Pd—C (300 mg) and allowed to stir for 12 h under hydrogen atmosphere. After completion [Monitored with TLC, Mobile Phase 20% EtOAc-Hexane, and Rf-0.4] heterogeneous reaction mixture was filtered through celite bed and celite bed was further washed with ethyl acetate (25 ml). Resultant filtrate was concentrated under reduced pressure to afford crude 2-(azocan-1-yl) aniline (300 mg, 89%) as brown sticky solid.

Step 3. To a stirred solution of 2-(azocan-1-yl)aniline (300 mg, 1.1 mmol, 1 eq) in dichloromethane (2 mL) was added DIPEA (0.6 mL, 3.7 mmol, 3.0 eq). Then after 15 min of stirring 4-(N,N-dimethylsulfamoyl)benzenesulfonyl chloride (CAS: 677782-39-7) (303 mg, 1.48 mmol, 1 eq) was added to the reaction mixture at ice-cold condition, and the reaction was stirred at 70° C. for 3 h. After completion [Monitored with TLC, Mobile Phase: 30% EtOAc-Hexane, Rf-0.4] reaction mixture was diluted with water and extracted in ethyl acetate [10 mL×2]. Combined organic layer was dried over anhydrous $Na_2SO_4$, solvent was removed under vacuum and purified by silica gel Combiflash column chromatography using 0-10% ethyl acetate/hexane as eluting solvent to get pure afford N1-(2-(azocan-1-yl)phenyl)-N4,N4-dimethylbenzene-1,4-disulfonamide as yellow solid (10 mg, 3%). RP Preparative HPLC method: Method-4

Example 25

The title compound was prepared analogously to Example 24 utilizing 3-benzyloxypiperdine in step 1.

Step 2. To a stirred solution of 3-(benzyloxy)-1-(2-nitrophenyl)piperidine (270 mg, 0.86 mmol, 1 eq) in Dioxane (10 mL) and water (3 ml) was added $NH_4Cl$ (346 mg, 6.49 mmol, 7.5 eq) followed by addition of Zn (424 mg, 6.49 mmol, 7.5 eq) maintaining an external temperature at 5-10° C. Then resultant heterogeneous reaction mixture was allowed to stir at room temperature for 16 h. After completion [monitored by TLC, Mobile Phase: 30% EtOAc/Hexane, Rf-0.3] reaction mixture was quenched with water (100 mL) and extracted by ethyl acetate (100 mL×2). Combine organic layer was washed by brine solution (50 mL), dried over sodium sulphate and concentrated under reduced pressure to provide crude 2-(3-(benzyloxy) piperidin-1-yl) aniline (240 mg, 98%) as light brown solid.

Step 3. The title compound N1-(2-(3-(benzyloxy)piperidin-1-yl)phenyl)-N4,N4-dimethylbenzene-1,4-disulfonamid was prepared by following Example-24, step-3 using 2-(3-(benzyloxy) piperidin-1-yl) aniline and crude product was purified by column chromatography using silica gel (100-200) as absorbent under gradient elution of 20% EtOAc/Hexane and then re-purified by Prep-HPLC purification to afford N1-(2-(3-(benzyloxy) piperidin-1-yl) phenyl)-N4, N4-dimethylbenzene-1,4-disulfonamide (120 mg, 32%) as off white solid. RP Preparative HPLC method: Method-1

Example 26 and Example 27

50 mg of racemic compound was subjected to chiral resolution SFC and obtained one enantiomer with Rt 12.24 min as Peak-1 (13 mg) and another enantiomer with Rt 15.49 min as peak-2 (10 mg) as off white solids [absolute stereochemistry not confirmed for the enantiomers]. Enantiomeric separation method: Column name—CHIRALCEL OD-H (250×20 mm) 5u; Flow rate—18 ml/min; Mobile phase—HEXANE/ETOH/IPAMINE—85/15/0.1; Solubility—CAN; Wave length—220 nm; Run time—20 min Example 28

The title compound was prepared analogously to Example 24 utilizing 3-phenoxypiperdine in step 1.

Step 2. To a stirred solution of 1-(2-nitrophenyl)-3-phenoxypiperidine (450 mg, 1.51 mmol, 1 eq) in 1, 4-dioxane (9 mL) was added $NH_4Cl$ (571 mg, 10.57 mmol, 7 eq) in $H_2O$ (3 mL). Then Zn dust (687 mg, 10.57 mmol, 7 eq) was added to the reaction mixture at ice-cold condition, and the reaction was stirred at RT for 2 h. After completion [Monitored with TLC, Mobile Phase: 10% EtOAc-Hexane, Rf-0.2] insoluble part was filtered through glass sintered and filtrate part was concentrated under reduced pressure. The crude residue thus obtained was partitioned between EtOAc [100 mL] and water [60 mL]. Organic layer was separated, dried over sodium sulphate and concentrated under reduced pressure to afford 2-(3-phenoxypiperidin-1-yl) aniline (400 mg, 98%) as brown liquid. This compound was used in the next step without further purification.

Step 3. To a stirred solution of 2-(3-phenoxypiperidine-1-yl)aniline (250 mg, 0.93 mmol, 1.0 eq) in DCM (5 mL) were added DIPEA (0.48 mL, 2.8 mmol, 3.0 eq) and 4-(N,N-dimethylsulfamoyl)benzenesulfonyl chloride (CAS: 677782-39-7) (290 mg, 1.02 mmol, 1.1 eq) under nitrogen atmosphere. The reaction was stirred at room temperature 12 hr. The progress of the reaction was monitored by LCMS and TLC [Mobile Phase: 10% EtOAc-Hexane, Rf-0.2] which showed unreacted starting material along with desired product. Reaction mixture was diluted with water [20 mL] and extracted with DCM [50 mL×2]. Organic layer was separated, dried over sodium sulphate and concentrated under reduced pressure. Resultant crude was purified by Combiflash column chromatography using 0-10% ethyl acetate in hexane as eluting solvent to afford $N^1$,$N^1$-dimethyl-$N^4$-(2-(3-phenoxypiperidine-1yl)benzene-1,4-disulfonamide as off white solid then it was re purified using prep HPLC to get desired racemic compound (35 mg, 7%). RP Preparative HPLC method: Method-4

Example 29 and Example 30

25 mg of racemic compound was subjected to chiral resolution SFC and obtained one enantiomer with Rt 15.30 min as Peak-1 (6.96 mg) and another enantiomer with Rt 19.29 min as peak-2 (5.11 mg) as brown sticky solids [absolute stereochemistry of enantiomers not confirmed]. Enantiomeric separation method: Column name—CHIRALCEL OD-H (250×20 mm) 5u; Flow rate—18 ml/min; Mobile phase—HEXANE/ETOH—85/15; Solubility—MEOH; Wave length—220 nm; Run time—26 min Example 31

The title compound was prepared analogously to Example 24 utilizing 2-cyclopropylmorpholine in step 1.

Final step, to a stirred solution of 2-(2-cyclopropylmorpholino)aniline (125 mg, 0.57 mmol, 1.0 eq) in 10 ml DCM was added triethyl amine (0.2 ml, 1.43 mmol, 2.5 eq) followed by the addition of 4-(N, N-dimethylsulfamoyl) benzenesulfonyl chloride (141 mg, 0.5 mmol, 0.87 eq) and catalytic amount of DMAP (2 mg). Resultant reaction mixture was allowed to stir at RT for 16 h. After LC-MS analysis resultant reaction mixture was concentrated under reduced pressure. The crude residue was purified by Combiflash column chromatography using 0-10% ethyl acetate in hexane as eluting to afford $N^1$-(2-(2-cyclopropylmorpholino) phenyl)-$N^4$, $N^4$-dimethylbenzene-1,4-disulfonamide as white solid (60 mg, 22%).

Example 32

The title compound was prepared analogously to Example 24 utilizing 2-cyclobutlymorpholine in step 1.

Final step, to a stirred solution of 2-(2-cyclobutylmorpholino) aniline (90 mg, 0.39 mmol, 1.0 eq) in DCM (2.0 mL), DIPEA (0.2 ml, 1.164 mmol, 3 eq) was added followed by 4-(N,N-dimethylsulfamoyl)benzenesulfonyl chloride (CAS: 677782-39-7) (165 mg, 0.58 mmol, 1.5 eq) and allowed to stir at room temperature for 1 h. After LC-MS analysis reaction mixture was concentrated under reduced pressure. Crude residue thus obtained was passed through a Combiflash column [eluent 20-25% EtOAc-Hexane to provide N-(2-(2-cyclobutylmorpholino) phenyl) benzenesulfonamide (70 mg, 38%) as white solid.

Example 33

Step-1. To a stirred solution of 2-(prop-2-yn-1-yl) morphine hydrochloride (100 mg, 0.62 mmol, 1.0 eq) and 1-fluoro-2-nitrobenzene (87 mg, 0.62 mmol, 1.0 eq) in DMSO (4 mL) at room temperature was added DIPEA (0.325 ml, 1.86 mmol, 3.0 eq). Then reaction mixture was heated at 120° C. for 6 h. After completion [Monitored with TLC, Mobile Phase 30% EtOAc-Hexane, Rf-0.5] reaction mixture was quenched with 20 ml of cold water and extracted with 70 mL ethyl acetate. The organic part was separated, dried over sodium sulphate and concentrated under reduced pressure. Resultant crude was purified by flash column chromatography using Silica gel (100-200) as absorbent under gradient elution with 15-20% EtOAc-Hexane to afford an orange gummy mass of 4-(2-nitrophenyl)-2-(prop-2-yn-1-yl)morpholine (134 mg, 88%).

Step 2. To a stirred solution of 4-(2-nitrophenyl)-2-(prop-2-yn-1-yl) morpholine (80 mg, 0.33 mmol, 1.0 eq) in 3 mL 1,4-dioxane was added solution of ammonium chloride (87 mg, 1.63 mmol, 5.0 eq) in 1 mL water, zinc powder (106 mg, 1.63 mmol, 5.0 eq) and resultant suspension was allowed to stir at room temperature for 1 h. After completion [Monitored with TLC, Mobile Phase 20% EtOAc-Hexane, Rf-0.4] reaction mixture was passed through a celite bed and filtrate part was concentrated under reduced pressure. Resultant crude was partitioned between EtOAc (100 mL) and water (60 mL). Then organic layer was separated, dried over sodium sulphate and concentrated under reduced pressure to afford desired product 2-(2-(prop-2-yn-1-yl) morpholino) aniline as brown gummy liquid (60 mg, 85%).

Step 3. To a stirred solution of 2-(2-(prop-2-yn-1-yl) morpholino) aniline (60 mg, 0.28 mmol, 1.0 eq) in 7 ml Pyridine at 0° C. was added 4-(N, N-dimethylsulfamoyl) benzenesulfonyl chloride (78.56 mg, 0.28 mmol, 1.0 eq) and the stirring was continued for 1 h. After completion [monitored with LC-MS]reaction mixture was concentrated under reduced pressure to remove excess pyridine. Resultant crude was purified by column chromatography using silica gel (100-200) under gradient elution of 10-15% EtOAc-Hexane to afford to afford impure intermediate desired compound. The impure fraction was further purified by Preparative HPLC to afford $N^1$, $N^1$-dimethyl-$N^4$-(2-(2-(prop-2-yn-1-yl) morpholino)phenyl)benzene-1,4-disulfonamide as white solid (70 mg, 54%). RP Preparative HPLC method: Method-4

Example 34

The title compound was prepared analogously to Example 24 utilizing 3-phenoxymethylpiperidine in step 1.

Final step, to a stirred solution of 2-(3-(phenoxymethyl) piperidin-1-yl)aniline (76 mg, 0.27 mmol, 1 eq) in pyridine (2 ml) was added 4-(N, N-dimethylsulfamoyl) benzene sulfonyl chloride (114 mg, 0.40 mmol, 1.5 eq) and stirred for 1 h at RT. After completion [monitored with LC-MS] of starting material reaction mixture was diluted with water (100 ml) and extracted by ethyl acetate (100 mL×2). Combined organic layer was washed by brine solution (50 ml), dried over sodium sulphate and concentrated under reduced pressure. Resultant crude was purified by column chromatography over silica gel (100-200), using 20-25% EtOAc/Hexane as eluting solvent to afford $N^1$,$N^1$-dimethyl-$N^4$-(2-(3-(phenoxymethyl)piperidin-1-yl)phenyl)benzene-1,4-disulfonamide (40 mg, 28%) as off white solid. RP Preparative HPLC method: Method-1

Example 35 and Example 36

25 mg of racemic compound was subjected to chiral resolution SFC and obtained one enantiomer with Rt 24.19 min as Peak-1 (8 mg) and another enantiomer with Rt 28.16 min as peak-2 (7 mg) as off white solids [absolute stereochemistry of enantiomers not confirmed]. Enantiomeric separation method: Column name—CHIRALCEL OD-H (250×20 mm) 5u; Flow rate—18 ml/min; Mobile phase—HEXANE/ETOH/IPAMINE—90/10/0.1; Solubility—MEOH+CAN; Wave length—220 nm; Run time—32 min Example 37

Step 1. To a stirred solution of 4-methyl-4-phenylpiperidine (100 mg, 0.57 mmol, 1 eq) in ACN (10 mL) was added 1,2-difluoro-3-nitrobenzene (90 mg, 0.57 mmol, 1 eq) followed by addition of $K_2CO_3$ (197 mg, 1.43 mmol, 2.5 eq) and the resultant reaction mixture was allowed to stir at 90° C. for 2 h. After completion [monitored by TLC, Mobile phase: 10% EtOAc/Hexane, Rf-0.3] reaction mixture was quenched with water (100 mL) and extracted by ethyl acetate (100 mL×2). Combine organic layer was washed by brine solution (50 mL), dried over sodium sulphate and concentrated under reduced pressure. Crude residue thus obtained was purified by column chromatography over silica gel (100-200) under gradient elution of 8-10% EtOAc/Hexane to afford 1-(2-fluoro-6-nitrophenyl)-4-methyl-4-phenylpiperidine (130 mg, 72%) as light brown liquid.

Step-2. To a stirred solution of 1-(2-fluoro-6-nitrophenyl)-4-methyl-4-phenylpiperidine (130 mg, 0.41 mmol, 1 eq) in 1,4 dioxane (10 mL) and water was added Ammonium chloride (142 mg, 1.03 mmol, 2.5 eq) and Zinc powder (65 mg, 0.413 mmol, 1 eq) maintaining external temperature at 5-10° C. Then reaction mixture was allowed to stir at room temperature for 2 h. After completion [monitored by TLC, Mobile phase: 20% EtOAc/Hexane, Rf-0.3] heterogeneous reaction mixture was passed through a celite bed. Filtrate part was diluted with water [50 mL] and extracted with EtOAc [100 mL×2]. Organic layer was separated, dried over sodium sulphate and concentrated under reduced pressure to afford 3-fluoro-2-(4-methyl-4-phenylpiperidin-1-yl) aniline (90 mg, 77%).

Step 3. To a stirred solution of 3-fluoro-2-(4-methyl-4-phenylpiperidin-1-yl)aniline (90 mg, 0.32 mmol, 1 eq) in pyridine (5 mL) was added 4-(N,N-dimethylsulfamoyl)benzenesulfonyl chloride (134 mg, 0.48 mmol, 1.5 eq) and stirred for 2 hr. After completion [monitored by LC-MS] reaction mixture was diluted with water (100 mL) and extracted by ethyl acetate (100 mL×2). Combine organic layer was washed by brine solution (50 mL), dried over sodium sulphate and concentrated under reduced pressure. The crude residue was purified by column chromatography over silica gel (100-200) using 20% EtOAc/Hexane then re-purified by Prep-HPLC to afford $N^1$-(3-fluoro-2-(4-methyl-4-phenylpiperidin-1-yl) phenyl)-$N^4$,$N^4$-dimethylbenzene-1,4 disulfonamide (25 mg, 15%) as off white solid. RP Preparative HPLC method: Method-3

Example 38

The title compound was prepared analogously to Example 37 utilizing 2-flouro-nitrobenzene in step 1.

Step 3. To a stirred solution of 2-(4-methyl-4-phenylpiperidin-1-yl) aniline (130 mg, 0.49 mmol, 1.0 eq) in DCM (5 mL) was added DIPEA (0.26 ml, 1.47 mmol, 3.0 eq), 4-(N, N-dimethylsulfamoyl) benzenesulfonyl chloride (152 mg, 0.54 mmol, 1.1 eq) and resultant reaction mixture was allowed to stir at RT for 16 h. After LC-MS analysis the reaction mixture was partitioned between EtOAc (100 mL) and water (60 mL). Organic layer was separated, dried over sodium sulphate and concentrated under reduced pressure. Resultant crude was purified by preparative HPLC to afford $N^1$, $N^1$-dimethyl-$N^4$-(2-(4-methyl-4-phenylpiperidin-1-yl) phenyl)benzene-1,4-disulfonamide as white solid (22 mg, 9%). RP Preparative HPLC method: Method-3

Example 39

Step 1 To a cooled solution of tert-butyl 4-(2-nitrophenyl) piperazine-1-carboxylate (1.5 g, 4.88 mmol, 1 eq) in Dioxane (10.0 ml) was added dioxane in HCl [4 (M)] (12.0 ml) was added and the resultant mixture stirred for 2 h. After completion [Monitored with TLC, Mobile Phase 20% EtOAc-Hexane, Rf-0.0] reaction mixture was dried under reduced pressure to remove the excess HCl. The obtained crude was washed with pentane to afford 1-(2-nitrophenyl) piperazine hydrochloride salt (1.17 g, 99%) as yellow solid. To a cooled solution of 1-(2-nitrophenyl)piperazine hydrochloride (300 mg, 1.23 mmol, 1 eq) in DMF (3.0 ml) was added NaH (88.86 mg, 3.70 mmol, 3 eq) followed by phenyl carbonochloridate (231 mg, 1.48 mmol, 1.2 eq). The resultant mixture was stirred for 2 h. After completion [Monitored with TLC, Mobile Phase 40% EtOAc-Hexane, Rf-0.5]

reaction mixture was diluted with water [30 mL] and extracted with EtOAc [60 mL×2]. Organic layer was separated, dried over sodium sulphate and concentrated under reduced pressure. Resultant crude was purified by flash neutral alumina column chromatography using 0-10% ethyl acetate in hexane as eluting solvent to phenyl 4-(2-nitrophenyl)piperazine-1-carboxylate (350 mg, 87%) as yellow solid.

Step 2. To a stirred solution phenyl 4-(2-nitrophenyl) piperazine-1-carboxylate (350 mg, 1.07 mmol, 1 eq) in 1, 4-dioxane (6 mL) was added $NH_4Cl$ (401 mg, 7.49 mmol, 7 eq) in $H_2O$ (2 mL). Then Zn dust (488 mg, 7.49 mmol, 7 eq) was added to the reaction mixture in ice-cold condition, and the resultant mixture was stirred at RT for 2 h. After completion [Monitored with TLC, Mobile Phase:40% EtOAc-Hexane, Rf-0.2] insoluble part was filtered through glass sintered and filtrate part was concentrated under reduced pressure. The crude residue thus obtained was partitioned between EtOAc [150 mL] and water [60 mL]. Organic layer was separated, dried over sodium sulphate and concentrated under reduced pressure to afford phenyl 4-(2-aminophenyl) piperazine-1-carboxylate (310 mg, 98%) as light brown solid. This compound was used in the next step without further purification.

Step-3. To a stirred solution of phenyl 4-(2-aminophenyl) piperazine-1-carboxylate (150 mg, 0.50 mmol, 1.0 eq) in pyridine (2 mL) was added 3,4-dimethylbenzenesulfonyl chloride (CAS: 2905-30-8) (113 mg, 0.55 mmol, 1.1 eq) and allowed to stir at room temperature for 1 h. After LC-MS analysis reaction mixture was concentrated under reduced pressure. Crude residue thus obtained was initially passed through a Combiflash column [eluent 30-35% EtOAc-Hexane]. Resultant impure compound was further purified by RP Preparative HPLC to afford phenyl 4-(2-((3, 4-dimethylphenyl)sulfonamido)phenyl)piperazine-1-carboxylate (84 mg, 34%) as white solid. RP Preparative HPLC method: Method-4

Example 40

Step 1. To a stirred solution of 2-((4-methylpiperidin-4-yl)oxy)pyridine (120 mg, 0.62 mmol, 1.0 eq) in DMF (10 mL) was added $K_2CO_3$ (172.5 mg, 1.25 mmol, 3.0 eq) followed by the addition of 1-fluoro-2-nitrobenzene (88 mg, 0.625 mmol, 1.0 eq). The reaction mixture was stirred at 80° C. temperature for 4 h. After completion [Monitored with TLC, Mobile Phase 10% EtOAc-Hexane, Rf-0.5] reaction mixture was diluted with ice water [50 mL] and extracted with EtOAc [50 mL×2]. Organic layer was separated, dried over sodium sulphate and concentrated under reduced pressure. Resultant crude was purified by Combiflash column chromatography using 0-10% ethyl acetate in hexane as eluting solvent to afford 2-((4-methyl-1-(2-nitrophenyl)piperidin-4-yl)oxy)pyridine (150 mg, 76%) as pale yellow liquid.

Step 2. To a stirred solution of 2-((4-methyl-1-(2-nitrophenyl)piperidin-4-yl)oxy)pyridine (150 mg, 0.48 mmol, 1.0 eq) in 1, 4-dioxane (3 mL) was added $NH_4Cl$ (181 mg, 3.35 mmol, 7 eq) in $H_2O$ (1 mL). Then Zn dust (218 mg, 3.35 mmol, 7 eq) was added to the reaction mixture at ice-cold condition, and the reaction was stirred at RT for 2 h. After completion [Monitored with TLC, Mobile Phase: 10% EtOAc-Hexane, Rf-0.3] insoluble part was filtered through glass sintered and filtrate part was concentrated under reduced pressure. The crude residue thus obtained was partitioned between EtOAc [50 mL] and water [20 mL]. Organic layer was separated, dried over sodium sulphate and concentrated under reduced pressure to afford 2-(4-methyl-4-(pyridin-2-yloxy) piperidin-1-yl)aniline (130 mg, 95%) as brown liquid. This compound was used in the next step without further purification.

Step 3. To a stirred solution of 2-(4-methyl-4-(pyridin-2-yloxy)piperidin-1-yl)aniline (130 mg, 0.46 mmol, 1.0 eq) in pyridine (2 mL) was added 4-(N,N-dimethylsulfamoyl)benzenesulfonyl chloride (CAS: 6777-82-7) (143 mg, 0.50 mmol, 1.1 eq) and allowed to stir at room temperature for 1 h. After LC-MS analysis reaction mixture was concentrated under reduced pressure. Crude residue thus obtained was initially passed through a Combiflash column [eluent 15-20% EtOAc-Hexane]. Resultant impure compound was further purified by RP Preparative HPLC to provide N1,N1-dimethyl-N4-(2-(4-methyl-4-(pyridin-2-yloxy)piperidin-1-yl)phenyl)benzene-1,4-disulfonamide (100 mg, 41%) as white solid. RP Preparative HPLC method: Method-2

Example 41

Step 1. To a cooled solution of tert-butyl 4-(2-nitrophenyl) piperazine-1-carboxylate (1.5 g, 4.88 mmol, 1 eq) in Dioxane (10.0 ml) was added dioxane in HCl [4 (M)] (12.0 mL) and the resultant mixture was stirred for 2 h. After completion of reaction [Monitored with TLC, Mobile Phase 20% EtOAc-Hexane, Rf-0.0] reaction mixture was dried under reduced pressure to remove the excess HCl. The obtained crude was washed with pentane to afford 1-(2-nitrophenyl)piperazine hydrochloride salt (1.17 g, 99%) as yellow solid. To a cooled solution of 1-(2-nitrophenyl) piperazine hydrochloride (500 mg, 2.05 mmol, 1 eq) in DMF (5.0 ml) was added NaH (148 mg, 6.17 mmol, 3 eq) followed by 3,3-dimethylbutanoyl chloride (331 mg, 2.46 mmol, 1.2 eq). The resultant mixture was stirred for 2 h at RT. After completion of reaction [Monitored with TLC, Mobile Phase 40% EtOAc-Hexane, Rf-0.5] the reaction mixture was diluted with water [100 mL] and extracted with EtOAc [70 mL×2]. Organic layer was separated, dried over sodium sulphate and concentrated under reduced pressure. Resultant crude was purified by neutral alumina column chromatography using 0-10% ethyl acetate in hexane as eluting solvent to 3,3-dimethyl-1-(4-(2-nitrophenyl)piperazin-1-yl)butan-1-one (610 mg, 98%) as yellow solid.

Step 2. To a stirred solution 3,3-dimethyl-1-(4-(2-nitrophenyl)piperazin-1-yl)butan-1-one (630 mg, 2.06 mmol, 1 eq) in 1, 4-dioxane (9 mL) was added $NH_4Cl$ (773 mg, 14.45 mmol, 7 eq) in $H_2O$ (3 mL). Then Zn dust (941 mg, 14.45 mmol, 7 eq) was added to the reaction mixture in ice-cold condition, and the resultant mixture was stirred at RT for 2 h. After completion [Monitored with TLC, Mobile Phase: 40% EtOAc-Hexane, Rf-0.2] insoluble part was filtered through glass sintered and filtrate part was concentrated under reduced pressure. The crude residue thus obtained was partitioned between EtOAc [150 mL] and water [60 mL]. Organic layer was separated, dried over sodium sulphate and concentrated under reduced pressure to afford 1-(4-(2-aminophenyl)piperazin-1-yl)-3,3-dimethylbutan-1-one (554 mg, 98%) as light brown solid. This compound was used in the next step without further purification.

Step-3. To a stirred solution of 1-(4-(2-aminophenyl) piperazin-1-yl)-3,3-dimethylbutan-1-one (140 mg, 0.50 mmol, 1.0 eq) in pyridine (2 mL) was added 3,4-dimethylbenzenesulfonyl chloride (CAS: 2905-30-8) (114 mg, 0.56 mmol, 1.1 eq) and allowed to stir at room temperature for 1 h. After LC-MS analysis reaction mixture was concentrated under reduced pressure. Crude residue thus obtained was initially passed through a Combiflash column [eluent 30-35% EtOAc-Hexane]. Resultant impure compound was further purified by RP Preparative HPLC to provide N-(2-(4-(3,3-dimethylbutanoyl)piperazin-1-yl)phenyl)-3,4-dimethylbenzenesulfonamide (70 mg, 32%) as white solid. RP Preparative HPLC method: Method-1

Example 42

The title compound was prepared analogously to Example 41 utilizing 4-triflouromethylbenzenesulfonylchloride (CAS: 2991-42-6) in step 3 and the crude was purified by RP Preparative HPLC to afford N-(2-(4-(3,3-dimethylbutanoyl) piperazin-1-yl)phenyl)-4-(trifluoromethyl)benzenesulfonamide (110 mg, 42%, white solid). RP Preparative HPLC method: Method-1

Example 43

Step 1. To a stirred solution of 2-(piperidin-4-yloxy)-5-(trifluoromethyl) pyridine (300 mg, 1.22 mmol, 1.0 eq) in ACN (5 mL) was added $K_2CO_3$ (580 mg, 4.20 mmol, 3.0 eq) followed by the addition of 1,2-difluoro-3-nitrobenzene (193 mg, 1.22 mmol, 1.0 eq). The reaction mixture was stirred at 80° C. temperature for 4 h. After completion [Monitored with TLC, Mobile Phase 5% EtOAc-Hexane, Rf-0.4] reaction mixture was diluted with water [50 mL] and extracted with EtOAc [50 mL×2]. Organic layer was separated, dried over sodium sulphate and concentrated under reduced pressure. Resultant crude was purified by Combiflash column chromatography using 0-5% ethyl acetate in hexane as eluting solvent to afford 2-((1-(2-fluoro-6-nitrophenyl)piperidin-4-yl)oxy)-5-(trifluoromethyl)pyridine (350 mg, 74%) as pale yellow liquid.

Step 2. To a stirred solution of 2-((1-(2-fluoro-6-nitrophenyl)piperidin-4-yl)oxy)-5-(trifluoromethyl)pyridine (350 mg, 0.90 mmol, 1.0 eq) in 1, 4-dioxane (9 mL) was added $NH_4Cl$ (343 mg, 6.36 mmol, 7 eq) in $H_2O$ (3 mL). Then Zn dust (413 mg, 6.36 mmol, 7 eq) was added to the reaction mixture at ice-cold condition, and the reaction was stirred at RT for 2 h. After completion [Monitored with TLC, Mobile Phase: 10% EtOAc-Hexane, Rf-0.5] insoluble part was filtered through glass sintered and filtrate part was concentrated under reduced pressure. The crude residue thus obtained was partitioned between EtOAc [100 mL] and water [50 mL]. Organic layer was separated, dried over sodium sulphate and concentrated under reduced pressure to afford 3-fluoro-2-(4-((5-(trifluoromethyl)pyridin-2-yl)oxy) piperidin-1-yl)aniline (320 mg, 99%) as brown liquid. This compound was used in the next step without further purification.

Step 3. To a stirred solution of 3-fluoro-2-(4-((5-(trifluoromethyl) pyridin-2-yl)oxy)piperidin-1-yl)aniline (120 mg, 0.33 mmol, 1.0 eq) in pyridine (1 mL) was added 4-(N,N-dimethylsulfamoyl)benzenesulfonyl chloride (CAS: 6777-39-7) (95 mg, 0.33 mmol, 1.0 eq) and allowed to stir at room temperature for 1 h. After LC-MS analysis reaction mixture was concentrated under reduced pressure. Crude residue thus obtained was passed through a Combiflash column [eluent 15-20% EtOAc-Hexane] to afford $N^1$-(3-fluoro-2-(4-((5-(trifluoromethyl)pyridin-2-yl)oxy)piperidin-1-yl) phenyl)-$N^4$,$N^4$-dimethylbenzene-1,4-disulfonamide (80 mg, 39%) as white solid.

Example 44

Step 1. To a stirred solution of 5-chloro-2-(piperidin-4-yloxy) pyridine (217 mg, 1.02 mmol, 1.0 eq) in ACN (8 mL) was added $K_2CO_3$ (421 mg, 3.05 mmol, 3.0 eq) followed by the addition of 1,2-difluoro-3-nitrobenzene (162 mg, 1.02 mmol, 1.0 eq). The reaction mixture was stirred at 80° C. temperature for 4 h. After completion [Monitored with TLC, Mobile Phase 5% EtOAc-Hexane, Rf-0.3] reaction mixture was diluted with water [30 mL] and extracted with EtOAc [50 mL×2]. Organic layer was separated, dried over sodium sulphate and concentrated under reduced pressure. Resultant crude was purified by Combiflash column chromatography using 0-5% ethyl acetate in hexane as eluting solvent to 5-chloro-2-((1-(2-fluoro-6-nitrophenyl)piperidin-4-yl)oxy) pyridine (358 mg, 99%) as pale yellow liquid.

Step 2. To a stirred solution of 5-chloro-2-((1-(2-fluoro-6-nitrophenyl) piperidin-4-yl)oxy)pyridine (358 mg, 1.02 mmol, 1.0 eq) in 1, 4-dioxane (9 mL) was added $NH_4Cl$ (384 mg, 7.12 mmol, 7.0 eq) in $H_2O$ (3 mL). Then Zn dust (463 mg, 7.12 mmol, 7 eq) was added to the reaction mixture at ice-cold condition, and the reaction was stirred at RT for 2 h. After completion [Monitored with TLC, Mobile Phase: 10% EtOAc-Hexane, Rf-0.5] insoluble part was filtered through glass sintered and filtrate part was concentrated under reduced pressure. The crude residue thus obtained was partitioned between EtOAc [50 mL] and water [50 mL]. Organic layer was separated, dried over sodium sulphate and concentrated under reduced pressure to afford 2-(4-((5-chloropyridin-2-yl)oxy)piperidin-1-yl)-3-fluoroaniline (327 mg, 99%) as brown liquid. This compound was used in the next step without further purification.

Step 3. To a stirred solution of 2-(4-((5-chloropyridin-2-yl)oxy)piperidin-1-yl)-3-fluoroaniline (150 mg, 0.46 mmol, 1.0 eq) in pyridine (2 mL) was added 4-(N,N-dimethylsulfamoyl)benzenesulfonyl chloride (CAS: 6777-39-7) (132 mg, 0.46 mmol, 1.0 eq) and allowed to stir at room temperature for 1 h. After LC-MS analysis reaction mixture was concentrated under reduced pressure. Crude residue thus obtained was passed through a Combiflash column [eluent 15-20% EtOAc-Hexane] to provide N1-(2-(4-((5-chloropyridin-2-yl)oxy)piperidin-1-yl)-3-fluorophenyl)-N4,N4-dimethylbenzene-1,4-disulfonamide (54 mg, 20%) as white solid.

Example 45

Step 1. To a stirred solution of tert-butyl 4-hydroxypiperidine-1-carboxylate (500 mg, 2.48 mmol, 1 eq) in DMF (5 mL) was added NaH (60%) (198 mg, 4.97 mmol, 2 eq) portion wise at ice cool condition. The reaction mixture was stirred for 10 min at same temperature. After 10 min, 5-chloro-2,3-difluoropyridine (0.29 mL, 2.48 mmol, 1 eq) was added to the reaction mixture. The resulting reaction mixture was stirred at room temperature for 3 hr. After completion [monitored by TLC, mobile phase 10% EtOAc-Hexane, Rf-0.5] reaction mixture was diluted with water [100 mL] and extracted with EtOAc [25 mL×2]. Organic layer was separated, dried over sodium sulfate and concentrated under reduced pressure. Resultant crude was purified by Combiflash column chromatography using 0-10% ethyl acetate in hexane as eluting solvent to afford tert-butyl 4-((5-chloro-3-fluoropyridin-2-yl)oxy)piperidine-1-carboxylate (600 mg, 73%) as colorless liquid. To a stirred solution of tert-butyl 4-[(5-chloro-3-fluoro-2-pyridyl)oxy] piperidine-1-carboxylate (600 mg, 1.81 mmol, 1 eq) in DCM (3 ml) was added 4 (N) dioxane HCl (3 mL) at ice cool condition. The reaction mixture was stirred at room temperature for 2 h. After completion [monitored by TLC, mobile phase 10% EtOAc-Hexane, Rf-0], the volatile part was evaporated to get the crude product. The crude was azeotrope by toluene to afford 5-chloro-3-fluoro-2-(piperidin-4-yloxy) pyridine hydrochloride (461 mg, 95%) as white solid.

Step 2. To a stirred solution of 5-chloro-3-fluoro-2-(4-piperidyloxy)pyridine; hydrochloride (200 mg, 0.75 mmol, 1 eq) in DMF (5 mL) was treated with $K_2CO_3$ (208 mg, 1.51 mmol, 2 eq) and followed by the addition of 1,2-difluoro-3-nitro-benzene (0.08 ml, 0.75 mmol, 1 eq) at room temperature. The reaction mixture was continued at 80° C. temperature for 4 h. After completion [Monitored with TLC, Mobile Phase 10% EtOAc-Hexane, Rf-0.5] reaction mixture was diluted with water [50 mL] and extracted with EtOAc [15 mL×2]. Organic layer was separated, dried over sodium sulfate and concentrated under reduced pressure. Resultant crude was purified by Combiflash column chromatography using 0-10% ethyl acetate in hexane as eluting solvent to afford 5-chloro-3-fluoro-2-[[1-(2-fluoro-6-nitro-phenyl)-4-piperidyl]oxy]pyridine (250 mg, 89%) pale yellow liquid.

Step 3. To a stirred solution of 5-chloro-3-fluoro-2-[[1-(2-fluoro-6-nitro-phenyl)-4-piperidyl]oxy]pyridine (150 mg, 0.4 mmol, 1 eq) in 1, 4-dioxane (3 mL) was added $NH_4Cl$ (152 mg, 2.84 mmol, 7 eq) in $H_2O$ (2 mL). Then Zn dust (185 mg, 2.84 mmol, 7 eq) was added to the reaction mixture at ice-cold condition, and the reaction was stirred at RT for 2 h. After completion [Monitored with TLC, Mobile Phase: 10% EtOAc-Hexane, Rf-0.2] insoluble part was filtered through glass sintered and filtrate part was concentrated under reduced pressure. The crude residue thus obtained was partitioned between EtOAc [100 mL] and water [60 mL]. Organic layer was separated, dried over sodium sulfate and concentrated under reduced pressure to afford 2-[4-[(5-chloro-3-fluoro-2-pyridyl)oxy]-1-piperidyl]-3-fluoro-aniline (100 mg, 72%) as brown liquid. This compound was used in the next step without further purification.

Step 4. To a stirred solution of 2-[4-[(5-chloro-3-fluoro-2-pyridyl)oxy]-1-piperidyl]-3-fluoro-aniline (100 mg, 0.29 mmol, 1.0 eq) in pyridine (2 mL) was added 4-(dimethylsulfamoyl)benzenesulfonyl chloride (CAS: 677782-39-7) (83 mg, 0.29 mmol, 1.0 eq) and allowed to stir at room temperature for 1 h. After LC-MS analysis reaction mixture was concentrated under reduced pressure. Crude residue thus obtained was passed through a Combiflash column [eluent 15-20% EtOAc-Hexane] to provide N1-(2-(4-((5-chloro-3-fluoropyridin-2-yl)oxy)piperidin-1-yl)-3-fluorophenyl)-N4,N4-dimethylbenzene-1,4-disulfonamide (50 mg, 29%) as white solid.

RP Preparative HPLC Methods

RP Preparative HPLC Method: (Method-1)

Preparative HPLC was done on WATERS BGM 2545 equipped with WATERS PDA Detector 2998 set to multiple-wavelength UV (200-400 nm) detection. Column name: Sunfire $C_{18}$ (150×19 mm, 10µ) operating at ambient temperature and flow rate of 16 ml/min. Mobile phase: A=10 mM NH4OAc in water, B=ACN; Gradient Profile: Mobile phase initial composition of 50% A and 80% B, then 35% A and 65% B in 2 min, then to 20% A and 80% B in 16 min., then to 5% A and 95% B in 17 min., held this composition up to 20 min. for column washing, then returned to initial composition in 21 min. and held till 24 min.

RP Preparative HPLC Method: (Method-2)

Preparative HPLC was done on GILSON BGM 2545 equipped with WATERS PDA Detector 2998 set to multiple-wavelength UV (200-400 nm) detection. Column name: Sunfire C18 (150×19 mm, 10µ) operating at ambient temperature and flow rate of 16 ml/min. Mobile phase: A=10 mM NH4OAc in water, B=ACN; Gradient Profile: Mobile phase initial composition of 60% A and 40% B, then 30% A and 70% B in 2 min, then to 100% B in 20 min., then to 100% B in 21 min., held this composition up to 23 min. for column washing, then returned to initial composition in 24 min. and held till 27 min.

RP Preparative HPLC Method: (Method-3)

Preparative HPLC was done on WATERS BGM 2545 equipped with WATERS PDA Detector 2998 set to multiple-wavelength UV (200-400 nm) detection. Column name: Hydrosphere $C_{18}$ (250×20 mm, 5µ) operating at ambient temperature and flow rate of 16 ml/min. Mobile phase: A=10 mM NH4OAc in water, B=ACN; Gradient Profile: Mobile phase initial composition of 50% A and 50% B, then 30% A and 70% B in 5 min, then to 20% A and 80% B in 30 min., then to 5% A and 95% B in 31 min., held this composition up to 33 min. for column washing, then returned to initial composition in 34 min. and held till 36 min.

RP Preparative HPLC Method: (Method-4)

Preparative HPLC was done on WATERS BGM 2545 equipped with WATERS PDA Detector 2998 set to multiple-wavelength UV (200-400 nm) detection. Column name: YMC Actus Triart $C_{18}$ (250×20 mm, 5µ) operating at ambient temperature and flow rate of 16 ml/min. Mobile phase: A=20 mM NH4HCO3 in water, B=ACN; Gradient Profile: Mobile phase initial composition of 70% A and 30% B, then 30% A and 70% B in 2 min, then to 10% A and 90% B in 22 min., then to 5% A and 95% B in 23 min., held this composition up to 26 min. for column washing, then returned to initial composition in 27 min. and held till 30 min.

Analytical LCMS Method

LCMS Method-1: (for 3 Min Run)

The HPLC measurement was performed using Waters Acquity H Class UPLC comprising a quaternary pump with degasser, a sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Acquity BEH C8 column (1.7 µm, 50×2.1 mm) with a flow rate of 0.800 ml/min. Two mobile phases were used, mobile phase A: 0.05% HCOOH in water; mobile phase B: 0.05% HCOOH in ACN:Water (90:10)], and they were employed to run a gradient condition from 10% B for 0.75 minutes, from 10% to 50% in 0.25 minutes, and from 50% to 98% in 1.00 minutes, 98% B for 0.25 minutes and then 10% B in 0.35 minutes and hold these conditions for 0.40 minutes in order to re-equilibrate the column (Total Run Time 3.00 minutes). An injection volume of 0.5 µl was used.

LCMS Method-2: (for 5 Min Run)

The HPLC measurement was performed using Waters Acquity H Class UPLC comprising a quaternary pump with degasser, a sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Acquity BEH $C_8$ column (1.7 μm, 50×2.1 mm) with a flow rate of 0.800 ml/min. Two mobile phases were used, mobile phase A: 0.05% HCOOH in water; mobile phase B: 0.05% HCOOH in ACN:Water (90:10)], and they were employed to run a gradient condition from 5% B for 0.75 minutes, from 5% to 25% in 0.75 minutes, and from 25% to 95% in 1.50 minutes, 95% B for 1.00 minutes and 5% B in 0.50 minutes and hold these conditions for 0.60 minutes in order to re-equilibrate the column (Total Run Time 5.10 minutes). An injection volume of 0.5 μl was used.

LCMS Method-3:

The HPLC measurement was performed using Waters Acquity UPLC comprising a binary pump with degasser, a sample manager, a column oven (set at 50° C.), a diode-array detector DAD and a column as specified in the respective methods below. Flow from the column was split to a MS spectrometer. The MS detector (Waters ZQ SQD) was configured with an electrospray ionization source. Mass spectra were acquired by scanning from 100 to 1000 in 0.40 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.1 Software. Reversed phase HPLC was carried out on a YMC Triart C18 column (3 μm, 33×2.1 mm) with a flow rate of 1.00 ml/min. Two mobile phases were used, mobile phase A: 0.05% HCOOH in water; mobile phase B: 0.05% HCOOH in ACN:Water (90:10)], and they were employed to run a gradient condition from 2% B for 0.75 minutes, from 2% to 10% in 0.25 minutes, and from 10% to 98% in 1.00 minutes, 98% B for 0.50 minutes and then 2% B in 0.40 minutes and hold these conditions for 0.10 minutes in order to re-equilibrate the column (Total Run Time 3.00 minutes). An injection volume of 0.5 to 3 μl was used (Depending on the sample concentration).

LCMS Method 4:

The HPLC measurement was performed using Waters Acquity H Class UPLC comprising a quaternary pump with degasser, a sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 100 to 1000 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Acquity BEH C18 column (1.7 μm, 30×2.1 mm) with a flow rate of 0.500 ml/min. Two mobile phases were used, mobile phase A: 5 Mm NH4oAc in water; mobile phase B: 5 Mm NH4oAc in ACN:Water (90:10)], and they were employed to run a gradient condition from 2% B for 1.00 minutes, from 2% to 50% in 4.00 minutes, and from 50% to 90% in 3.00 minutes, 90% B for 2.00 minutes and 2% B in 2.00 minutes and hold these conditions for 0.10 minutes in order to re-equilibrate the column (Total Run Time 12.10 minutes). An injection volume of 1.5 μl was used.

LCMS Method-5:

The HPLC measurement was performed using Waters Acquity H Class UPLC comprising a quaternary pump with degasser, a sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 100 to 1000 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Acquity BEH C18 column (1.7 μm, 30×2.1 mm) with a flow rate of 0.500 ml/min. Two mobile phases were used, mobile phase A: 5 Mm NH4oAc in water; mobile phase B: 5 Mm NH4oAc in ACN:Water (90:10)], and they were employed to run a gradient condition from 2% B for 0.50 minutes, from 2% to 98% in 1.00 minutes, 98% B for 1.00 minutes and 2% B in 0.25 minutes and hold these conditions for 0.25 minutes in order to re-equilibrate the column (Total Run Time 3.00 minutes). An injection volume of 0.3 μl was used.

LCMS Method-6:

The HPLC measurement was performed using Waters Acquity H Class UPLC comprising a quaternary pump with degasser, a sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 100 to 1000 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Xbridge C18 column (3.5 μm, 50×3 mm) with a flow rate of 1.20 ml/min. Two mobile phases were used, mobile phase A: 5 Mm NH4oAc in water; mobile phase B: 5 Mm NH4oAc in ACN:Water (90:10)], and they were employed to run a gradient condition from 5% B for 0.75 minutes, from 5% to 30% in 0.25 minutes, and from 30% to 98% in 1.00 minutes, 98% B for 0.25 minutes and 5% B in 0.50 minutes and hold these conditions for 0.25 minutes in order to re-equilibrate the column (Total Run Time 3.00 minutes). An injection volume of 0.30 μl was used.

LCMS Method-7:

The HPLC measurement was performed using Waters Acquity H Class UPLC comprising a quaternary pump with degasser, an sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 100 to 1000 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Xbridge C18 column (5 μm, 50×4.6 mm) with a flow rate of 1.50 ml/min. Two mobile phases were used, mobile phase A: 5 Mm NH4oAc in water; mobile phase B: 5 Mm $NH_4OAc$ in ACN:Water (90:10)], and they were employed to run a gradient conditions from 2% B for 0.75 minutes, from 2% to 15% in 0.50 minutes, from 15% to 70% in 1.25 minutes, and from 70% to 98% in 1.25 minutes, 98% B for 0.75 minutes and 2% B in 0.50 minutes and hold these conditions for 0.10 minutes in order to re-equilibrate the column (Total Run Time 5.10 minutes). An injection volume of 0.50 to 1 μl was used (Depending upon the concentration of the sample).

NMR Characterization $^1$H NMR spectra were recorded on a Varian Mercury NMR 400 MHz spectrometer using $CDCl_3$, DMSO-d6 or $CD_3OD$ as solvents Chemical shifts (δ) are reported in parts per million (ppm) relative to residual signal of non-fully deuterated solvents pick for $^1$H NMR assigned as 7.26 ppm for $CHCl_3$, 3.31 ppm for $CHD_2OD$ and 2.50 ppm for DMSO-$d_5$.

TABLE 2

NMR and LCMS characterization of Specific Examples

| Example # | NMR Annotation | LCMS Method | $[M + H]^+$ | Rt (min) |
|---|---|---|---|---|
| 1 | 1H NMR (DMSO-d6 at 100° C.) δ ppm 7.53 (m, 4H), 7.36 (d, 1H, J = 7.6 Hz), 7.30 (m, 2H), 7.22 (m, 1H), 7.12 (m, 1H), 6.98 (m, 4H), 4.54 (bm, 2H), 2.95 (bm, 2H), 2.55 (s, 6H), 2.00 (bm, 4H), 1.89 (bm, 7H), 1.56 (bm, 3H). | LCMS method-3 | 548.24 | 2.24 |
| 2 | 1HNMR: (DMSO-d6, 100° C.) δ ppm: 7.57(d, 2H, J = 8.16 Hz), 7.51 (d, 2H, J = 8.28 Hz), 7.37 (d, 1H, J = 7.76 Hz), 7.30 (m, 3H), 7.14 (t, 1H, J = 7.52 Hz, 7.44 Hz), 6.99 (m, 4H), 4.72 (t, 1H, J = 8.4 Hz, 8.52 Hz), 4.46 (m, 1H), 2.94 (bm, 4H), 2.57 (s, 6H), 2.17 (bm, 4H), 2.03 (bm, 2H), 1.80 (m, 2H), 1.72 (m, 2H). | LCMS method-1 | 534.38 | 2.3 |
| 3 | 1H NMR (DMSO-d6) δ ppm 7.56 (bm, 5H), 7.28 (t, 2H, J = 8 & 7.68 Hz), 7.18 (m, 2H), 6.98 (d, 2H, J = 8.16 Hz), 6.91 (t, 2H, J = 7.32 Hz), 4.46 (bs, 2H), 3.78 (bs, 1H), 3.61 (bs, 1H), 3.43 (bs, 1H), 3.33 (bs, 3H), 2.98 (bs, 1H), 2.78 (bs, 1H), 2.47 (s, 6H), 2.21 (bs, 2H), 1.97 (bs, 2H), 1.74 (bm, 2H). | LCMS method-7 | 538.1 | 3.27 |
| 4 | 1H NMR (DMSO-d6 at 100° C.) δ ppm 7.57 (m, 4H), 7.35 (m, 3H), 7.22 (m, 1H), 7.10 (m, 1H), 7.00 (m, 4H), 4.49 (m, 1H), 4.18 (bs, 1H), 3.39 (bs, 1H), 2.74 (bm, 2H), 2.56 (s, 6H), 2.03 (bs, 2H), 1.79 (m, 4H), 0.953 (t, 3H, J = 7.6 & 7.2 Hz) | LCMS method-7 | 522.2 | 3.46 |
| 5 | 1H NMR (DMSO-d6 at 100° C.) δ ppm 7.66 (q, 4H, J = 8.4 Hz, 8 Hz), 7.31 (m, 4H), 7.10 (m, 2H), 7.00 (m, 3H), 4.51 (m, 1H), 3.32 (m, 1H), 2.77 (bm, 2H), 2.60 (s, 6H), 2.05 (bm, 2H), 1.84 (bm, 2H), 0.72 (bm, 2H), 0.62 (bs, 2H). | LCMS method-7 | 520.3 | 3.31 |
| 6 | 1H NMR (DMSO-d6 at 100° C.) δ ppm 8.93 (s, 1H), 8.05 (s, 4H), 7.34 (m, 3H), 7.19 (m, 3H), 6.98 (m, 4H), 4.44 (bs, 1H), 3.32 (dd, 2H, J = 7.32 Hz, 7.24 Hz), 2.77 (bs, 2H), 2.62 (m, 2H), 1.96 (bs, 2H), 1.76 (m, 2H), 1.10 (t, 3H, J = 7.32 Hz). | LCMS method-7 | 501.2 | 3.44 |
| 7 | 1H NMR (DMSO-d6, 100° C.) δ ppm 9.08 (s, 1H), 8.16 (m, 1H), 8.03 (d, 2H, J = 8.4 Hz), 7.94 (d, 2H, J = 8.4 Hz), 7.70 (m, 1H), 7.29 (d, 1H, J = 7.2), 7.20 (m, 2H), 6.95 (m, 1H), 6.79 (d, 1H, J = 8.4), 5.14 (bs, 1H), 2.96 (bm, 4H), 2.66 (s, 6H), 2.06 (m, 2H), 1.86 (m, 2H). | LCMS method-1 | 551.28 | 2.22 |
| 8 | 1H NMR (DMSO-d6) δ ppm 9.47 (s, 1H), 8.14 (dd, 1H, J = 1.76 Hz, J = 1.76 Hz), 7.99 (d, 2H, J = 8.48 Hz), 7.94 (d, 2H, J = 8.48 Hz), 7.71 (m, 1H), 7.27 (m, 2H), 7.03 (m, 2H), 6.79 (d, 1H, J = 8.32 Hz), 5.02 (t, 1H, J = 3.84 Hz), 2.67 (m, 2H), 2.57 (s, 8H), 1.94 (m, 2H), 1.78 (m, 2H). | LCMS method-7 | 535.2 | 3.08 |
| 9 | 1H NMR (DMSO-d6) δ ppm 8.14 (dd, 1H, J = 1.72 Hz, J = 4.92 Hz), 7.71 (m, 1H), 7.62 (bs, 4H), 7.42 (d, 1H, J = 7.88 Hz), 7.29 (m, 1H), 7.17 (m, 1H), 6.96 (m, 1H), 6.81 (d, 1H, J = 8.32 Hz), 5.09 (bm, 1H), 3.35 (m, 3H), 2.97 (m, 4H), 2.59 (s, 6H), 2.02 (m, 2H), 1.77 (m, 2H). | LCMS method-1 | 513.31 | 2.02 |
| 10 | 1H NMR (DMSO-d6) δ ppm 9.45 (s, 1H), 8.14 (dd, 1H, J1 = 1.6 Hz, 4.96 Hz) 7.97 (s, 4H), 7.69 (t, 1H, J = 1.44 Hz, 6.68 Hz), 7.23 (m, 2H), 6.95 (m, 2H), 6.79 (d, 1H, J = 8.32 Hz), 5.01 (s, 1H), 2.88 (m, 2H), 2.65 (m, 2H), 1.90 (m, 2H), 1.76 (m, 2H). | LCMS method-1 | 496.26 | 2.38 |

TABLE 2-continued

NMR and LCMS characterization of Specific Examples

| Example # | NMR Annotation | LCMS Method | $[M + H]^+$ | Rt (min) |
|---|---|---|---|---|
| 11 | $^1$H NMR (DMSO-d6 at 100° C.) δ ppm 8.14 (d, 1H, J = 4 Hz), 7.70 (m, 5H), 7.26 (m, 2H), 7.17 (m, 1H), 6.94 (m, 1H), 6.79 (d, 1H, J = 8 Hz), 5.15 (m, 1H), 4.41 (t, 1H, J = 6.4 Hz), 2.82 (bs, 4H), 2.59 (s, 6H), 2.02 (m, 2H), 1.78 (m, 2H), 1.32 (d, 6H, J = 4.8 Hz). | LCMS method-1 | 541.31 | 2.24 |
| 12 | $^1$H NMR (DMSO-d6 at 100° C.) δ ppm 8.14 (d, 1H, J = 4 Hz), 7.70 (m, 5H), 7.30 (m, 2H), 7.18 (m, 1H), 6.94 (t, 1H, J = 6 Hz), 6.80 (d, 1H, J = 8 Hz), 5.16 (m, 1H), 4.65 (m, 1H), 2.97 (s, 2H), 2.60 (s, 6H), 2.13 (m, 6H), 1.79 (m, 2H), 1.67 (m, 2H). | LCMS method-1 | 553.34 | 2.29 |
| 13 | 1H NMR (DMSO-d6) δ ppm 9.62 (s, 1H), 8.14 (m, 1H), 8.04 (d, 2H, J = 8.40 Hz), 7.96 (d, 2H, J = 8.40 Hz), 7.69 (d, 1H, J = 1.4 Hz), 7.29 (d, 1H, J = 1.2), 7.21 (bs, 2H), 6.96 (m, 1H), 6.78 (d, 1H, J = 8.4 Hz), 5.05 (m, 1H), 2.58 (bs, 8H), 1.94 (m, 2H), 1.77 (m, 2H). | LCMS method-1 | 551.21 | 2.25 |
| 14 | 1H NMR (DMSO-d6) δ ppm 9.22 (s, 1H), 8.14 (dd, 1H, J = 1.64, 5.04 Hz), 8.00 (d, 2H, J = 8.48), 7.92 (d, 2H, J = 8.44 Hz), 7.71 (m, 1H), 7.17 (bs, 1H), 7.08 (d, 1H, J = 8.08 Hz), 6.95 (m, 2H), 6.78 (d, 1H, J = 4.48 Hz), 2.57 (s, 6H), 2.50 (m, 2H), 2.47 (m, 2H), 2.23 (s, 3H), 1.93 (m, 2H), 1.73 (m, 2H). | LCMS method-6 | 531.2 | 2.17 |
| 15 | 1H NMR (DMSO-d6) δ ppm 9.51 (s, 1H), 8.14 (m, 1H), 8.08 (d, 2H, J = 8.4 Hz), 8.02 (d, 2H, J = 8.52 Hz), 7.71 (m, 1H), 7.26 (m, 2H), 7.02 (m, 1H), 6.96 (m, 1H), 6.79 (d, 1H, J = 8.4 Hz), 5.03 (m, 1H), 3.34 (m, 2H), 2.67 (bs, 2H), 2.57 (bs, 2H), 1.93 (bm, 2H), 1.76 (bm, 2H), 1.02 (t, 3H, 7.2 & 7.6 Hz). | LCMS method-1 | 520.28 | 2.19 |
| 16 | 1H NMR (DMSO-d6) δ ppm 8.14 (d, 1H, J = 3.56 Hz), 7.69 (t, 1H, J = 6.64 Hz), 7.47 (bs, 3H), 7.24 (bs, 1H), 6.99 (bs, 1H), 6.96 (m, 1H), 6.80 (d, 2H, J = 8.32 Hz), 5.05 (bs, 1H), 4.49 (bs, 1H), 2.98 (bs, 1H), 2.76 (bs, 1H), 2.50 (s, 6H), 2.29 (s, 3H), 2.16 (bs, 2H), 2.01 (m, 4H), 1.73 (m, 6H), 1.55 (bs, 2H). | LCMS method-6 | 563.74 | 2.39 |
| 17 | 1H NMR (DMSO-d6) δ ppm 9.41 (s, 1H), 7.98 (bm, 4H), 7.31 (d, 1H, J = 7.52 Hz), 7.14 (bm, 3H), 3.26 (bs, 4H), 2.38 (bs, 4H), 1.39 (s, 9H). | LCMS method-2 | 486.27 | 3.38 |
| 18 | 1H NMR (DMSO-d6) δ ppm 9.07 (s, 1H), 7.65 (t, 1H, J = 7.92 Hz, J = 7.88 Hz), 7.30 (bm, 2H), 7.21 (bm, 1H), 7.16 (d, 1H, J = 8.0 Hz), 7.09 (bm, 2H), 3.41 (bs, 4H), 2.56 (bs, 4H), 2.34 (s, 3H), 1.42 (s, 9H). | LCMS method-1 | 450.28 | 2.24 |
| 19 | 1H NMR (DMSO-d6) δ ppm 9.10 (s, 1H), 7.55 (d, 1H, J = 9.52 Hz), 7.51 (bm, 2H), 7.31 (bm, 1H), 7.16 (bm, 1H), 7.11 (bm, 2H), 3.38 (bs, 4H), 2.45 (bs, 4H), 2.27 (s, 3H), 1.41 (s, 9H). | LCMS method-1 | 450.28 | 2.27 |
| 20 | 1H NMR (CDCl3) δ ppm 8.04 (bs, 1H), 7.83 (bs, 1H), 7.38 (d, 1H, J = 7.96 Hz), 7.20 (bd, 1H, J = 6.8 Hz), 7.12 (bm, 3H), 6.99 (bm, 1H), 3.54 (bs, 4H), 2.66 (bs, 4H), 2.57 (s, 3H), 2.33 (s, 3H), 1.47 (s, 9H) | LCMS method -1 | 446.35 | 2.38 |
| 21 | 1H NMR (DMSO-d6) δ ppm 9.22 (s, 1H), 7.86 (d, 2H, J = 8.76 Hz), 7.57 (d, 2H, J = 8.4 Hz), 7.37 (m, 1H), 7.14 (bm, 3H), 3.27 (bs, 4H), 2.35 (bs, 4H), 1.39 (s, 9H). | LCMS method-1 | 502.29 | 2.42 |
| 22 | 1H NMR (DMSO-d6 at 100° C.) δ ppm 8.46 (s, 1H), 7.64 (d, 2H, J = 8 Hz), 7.35 (d, 2H, J = 8 Hz), 7.12 (t, 1H, J = 8.0 Hz, 7.6 Hz), 6.97 (d, 1H, J = 7.6 Hz), 6.91 (d, 1H, J = 8 Hz), 3.10 (t, 4H, J = 4.8 Hz, 5.2 Hz), 2.59 (t, 4H, J = 5.2 Hz, 4.8 Hz), 2.38 (s, 3H), 2.23 (s, 3H), 1.42 (s, 9H). | LCMS method-1 | 446.33 | 2.29 |
| 23 | 1H NMR (DMSO-d6 at 100° C.) δ ppm 8.87 (s, 1H), 7.64 (d, 2H, J = 8.4 Hz), 7.37 (t, 1H, J = 5.2 Hz, 4.4 Hz), 7.23 (d, 2H, J = 8.4 Hz), 7.13 (m, 1H), 7.09 (m, 2H), 3.39 (t, 4H, J = 4.8 Hz, 5.2 Hz), 2.50 (m, 4H) ,1.99 (bs, 1H), 1.44 (s, 9H), 1.03 (m, 2H), 0.73 (m, 2H). | LCMS method-1 | 458.29 | 2.28 |

TABLE 2-continued

NMR and LCMS characterization of Specific Examples

| Example # | NMR Annotation | LCMS Method | [M + H]$^+$ | Rt (min) |
|---|---|---|---|---|
| 24 | 1H NMR (DMSO-d6) δ ppm 9.08 (bs, 1H) 7.97 (m, 4H,), 7.13 (m, 2H), 6.93 (m, 1H), 6.84 (m, 1H), 2.99 (bs, 4H), 2.61 (s, 6H), 1.57 (s, 10 H) | LCMS method-1 | 452.21 | 2.18 |
| 25 | 1H NMR (DMSO-d6 at 100° C.) δ ppm 8.84 (s, 1H), 7.98 (d, 2H, J = 8.4 Hz), 7.88 (d, 2H, J = 8.4 Hz), 7.39 (m, 5H), 7.29, (m, 1H), 7.14 (m, 3H), 4.60(s, 2H), 3.64 (m, 1H), 2.98 (m, 1H), 2.65 (m, 7H), 2.55 (m, 1H), 2.50, (bm, 1H), 1.91 (bm, 1H), 1.71 (bs, 1H), 1.54 (bm, 2H) | LCMS method-1 | 530.29 | 2.26 |
| 26 | 1H NMR (DMSO-d6 at 100° C.) δ ppm 8.89 (s, 1H), 7.98 (d, 2H, J = 8 Hz), 7.87 (d, 2H, J = 8 Hz), 7.39 (m, 6H), 7.12 (m, 3H), 4.60 (s, 2H), 3.64 (bs, 1H), 2.66 (s, 6H), 2.55 (m, 1H), 2.49 (m, 2H), 1.85 (m, 1H), 1.72 (bm, 1H), 1.54 (bm, 2H), 1.31 (m, 1H). | LCMS method-2 | 530.57 | 2.14 |
| 27 | 1H NMR (DMSO-d6 at 100° C.) δ ppm 8.78 (s, 1H), 7.98 (d, 2H, J = 8 Hz), 7.88 (d, 2H, J = 8.4 Hz), 7.40 (bm, 6H), 7.14 (m, 3H), 4.60 (s, 2H), 3.64 (bs, 1H), 2.90 (bm, 2H), 2.66 (bs, 6H), 2.55 (m, 1H), 2.50 (bm, 1H), 1.85 (bm, 1H), 1.72 (bm, 1H), 1.55 (bm, 2H). | LCMS method-3 | 530.57 | 2.14 |
| 28 | 1H NMR (DMSO-d6 at 100° C.) δ ppm 7.99 (dd, 2H, J = 1.6 Hz, J = 7.2 Hz), 7.86 (d, 2H, J = 8.4 Hz), 7.38 (bm, 4H), 7.10 (bm, 5H,), 4.59 (m, 1H), 2.64 (m, 8H), 2.53 (m, 1H), 1.92 (m, 1H), 1.67 (m, 4H). | LCMS method-3 | 516.44 | 2.18 |
| 29 | 1H NMR (DMSO-d6 at 100° C.) δ ppm 8.88 (bs, 1H), 7.99 (d, 2H, J = 7.6 Hz), 7.86 (d, 2H, J = 7.6 Hz), 7.36 (bs, 1H), 7.31 (t, 2H, J = 7.2 Hz), 7.17 (bs, 1H), 7.10 (bm, 4H), 6.96 (t, 1H, J = 7.2 Hz, 6.4 Hz), 4.60 (bs, 1H), 3.00 (bs, 1H), 2.65 (bs, 7H), 2.50 (bs, 1H), 1.92 (bs, 1H), 1.81 (bs, 1H), 1.66 (bm, 3H), 1.53 (bs, 1H), 1.27 (bs, 2 H), 1.21 (m, 4H), 0.84 (m, 3H). extra peak present in aliphatic region | LCMS method-1 | 516.28 | 2.3 |
| 30 | 1H NMR (DMSO-d6 at 100° C.) δ ppm 8.87 (bs, 1H), 7.99 (d, 2H, J = 7.6 Hz), 7.86 (d, 2H, J = 7.6 Hz), 7.38 (d, 1H, J = 6.4 Hz), 7.31 (t, 2H, J = 7.6 Hz), 7.17 (bs, 1H), 7.10 (bm, 4H), 6.96 (t, 1H, J = 7.6 Hz, 6.8 Hz), 4.59 (bs, 1H), 3.00 (bs, 1H), 2.67 (d, 7H, J = 9.6 Hz), 2.52 (s, 1H), 1.92 (bs, 1H), 1.77 (s, 1H), 1.67 (m, 3H), 1.55 (bs, 1H), 1.27 (bs, 2H), 1.20 (m, 4H), 0.86 (m, 2H). extra peak present in aliphatic region | LCMS method-1 | 516.26 | 2.3 |
| 31 | 1H NMR (DMSO-d6) δ ppm 9.42 (s, 1H), 7.98 (d, 2H, J = 8.2 Hz), 7.92 (d, 2H, J = 8.44 Hz), 7.25 (d, 1H, J = 7.88 Hz), 7.16 (t, 2H, J = 5.64 Hz, J = 5.36 Hz), 7.10 (m, 1H), 3.67 (d, 1H, J = 10.84 Hz), 3.42 (t, 1H, J = 9.2 Hz), 2.82 (m, 1H), 2.67 (m, 1H), 2.61 (s, 6H), 2.57 (m, 1H), 2.45 (m, 1H), 2.30 (d, 1H, J = 10.32 Hz), 0.75 (m, 1H), 0.42 (m, 2H), 0.26 (m, 2H). | LCMS method-1 | 466.25 | 2.06 |
| 32 | 1H NMR (DMSO-d6) δ ppm 9.44 (s, 1H), 7.99 (d, 2H, J = 8.52 Hz), 7.94 (d, 2H, J = 8.48 Hz), 7.25 (d, 1H, J = 7.68 Hz), 7.17 (bm, 3H), 3.7 (d, 1H, J = 10 Hz), 3.48 (t, 1H, J = 9.04 Hz), 2.6 (s, 6H), 2.54 (d, 1H, J = 3 Hz), 2.47 (m, 2H, J = 11.28 Hz), 2.35 (d, 1H, J = 11 Hz), 2.20 (m, 2H), 1.88 (m, 6H) | LCMS method-7 | 480.2 | 3.02 |
| 33 | 1H NMR (DMSO-d6) δ ppm 9.50 (s, 1H), 8.00 (d, 2H, J = 8.8 Hz), 7.93 (d, 2H, J = 8.4 Hz), 7.27 (d, 1H, J = 7.2 Hz), 7.15 (m, 3 H), 3.70 (m, 2H), 3.56 (m, 1H), 2.83 (t, 1H, J = 2.8 Hz), 2.69 (s, 6H), 2.59 (m, 2H), 2.43 (m, 1H), 2.32 (m, 3H) | LCMS method-1 | 464.22 | 2.03 |
| 34 | 1H NMR (DMSO-d6) δ ppm 9.17 (s, 1H), 8.00 (d, 2H, J = 8.36 Hz), 7.89 (d, 2H, J = 8.36 Hz), 7.26 (m, 3H), 7.12 (m, 2H), 7.01 (t, 1H, J = 8.56 Hz), 6.91 (m, 3H), 3.87 (bm, 2H), 2.84 (d, 1H, J = 10.84 Hz), 2.57 (s, 6H), 2.42 (m, 3H), 2.15 (bs, 1H), 1.77 (d, 1H, J = 9.16 Hz), 1.56 (bs, 2H), 1.20 (m, 1H), | LCMS method-1 | 530.27 | 2.38 |

TABLE 2-continued

NMR and LCMS characterization of Specific Examples

| Example # | NMR Annotation | LCMS Method | $[M + H]^+$ | Rt (min) |
|---|---|---|---|---|
| 35 | 1H NMR (DMSO-d6 at 100° C.) δ ppm 7.99 (d, 2H, J = 8.4 Hz), 7.66 (d, 2H, J = 8 Hz), 7.25 (t, 2H, J = 8 Hz), 7.19 (d, 1H, J = 8.4 Hz), 6.96 (m, 3H), 6.71 (d, 1H, J = 7.2 Hz), 6.62 (t, 1H, J = 8 Hz), 6.55 (d, 1H, J = 7.2 Hz), 4.00 (t, 2H, J = 3.6 Hz), 3.31 (d, 1H, J = 10 Hz), 3.22 (bs, 1H), 2.67 (d, 1H, J = 8.4 Hz), 2.62 (s, 6H), 2.11 (bs, 2H), 1.79 (m, 1H), 1.67 (m, 2H), 1.37 (m, 2H) extra peak present in aliphatic region | LCMS method-3 | 530.24 | 2.23 |
| 36 | 1H NMR (DMSO-d6 at 100° C.) δ ppm, 7.98 (d, 2H, J = 8 Hz), 7.63 (d, 2H, J = 8 Hz), 7.25 (t, 2H, J = 7.2 Hz), 7.17 (d, 1H, J = 8 Hz), 6.96 (d, 2H, J = 8 Hz), 6.89(t, 1H, J = 7.2 Hz), 6.64 (d, 1H, J = 7.6 Hz), 6.56 (t, 1H, J = 7.2 Hz), 6.45 (t, 1H, J = 7.2 Hz), 4.02 (m, 2H), 3.37 (bm, 2H), 2.67 (t, 1H, J = 9.6 Hz), 2.61(bs, 6H), 2.10 (bs, 2H), 1.79(bm, 1H), 1.67(bm, 2H), 1.37 (bm, 2H) | LCMS method-3 | 530.24 | 2.23 |
| 37 | 1H NMR (DMSO-d6 at 100° C.) δ ppm 9.00 (s, 1H), 8.02 (d, 2H, J = 8.4 Hz), 7.92 (d, 2H, J = 8.36 Hz), 7.40 (m, 4H), 7.23 (m, 2H), 7.15 (m, 1H), 6.89 (m, 1H), 2.91 (m, 2H), 2.67 (bs, 6H), 2.64 (m, 2H), 2.13 (m, 2H), 1.78 (bm, 2H), 1.26 (s, 3H). | LCMS method-1 | 532.27 | 2.41 |
| 38 | 1H NMR (DMSO-d6) δ ppm 9.23 (s, 1H), 8.02 (d, 2H, J = 8.48 Hz), 7.93 (d, 2H, J = 8.4 Hz), 7.40 (d, 2H, J = 7.68 Hz), 7.36 (m, 2H), 7.27 (m, 1H), 7.21 (t, 1H, J = 7.08 Hz), 7.09 (m, 3H), 2.69 (m, 2H), 2.61 (s, 6H), 2.44 (m, 2H), 2.11 (m, 2H), 1.74 (m, 2H), 1.21 (s, 3H). | LCMS method-7 | 514.2 | 3.51 |
| 39 | 1H NMR (DMSO-d6 at 100° C.) δ ppm 8.55 (s, 1H), 7.58 (bs, 1H), 7.51 (dd, 1H, J = 7.92 & 7.96 Hz), 7.41 (m, 3H), 7.30 (d, 1H, J = 8 Hz), 7.23 (m, 2H), 7.16 (m, 2H), 7.12 (m, 2H), 3.62 (t, 4H, J = 4.84 Hz), 2.62 (t, 4H, J = 5.04 & 4.92 Hz), 2.27 (s, 6H) | LCMS method-4 | 464.3 | 7.38 |
| 40 | 1H NMR (DMSO-d6) δ ppm 9.27 (s, 1H), 8.10 (dd, 1H, J = 1.2 Hz), 8.00 (d, 2H, J = 8.4 Hz), 7.92 (d, 2H, J = 8.4 Hz), 7.65 (m, 1H), 7.32 (d, 1H, J = 7.2 Hz), 7.13 (m, 3H), 6.93 (t, 1H, J = 5.6 Hz, 6.4 Hz), 6.77 (d, 1H, J = 8.4 Hz), 2.64 (t, 2H, J = 10.4 Hz), 2.58 (s, 6H), 2.33 (m, 2H), 2.26 (d, 2H, J = 13.6 Hz), 1.80 (m, 2H), 1.61 (s, 3H). | LCMS method-7 | 531.1 | 3.56 |
| 41 | 1H NMR (DMSO-d6 at 100° C.) δ ppm 7.56 (s, 1H), 7.49 (d, 1H, J = 7.48 Hz), 7.32 (d, 1H, J = 6.84 Hz), 7.23 (d, 1H, J = 8.12 Hz), 6.99 (m, 3H), 3.57 (bs, 4H), 2.65 (bs, 4H), 2.25 (s, 6H), 1.83 (bs, 2H), 1.03 (s, 9H). | LCMS method-5 | 444.35 | 1.91 |
| 42 | 1H NMR (DMSO-d6) δ ppm 9.46 (s, 1H), 7.96 (d, 4H, J = 8.28 Hz), 7.30 (d, 1H, J = 7.52 Hz), 7.12 (m, 3H), 3.47 (bm, 4H), 2.36 (bs, 2H), 2.21 (s, 2H), 0.98 (s, 9H) | LCMS method-5 | 484.38 | 2.35 |
| 43 | 1H NMR (DMSO-d6, at 100° C.) δ ppm 9.08 (bs, 1H), 8.53 (s, 1H), 8.03 (bm, 5H), 7.25 (bm, 2H), 6.99(m, 2H), 5.21 (bs, 1H), 2.81 (bs, 4H), 2.66 (s, 6H), 2.04 (m, 2H), 1.89 (m, 2H). | LCMS method-1 | 603.27 | 2.48 |
| 44 | 1H NMR (DMSO-d6 at 100° C.) δ ppm 9.05 (bs, 1H), 8.16 (d, 1H, J = 2.4 Hz), 8.03 (d, 2H, J = 8.4 Hz), 7.93 (d, 2H, J = 8.4 Hz), 7.76 (dd, 1H, J = 8.8 Hz, 2.4 Hz), 7.25 (d, 1H, J = 8.0 Hz), 7.20 (bm, 1H), 6.98 (bm, 1H), 6.84 (d, 1H, J = 9.2 Hz), 5.08 (bm, 1H), 2.80 (m, 4H), 2.66 (s, 6H), 2.02 (m, 2H), 1.85 (bm, 2H). | LCMS method-1 | 569.18 | 2.36 |
| 45 | 1H NMR (DMSO-d6 at 100° C.) δ ppm 9.08 (s, 1H), 8.04 (d, 3H, J = 7.6 Hz), 7.94 (m, 2H), 7.88 (dd, 1H, J = 1.6 Hz), 7.25 (d, 1H, J = 8 Hz), 7.20 (m, 1H), 6.98 (m, 1H), 5.19 (bs, 1H), 2.83 (m, 4H), 2.66 (s, 6H), 2.02 (m, 2H), 1.92 (m, 2H). | LCMS method-6 | 587.14 | 2.29 |

Pharmacology

Cellular TRPML1 Assay

Buffers and reagents

PBS (D-PBS without calcium and magnesium; EuroClone)

Trypsin (Trypsin 0.05%, EDTA 0.02% in PBS; EuroClone)

DMSO (Sigma)

$Ca^{2+}$ free Tyrode's buffer: in-house solution (130 mM NaCl, 5 mM KCl, 1 mM MgCl2, 5 mM NaHCO3, 20 mM HEPES in water at pH 7.4; sterile filtered).

Opti-MEM (Gibco)

Agonist: ML-SA1 (Sigma); stock: 60 mM in DMSO, stored at −20° C.

Blocker: ML-SI3 (in house synthesis); stock: 20 mM in DMSO, stored at −20° C.

Cell line

The final clone for the TRPML1 assay is HEK T-REx/GCaMP6f/TRPML1.

GCaMP6f is a genetically encoded calcium indicator that is stably expressed in this cell line and used as a fluorescent read-out.

Assay Protocol

Experiments are performed in 384 MTP format. Cells are seeded at 15000 cells/well either in 25 l/well of growth medium or in 20 μl/well of Optimem+0.5% FBS without selection antibiotics. Twenty-four hours later, cells are assayed for the response to various compounds using the $Ca^{2+}$ sensitive GCaMP6f protein stably expressed in the cells as readout.

The experiment is performed in a 384-well format according to the following procedures for either $Ca^{2+}$ free or Optimem conditions:

$Ca^{2+}$ free condition (in absence of extracellular $Ca^{2+}$):

24 h after seeding, pre-incubate the cells at room temperature for about 10'.

Then remove the culture medium and replace it with 20 μL of $Ca^{2+}$ free Tyrode's buffer.

Start the experiment at the FLIPR$^{TETRA}$ by injecting 10 μL/w of 3× concentrated test compounds and controls in $Ca^{2+}$ free Tyrode's buffer. Monitor the kinetic response over a period of 300 seconds.

Final DMSO concentration: 0.5%

Optimem condition (in presence of extracellular $Ca^{2+}$):

24 h after seeding, pre-incubate the cells at room temperature for about 10'.

Start the experiment at the FLIPR$^{TETRA}$ by injecting 10 μL/w of 3× concentrated test compounds and controls in $Ca^{2+}$ free Tyrode's buffer. Monitor the kinetic response over a period of 300 seconds.

Final DMSO concentration: 0.5%

Data from FLIPR$^{TETRA}$ measurements are analyzed with the Genedata Screener© software.

Data Analysis

| | |
|---|---|
| Compound | Calculate the Kinetic Response Value (KRV) as: |
| % Activity | $MAX_{CA}$/Baseline = [max(sec5 . . . 290)/Mean (sec 1 . . . sec2)] |
| | Normalize the KRV to the median (< >) of Neutral and Stimulator control wells: |
| | $\text{Activity [\%] \_Ago} = 100 * \left( \frac{x - \langle NeutralControls \rangle}{\langle \text{Stimulator Controls} \rangle - \langle NeutralControls \rangle} \right)$ |

Autophagy Assay

Buffers and Reagents

Tyrode's buffer with 2 mM $Ca^{2+}$ in-house solution (130 mM NaCl, 5 mM KCl, 2 mM CaCl2), 1 mM MgCl2, 5 mM NaHCO3, 20 mM HEPES in water at pH 7.4; sterile filtered)

DMSO (Sigma)

Bis-benzimide H 33342 trihydrochloride (Hoechst 33342; Sigma-Aldrich)

Reference molecule (agonist): Torin-1, (#4247, Tocris) stock 1.2 mM in DMSO, stored at −20° C.

Reporter of Autophagy and Cell line

Reporter Rosella: a fluorescent-based chimera constitutes by two fluorescent proteins, Green and Red variants, acting as a bimodal indicator of pH. The green fluorescent variant of the constructs is pH sensitive (pKa=6.9) while the red variant is not pH sensitive and it is used as reference. The reporter is fused to sequence for autophagosome localization (LC3 tag).

The reporter Rosella have been stably expressed in HeK293 cell line and used as read-out.

Assay Protocol

Experiments have been performed in 384 MTP polylysine coated well format. Cells have been seeded in 384-w at a density of 6000 cells/well in 25 μl/well complete growth medium without antibiotics. Twenty-four hours later, cells have been treated with compounds and incubated for further 18 hours. Then the cells have been imaged and assayed for the response to various compounds using the reporter for autophagy expressed in the cells as readout.

The experiments were performed in a 384-well format according to the following procedure:

24 h after seeding, cells were incubated with compounds at the desired concentration, and with the reference molecule (agonist) Torin-1 at a top concentration of 1 μM (max signal), for 18 hours at 37° C. and 5% CO2. The final percentage of DMSO was 0.3% in all the conditions.

Then the culture medium was carefully removed to avoid cells detachment and to discard red phenol into the medium and that can interfere with the measurements.

Staining of the nuclei was obtained by incubating the cells with 8 μM/well of Hoechst 3342 in standard Tyrode's buffer for 20 min at RT Then the cells were carefully washed two times with standard Tyrode's buffer Finally, the samples were acquired by recording three fluorescence emission channels (green, red and blue) at 20× magnification and with at least 3-4 fields of view per well in an Operetta CLS microscope (PerkinElmer).

Image analysis was performed by using Harmony software (PerkinElmer). The image analysis involved the following steps: flat-field illumination correction, nuclei segmentation, cell segmentations and identification of vesicles/granules within the cytosol compartments and representing the autophagy vesicles. Measurements of signal intensity ratio (Green to Red) and number of autophagy vesicles per cells were used to obtain information on the effects of compounds on the autophagy flux.

Data from image analysis measurements were finally loaded and analyzed for normalization and fitting procedures in Genedata Screener© software.

TABLE 3

Activity of TRPML1 agonists

| Example | hTRPML1 FLIPR $pEC_{50}$ | Autophagy $pEC_{50}$ |
|---|---|---|
| 1 | B | A |
| 2 | B | A |
| 3 | C | |
| 4 | B | |
| 5 | C | |
| 6 | C | C |
| 7 | B | |
| 8 | A | A |
| 9 | C | |
| 10 | B | B |
| 11 | C | |
| 12 | C | |
| 13 | B | |
| 14 | A | |
| 15 | B | |
| 16 | B | |
| 17 | B | A |
| 18 | C | |
| 19 | B | C |
| 20 | C | |
| 21 | C | |
| 22 | B | C |
| 23 | B | C |
| 24 | B | |
| 25 | B | B |
| 26 | B | |
| 27 | B | |
| 28 | B | A |
| 29 | C | |
| 30 | B | |
| 31 | C | C |
| 32 | C | B |
| 33 | C | A |
| 34 | B | B |
| 35 | B | |
| 36 | B | |
| 37 | A | |
| 38 | B | A |
| 39 | C | |
| 40 | C | A |
| 41 | C | |
| 42 | C | |
| 43 | A | |
| 44 | A | |
| 45 | A | |

A > 6.0

B = 6.0-5.5

C < 5.5

What is claimed is:

1. A compound of Formula (II), or a pharmaceutically acceptable salt, solvate, or stereoisomer thereof:

Formula (II)

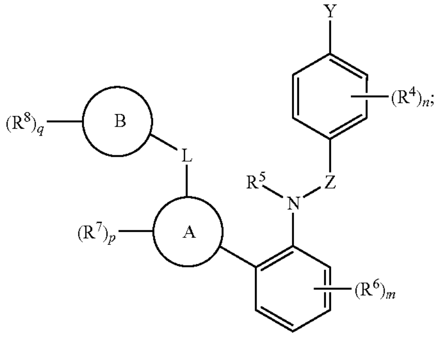

wherein:

Y is $—S(=O)_2NR^1R^2$ or $—S(=O)_2R^3$;

$R^1$ and $R^2$ are independently hydrogen or $C_1$-$C_6$alkyl;

$R^3$ is $C_1$-$C_6$alkyl;

each $R^4$ is independently deuterium, halogen, —CN, —OH, $—OR^a$, $—NR^cR^d$, $—C(=O)R^a$, $—C(=O)OR^b$, $—C(—O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —C(=O)— or $—S(=O)_2—$;

$R^5$ is hydrogen or $C_1$-$C_6$alkyl;

each $R^6$ is independently deuterium, halogen, —CN, —OH, $—OR^a$, $—NR^cR^d$, $—C(=O)R^a$, $—C(=O)OR^b$, $—C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 1-4;

Ring A is heterocycloalkyl;

each $R^7$ is independently deuterium, halogen, —CN, $—NO_2$, —OH, $—OR^a$, $—NR^cR^d$, $—C(=O)R^a$, $—C(=O)OR^b$, $—C(—O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

p is 0-4;

L is absent or —O—;

Ring B is aryl or heteroaryl;

each $R^8$ is independently deuterium, halogen, —CN, $—NO_2$, —OH, $—OR^a$, $—NR^cR^d$, $—C(=O)R^a$, $—C(=O)OR^b$, $—C(—O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

q is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, $—OCH_3$, $—S(=O)CH_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(═O)CH$_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(═O)CH$_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(═O)CH$_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

2. The compound of claim 1, or a pharmaceutically acceptable salt, solvate, or stereoisomer thereof, wherein:

each $R^6$ is independently halogen or $C_1$-$C_6$alkyl and m is 1 or 2.

3. The compound of claim 1, or a pharmaceutically acceptable salt, solvate, or stereoisomer thereof, wherein:

Ring A is a 6-membered heterocycloalkyl.

4. The compound of claim 1, or a pharmaceutically acceptable salt, solvate, or stereoisomer thereof, wherein:

each $R^7$ is independently $C_1$-$C_6$alkyl, $C_1$-$C_6$haloalkyl, or $C_1$-$C_6$deuteroalkyl and p is 0 or 1.

5. The compound of claim 1, or a pharmaceutically acceptable salt, solvate, or stereoisomer thereof, wherein:

Ring B is phenyl or pyridinyl.

6. The compound of claim 1, or a pharmaceutically acceptable salt, solvate, or stereoisomer thereof, wherein:

each $R^8$ is independently deuterium, halogen, $C_1$-$C_6$alkyl, $C_1$-$C_6$haloalkyl, or $C_1$-$C_6$deuteroalkyl and q is 1 or 2.

7. A compound of Formula (III), or a pharmaceutically acceptable salt, solvate, or stereoisomer thereof:

Formula (III)

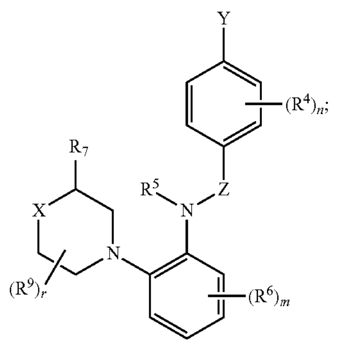

wherein:

Y is —S(═O)$_2$NR$^1$R$^2$;

$R^1$ and $R^2$ are independently hydrogen or $C_1$-$C_6$alkyl;

each $R^4$ is independently deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

Z is —C(═O)— or —S(═O)$_2$—;

$R^5$ is hydrogen or $C_1$-$C_6$alkyl;

each $R^6$ is independently deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-4;

X is —O— or —C(R$^9$)$_2$—;

$R^7$ is —W—OR$^{10}$, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, heterocycloalkyl, $C_1$-$C_6$alkyl(cycloalkyl), or $C_1$-$C_6$alkyl(heterocycloalkyl);

W is absent or $C_1$-$C_3$alkylene;

$R^{10}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^9$ is independently hydrogen, deuterium, halogen, —CN, —NO$_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

r is 0-6;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(—O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(—O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

8. The compound of claim 7, or a pharmaceutically acceptable salt, solvate, or stereoisomer thereof, wherein:

Z is —S(=O)$_2$—.

9. The compound of claim 7, or a pharmaceutically acceptable salt, solvate, or stereoisomer thereof, wherein:

each $R^6$ is independently deuterium, halogen, $C_1$-$C_6$alkyl, $C_1$-$C_6$haloalkyl, or $C_1$-$C_6$deuteroalkyl and m is 0 or 1.

10. The compound of claim 7, or a pharmaceutically acceptable salt, solvate, or stereoisomer thereof, wherein:

$R^7$ is —W—$OR^{10}$, $C_2$-$C_6$alkynyl, or cycloalkyl and W is absent or $C_1$ alkylene.

11. The compound of claim 7, or a pharmaceutically acceptable salt, solvate, or stereoisomer thereof, wherein:

$R^{10}$ is aryl or $C_1$-$C_6$alkyl(aryl).

12. The compound of claim 7, or a pharmaceutically acceptable salt, solvate, or stereoisomer thereof, wherein:

$R^7$ is $C_2$-$C_6$alkynyl or cycloalkyl.

13. The compound of claim 7, or a pharmaceutically acceptable salt, solvate, or stereoisomer thereof, wherein:

each $R^9$ is independently hydrogen, deuterium, halogen, $C_1$-$C_6$alkyl, $C_1$-$C_6$haloalkyl, or $C_1$-$C_6$deuteroalkyl and r is 0 or 1.

14. A compound of Formula (IV), or a pharmaceutically acceptable salt, solvate, or stereoisomer thereof:

Formula (IV)

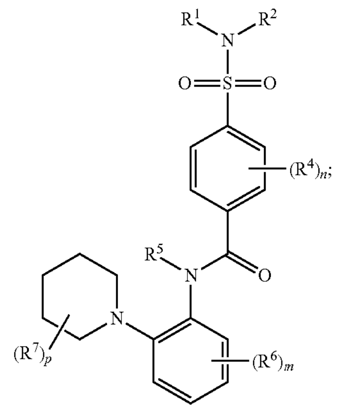

wherein:

$R^1$ and $R^2$ are independently hydrogen or $C_1$-$C_6$alkyl;

each $R^4$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

n is 0-4;

$R^5$ is $C_2$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^6$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

m is 0-4;

each $R^7$ is independently deuterium, halogen, —CN, —$NO_2$, —OH, —$OR^{10}$, —OC(=O)$R^{10}$, —OC(=O)$OR^{11}$, —OC(=O)$NR^{12}R^{13}$, —SH, —$SR^{10}$, —S(=O)$R^{10}$, —S(=O)$_2R^{10}$, —S(=O)$_2NR^{12}R^{13}$, —$NR^{12}R^{13}$, —$NR^{11}$C(=O)$NR^{12}R^{13}$, —$NR^{11}$C(=O)$R^{10}$, —$NR^{11}$C(=O)$OR^{11}$, —$NR^{11}$S(=O)$_2R^{10}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{7a}$;

each $R^{7a}$ is independently deuterium, halogen, —CN, —$NO_2$, —OH, —$OR^a$, —OC(═O)$R^a$, —OC(═O)$OR^b$, —OC(═O)$NR^cR^d$, —$NR^cR^d$, —$NR^b$C(═O)$NR^cR^d$, —$NR^b$C(═O)$R^a$, —$NR^b$C(═O)$OR^b$, —$NR^b$S(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{7a}$ on the same atom are taken together to form an oxo;

p is 0-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(—O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; and each $R^{12}$ and $R^{13}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or $R^{12}$ and $R^{13}$ are taken together with the atom to which they are attached to form a heterocycloalkyl optionally substituted with one or more deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(═O)$CH_3$, —S(═O)$_2CH_3$, —S(═O)$_2NH_2$, —S(—O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

15. The compound of claim 14, or a pharmaceutically acceptable salt, solvate, or stereoisomer thereof, wherein:

$R^5$ is $C_2$-$C_6$alkyl, $C_1$-$C_6$ heteroalkyl, or cycloalkyl.

16. The compound of claim 14, or a pharmaceutically acceptable salt, solvate, or stereoisomer thereof, wherein:

each $R^6$ is independently deuterium, halogen, $C_1$-$C_6$alkyl, $C_1$-$C_6$haloalkyl, or $C_1$-$C_6$deuteroalkyl and m is 0 or 1.

17. The compound of claim 14, or a pharmaceutically acceptable salt, solvate, or stereoisomer thereof, wherein:

each $R^7$ is independently-$OR^{10}$, $C_1$-$C_6$alkyl, $C_1$-$C_6$haloalkyl, $C_1$-$C_6$deuteroalkyl, aryl, or heteroaryl; wherein the alkyl, aryl, and heteroaryl is optionally and independently substituted with one or more $R^{7a}$ and p is 1 or 2.

18. A compound selected from the group consisting of:

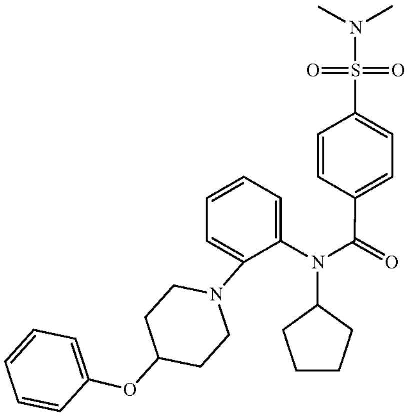 [SMILES: CN(C)S(=O)(=O)c1ccc(C(=O)N(c2ccccc2N2CCC(Oc3ccccc3)CC2)C2CCCC2)cc1]

N-cyclopentyl-4-(N,N-dimethylsulfamoyl)-N-(2-(4-phenoxypiperidin-1-yl)phenyl)benzamide

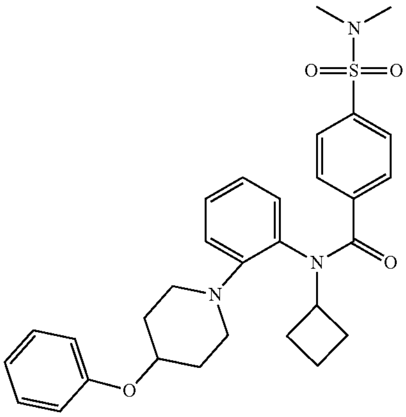 [SMILES: CN(C)S(=O)(=O)c1ccc(C(=O)N(c2ccccc2N2CCC(Oc3ccccc3)CC2)C2CCC2)cc1]

N-cyclobutyl-4-(N,N-dimethylsulfamoyl)-N-(2-(4-phenoxypiperidin-1-yl)phenyl)benzamide

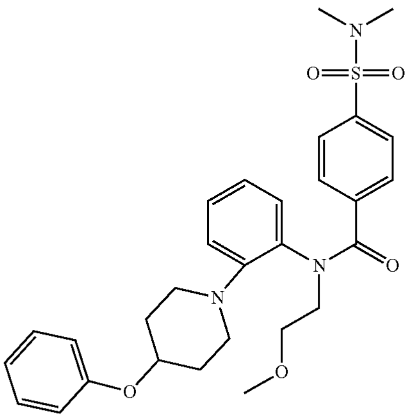 [SMILES: COCCN(C(=O)c1ccc(S(=O)(=O)N(C)C)cc1)c1ccccc1N1CCC(Oc2ccccc2)CC1]

4-(N,N-dimethylsulfamoyl)-N-(2-methoxyethyl)-N-(2-(4-phenoxypiperidin-1-yl)phenyl)benzamide -continued
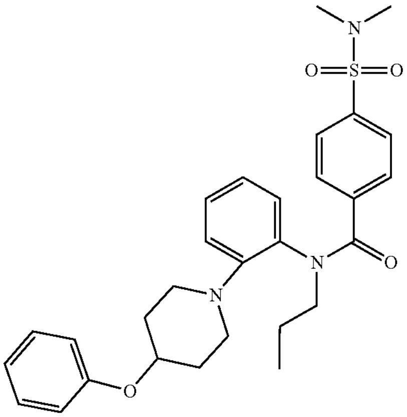 [SMILES: CCCN(C(=O)c1ccc(S(=O)(=O)N(C)C)cc1)c1ccccc1N1CCC(Oc2ccccc2)CC1]
4-(N,N-dimethylsulfamoyl)-N-(2-(4-phenoxypiperidin-1-yl)phenyl)-N-propylbenzamide
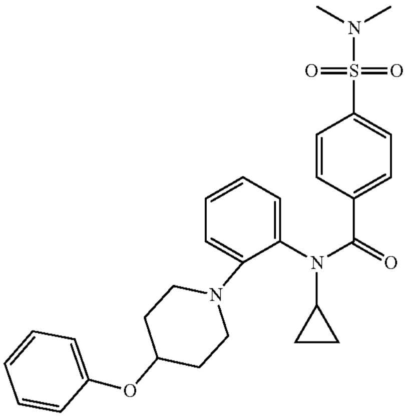 [SMILES: CN(C)S(=O)(=O)c1ccc(C(=O)N(c2ccccc2N2CCC(Oc3ccccc3)CC2)C2CC2)cc1]
N-cyclopropyl-4-(N,N-dimethylsulfamoyl)-N-(2-(4-phenoxypiperidin-1-yl)phenyl)benzamide
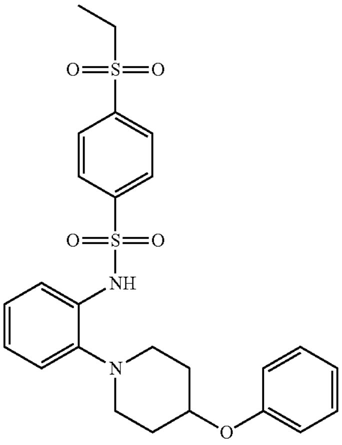 [SMILES: CCS(=O)(=O)c1ccc(S(=O)(=O)Nc2ccccc2N2CCC(Oc3ccccc3)CC2)cc1]
4-(ethylsulfonyl)-N-(2-(4-phenoxypiperidin-1-yl)phenyl)benzenesulfonamide -continued
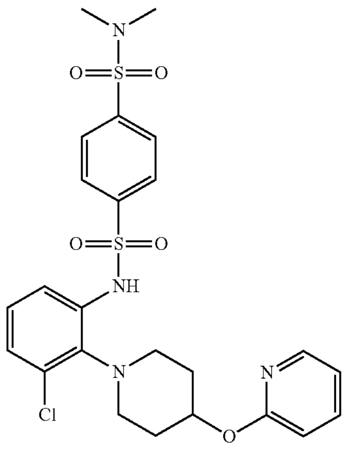 [SMILES: CN(C)S(=O)(=O)c1ccc(S(=O)(=O)Nc2cccc(Cl)c2N2CCC(Oc3ccccn3)CC2)cc1]
N[1]-(3-chloro-2-(4-(pyridin-2-yloxy )piperidin-1-yl)phenyl)-N[4],N[4]-dimethylbenzene-1,4-disulfonamide
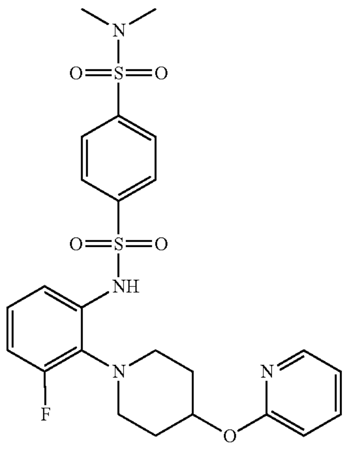
N[1]-(3-fluoro-2-(4-(pyridin-2-yloxy) piperidin-1-yl)phenyl)-N[4],N[4]-dimethylbenzene-1,4-disulfonamide
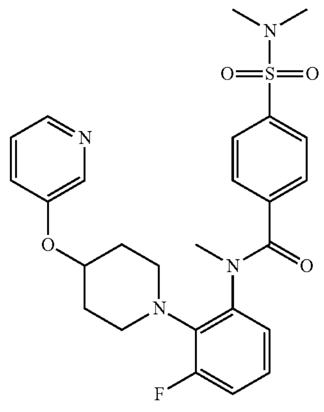 [SMILES: CN(C(=O)c1ccc(S(=O)(=O)N(C)C)cc1)c1cccc(F)c1N1CCC(Oc2cccnc2)CC1]
4-(N,N-dimethylsulfamoyl)-N-(3-fluoro-2-(4-(pyridin-2-yloxy)piperidin-1-yl)phenyl)-N-methylbenzamide -continued
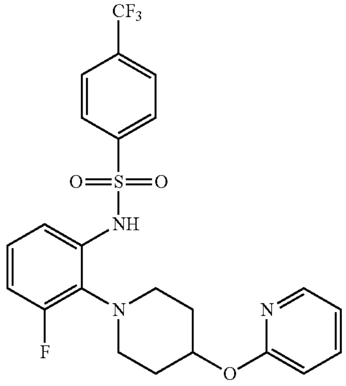 [SMILES: O=S(=O)(Nc1cccc(F)c1N1CCC(Oc2ccccn2)CC1)c1ccc(C(F)(F)F)cc1]
N-(3-fluoro-2-(4-(pyridin-2-yloxy)piperidin-1-yl)phenyl)-4-(trifluoromethyl)benzenesulfonamide
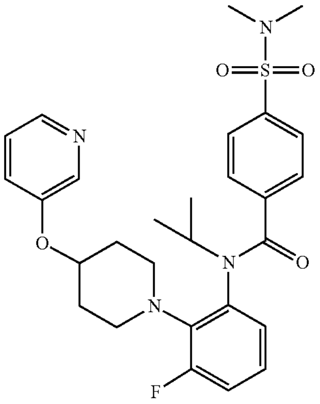 [SMILES: CC(C)N(C(=O)c1ccc(S(=O)(=O)N(C)C)cc1)c1cccc(F)c1N1CCC(Oc2cccnc2)CC1]
4-(N,N-dimethylsulfamoyl)-N-(3-fluoro-2-(4-(pyridin-2-yloxy)piperidin-1-yl)phenyl)-N-isopropylbenzamide
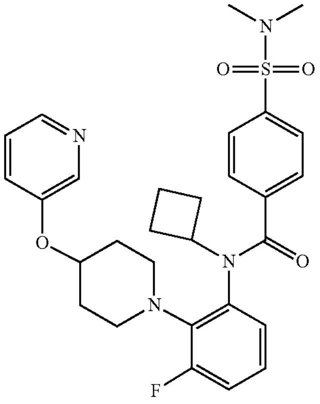 [SMILES: CN(C)S(=O)(=O)c1ccc(C(=O)N(c2cccc(F)c2N2CCC(Oc3cccnc3)CC2)C2CCC2)cc1]
N-cyclobutyl-4-(N,N-dimethylsulfamoyl)-N-(3-fluoro-2-(4-(pyridin-2-yloxy)piperidin-1-yl)phenyl)benzamide
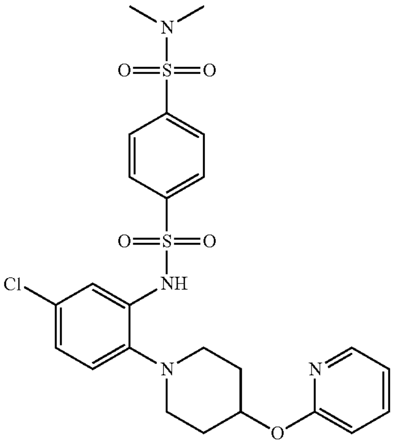 [SMILES: CN(C)S(=O)(=O)c1ccc(S(=O)(=O)Nc2cc(Cl)ccc2N2CCC(Oc3ccccn3)CC2)cc1]
$N^1$-(5-chloro-2-(4-(pyridin-2-yloxy) piperidin-1-yl)phenyl)-N4,N4-dimethylbenzene-1,4-disulfonamide -continued
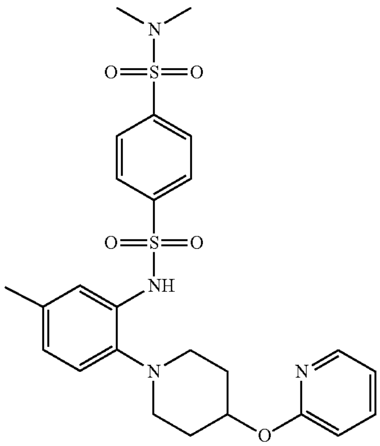 [SMILES: Cc1ccc(N2CCC(Oc3ccccn3)CC2)c(NS(=O)(=O)c2ccc(S(=O)(=O)N(C)C)cc2)c1]
N[1], N[1]-dimethyl-N4-(5-methyl-2-(4-(pyridin-2-yloxy)piperidin-1-yl)phenyl)benzene-1,4-disulfonamide
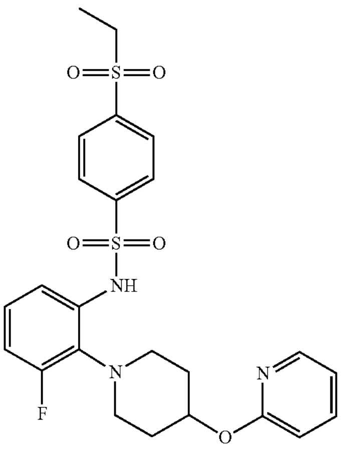 [SMILES: CCS(=O)(=O)c1ccc(S(=O)(=O)Nc2cccc(F)c2N2CCC(Oc3ccccn3)CC2)cc1]
4-(ethylsulfonyl)-N-(3-fluoro-2-(4-(pyridin-2-yloxy)piperidin-1 -yl)phenyl)benzenesulfonamide
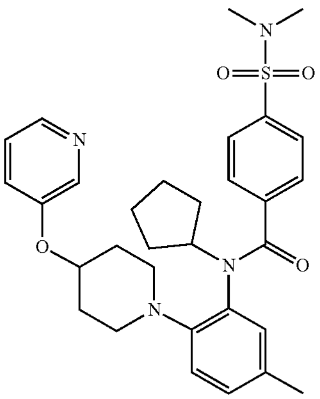 [SMILES: Cc1ccc(N2CCC(Oc3cccnc3)CC2)c(N(C(=O)c2ccc(S(=O)(=O)N(C)C)cc2)C2CCCC2)c1]
N-cyclopentyl-4-(N,N-dimethylsulfamoyl)-N-(5-methyl-2-(4-(pyridin-2-yloxy)piperidin-1-yl)phenyl)benzamide -continued
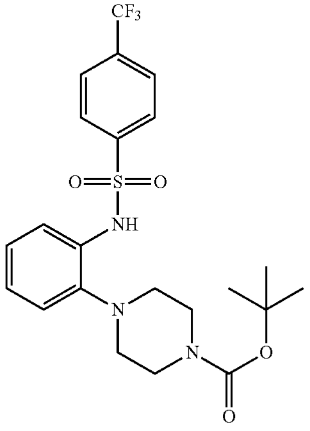 [SMILES: CC(C)(C)OC(=O)N1CCN(c2ccccc2NS(=O)(=O)c2ccc(C(F)(F)F)cc2)CC1]
tert-butyl 4-(2-((4-(trifluoromethyl)phenyl)sulfonamido)phenyl)piperazine-1-carboxylate
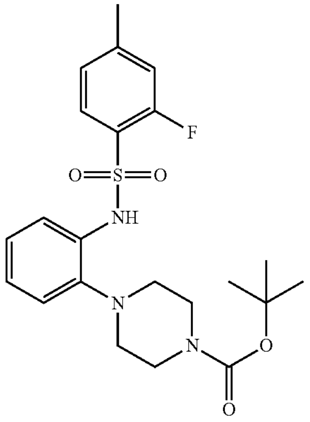 [SMILES: Cc1ccc(S(=O)(=O)Nc2ccccc2N2CCN(C(=O)OC(C)(C)C)CC2)c(F)c1]
tert-butyl 4-(2-((2-fluoro-4-methylphenyl)sulfonamido)phenyl)piperazine-1-carboxylate
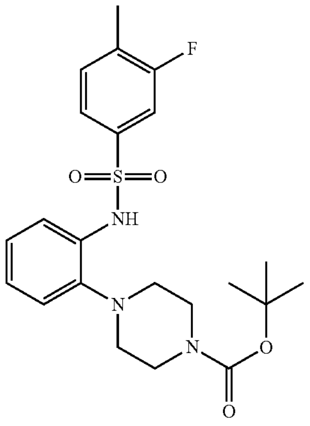 [SMILES: Cc1ccc(S(=O)(=O)Nc2ccccc2N2CCN(C(=O)OC(C)(C)C)CC2)cc1F]
tert-butyl 4-(2-((3-fluoro-4-methylphenyl)sulfonamido)phenyl)piperazine-1-carboxylate -continued
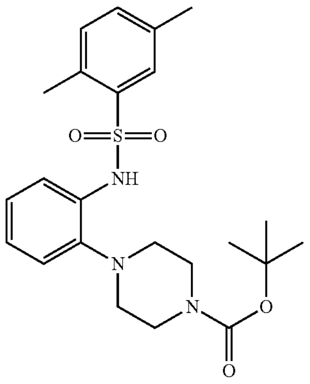 [SMILES: Cc1ccc(C)c(S(=O)(=O)Nc2ccccc2N2CCN(C(=O)OC(C)(C)C)CC2)c1]
tert-butyl 4-(2-((2,5-dimethylphenyl)sulfonamido)phenyl) piperazine-1-carboxylate
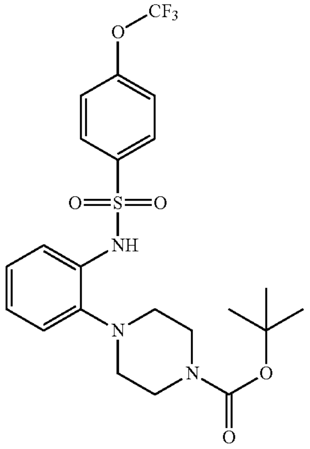 [SMILES: CC(C)(C)OC(=O)N1CCN(c2ccccc2NS(=O)(=O)c2ccc(OC(F)(F)F)cc2)CC1]
tert-butyl 4-(2-((4-(trifluoromethoxy)phenyl)sulfonamido) phenyl)piperazine-1-carboxylate
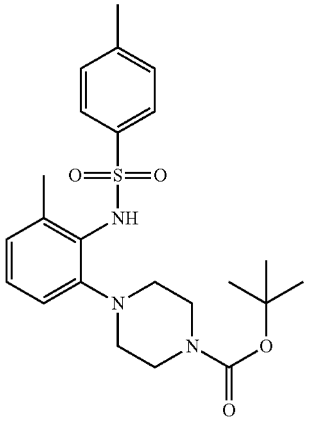 [SMILES: Cc1ccc(S(=O)(=O)Nc2c(C)cccc2N2CCN(C(=O)OC(C)(C)C)CC2)cc1]
tert-butyl 4-(3-methyl-2-((4-methylphenyl)sulfonamido)phenyl) piperazine-1-carboxylate -continued
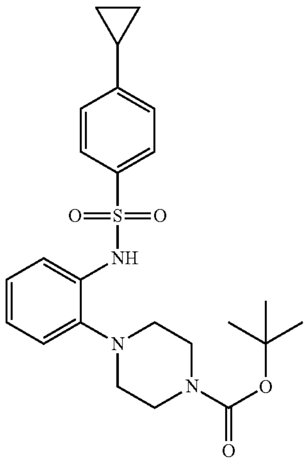 [SMILES: CC(C)(C)OC(=O)N1CCN(c2ccccc2NS(=O)(=O)c2ccc(C3CC3)cc2)CC1]
tert-butyl 4-(2-((4-cyclopropylphenyl)sulfonamido)phenyl) piperazine-1-carboxylate
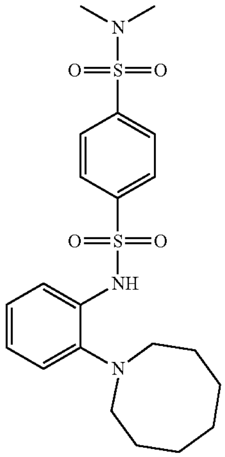 [SMILES: CN(C)S(=O)(=O)c1ccc(S(=O)(=O)Nc2ccccc2N2CCCCCCC2)cc1]
N1-(2-(azocan-1-yl)phenyl)-N4,N4-dimethylbenzene-1,4-disulfonamide
$N^1$-(2-(3-(benzyloxy)piperidin-1 -yl)phenyl)-$N^4$,$N^4$-dimethylbenzene-1,4-disulfonamide
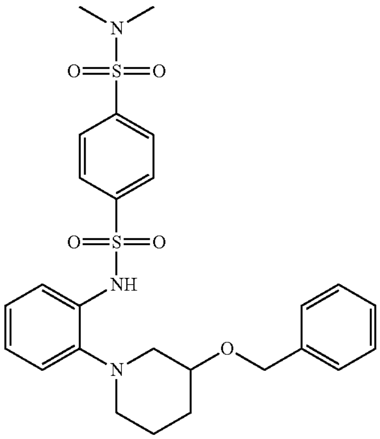 [SMILES: CN(C)S(=O)(=O)c1ccc(S(=O)(=O)Nc2ccccc2N2CCCC(OCc3ccccc3)C2)cc1]

-continued
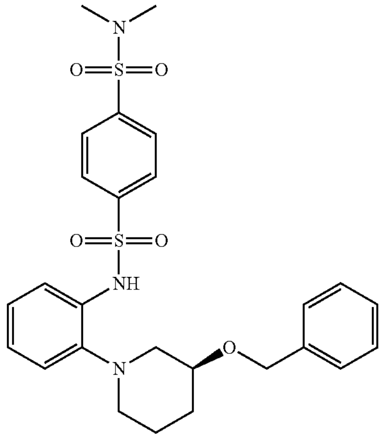 [SMILES: CN(C)S(=O)(=O)c1ccc(S(=O)(=O)Nc2ccccc2N2CCC[C@H](OCc3ccccc3)C2)cc1]
(S)-$N^1$-(2-(3-(benzyloxy)piperidin-1-yl)phenyl)-$N^4$,$N^4$-dimethylbenzene-1,4-disulfonamide
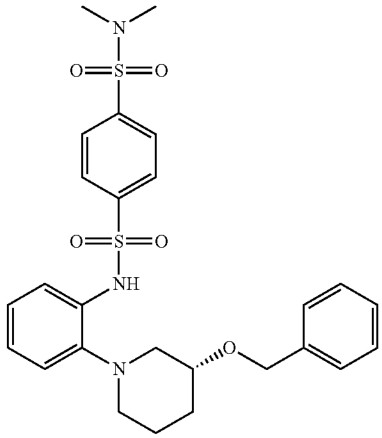 [SMILES: CN(C)S(=O)(=O)c1ccc(S(=O)(=O)Nc2ccccc2N2CCC[C@@H](OCc3ccccc3)C2)cc1]
(R)-$N^1$-(2-(3-(benzyloxy)piperidin-1-yl)phenyl)-$N^4$,$N^4$-dimethylbenzene-1,4-disulfonamide
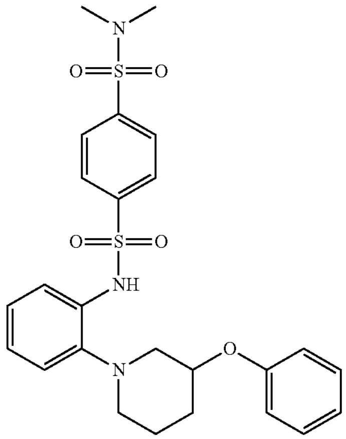 [SMILES: CN(C)S(=O)(=O)c1ccc(S(=O)(=O)Nc2ccccc2N2CCCC(Oc3ccccc3)C2)cc1]
$N^1$,$N^1$-dimethyl-$N^4$-(2-(3-phenoxypiperidin-1-yl)phenyl)benzene-1,4-disulfonamide -continued
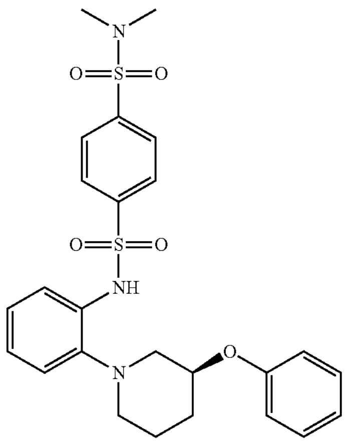 [SMILES: CN(C)S(=O)(=O)c1ccc(S(=O)(=O)Nc2ccccc2N2CCC[C@H](Oc3ccccc3)C2)cc1]
(S)-N$^1$,N$^1$-dimethyl-N$^4$-(2-(3-phenoxypiperidin-1-yl)phenyl)benzene-1,4-disulfonamide
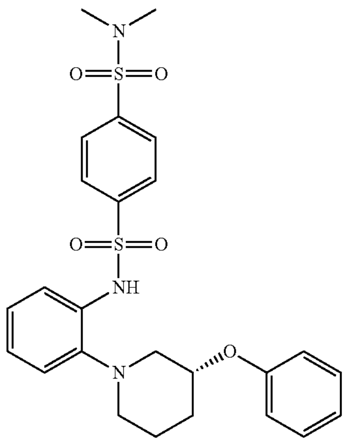 [SMILES: CN(C)S(=O)(=O)c1ccc(S(=O)(=O)Nc2ccccc2N2CCC[C@@H](Oc3ccccc3)C2)cc1]
(R)-N$^1$,N$^1$-dimethyl-N$^4$-(2-(3-phenoxypiperidin-1-yl)phenyl)benzene-1,4-disulfonamide
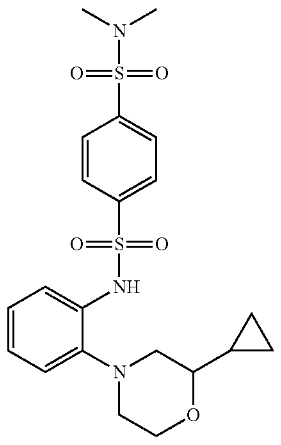 [SMILES: CN(C)S(=O)(=O)c1ccc(S(=O)(=O)Nc2ccccc2N2CCOC(C3CC3)C2)cc1]
N$^1$-(2-(2-cyclopropylmorpholino)phenyl)-N$^4$, N$^4$-dimethylbenzene-1,4-disulfonamide -continued
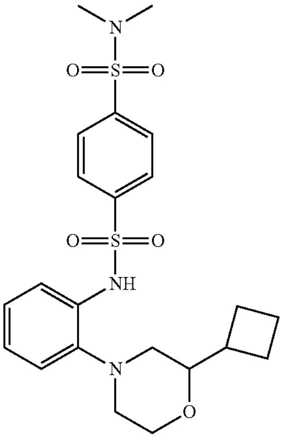 [SMILES: CN(C)S(=O)(=O)c1ccc(S(=O)(=O)Nc2ccccc2N2CCOC(C3CCC3)C2)cc1]
N[1]-(2-(2-cyclobutylmorpholino)phenyl)-N[4],N[4]-dimethylbenzene-1,4-disulfonamide
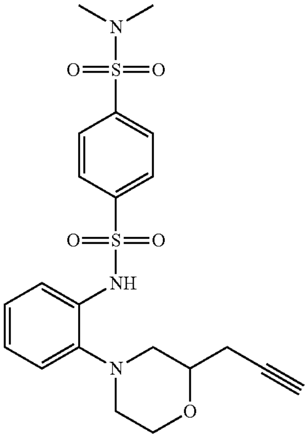 [SMILES: C#CCC1CN(c2ccccc2NS(=O)(=O)c2ccc(S(=O)(=O)N(C)C)cc2)CCO1]
N[1], N[1]-dimethyl-N[4]-(2-(2-(prop-2-yn-1-yl)morpholino)phenyl)benzene-1,4-disulfonamide
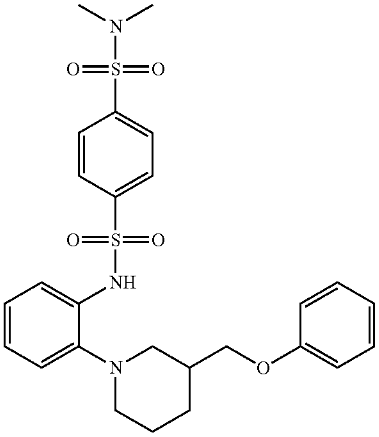 [SMILES: CN(C)S(=O)(=O)c1ccc(S(=O)(=O)Nc2ccccc2N2CCCC(COc3ccccc3)C2)cc1]
N[1],N[1]-dimethyl-N[4]-(2-(3-(phenoxymethyl)piperidin-1-yl)phenyl)benzene-1,4-disulfonamide -continued
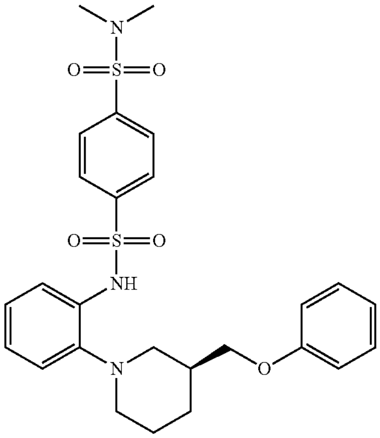 [SMILES: CN(C)S(=O)(=O)c1ccc(S(=O)(=O)Nc2ccccc2N2CCC[C@H](COc3ccccc3)C2)cc1]
(S)-$N^1$, $N^1$-dimethyl-$N^4$-(2-(3-(phenoxymethyl)piperidin-1-yl)phenyl)benzene-1,4-disulfonamide
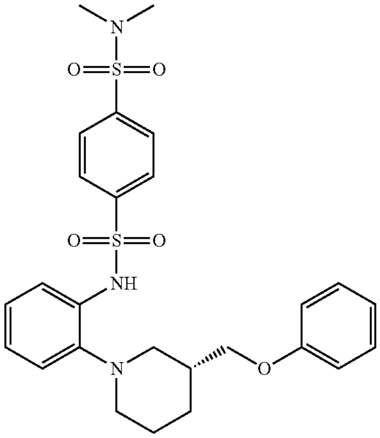
(R)-$N^1$, $N^1$-dimethyl-$N_4$-(2-(3-(phenoxymethyl) piperidin-1-yl)phenyl)benzene-1,4-disulfonamide
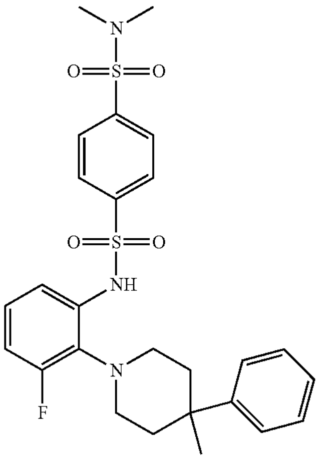 [SMILES: CN(C)S(=O)(=O)c1ccc(S(=O)(=O)Nc2cccc(F)c2N2CCC(C)(c3ccccc3)CC2)cc1]
$N^1$-(3-fluoro-2-(4-methyl-4-phenylpiperidin-1-yl)phenyl)-$N^4$,$N^4$-dimethylbenzene-1,4 disulfonamide -continued
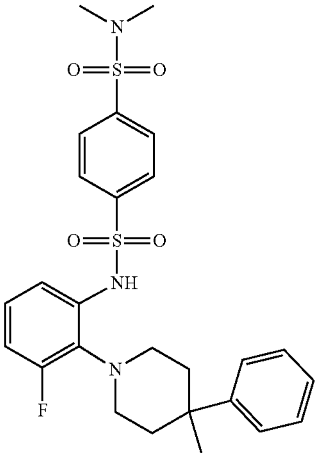 [SMILES: CN(C)S(=O)(=O)c1ccc(S(=O)(=O)Nc2cccc(F)c2N2CCC(C)(c3ccccc3)CC2)cc1]
N[1], N[1]-dimethyl-N4-(2-(4-methyl-4-phenylpiperidin-1-yl)phenyl)benzene-1,4-disulfonamide
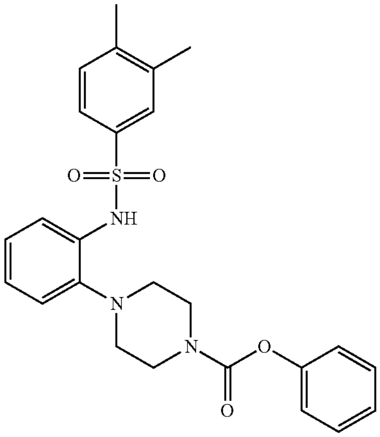 [SMILES: Cc1ccc(S(=O)(=O)Nc2ccccc2N2CCN(C(=O)Oc3ccccc3)CC2)cc1C]
phenyl 4-(2-((3,4-dimethylphenyl)sulfonamido)phenyl) piperazine-1-carboxylate
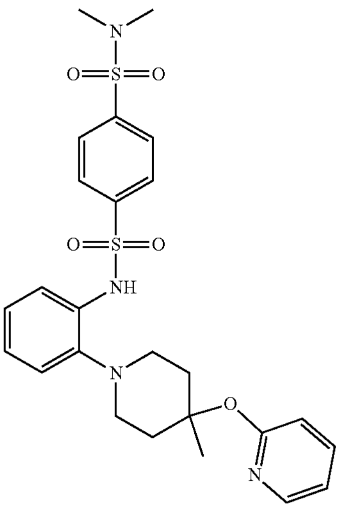 [SMILES: CN(C)S(=O)(=O)c1ccc(S(=O)(=O)Nc2ccccc2N2CCC(C)(Oc3ccccn3)CC2)cc1]
N[1],N[1]-dimethyl-N[4]-(2-(4-methyl-4-(pyridin-2-yloxy)piperidin-1-yl)phenyl)benzene-1,4-disulfonamide -continued
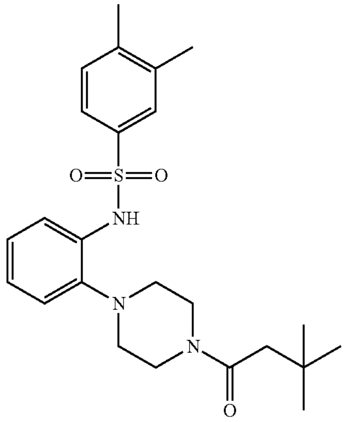 [SMILES: Cc1ccc(S(=O)(=O)Nc2ccccc2N2CCN(C(=O)CC(C)(C)C)CC2)cc1C]
N-(2-(4-(3,3-dimethylbutanoyl)piperazin-1-yl)phenyl)-3,4-dimethylbenzenesulfonamide
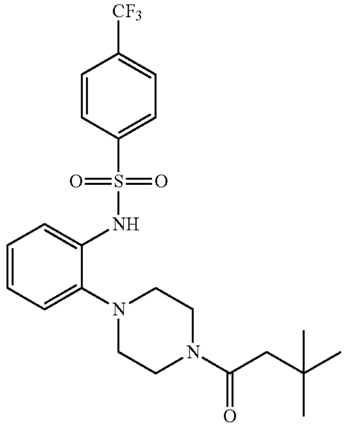 [SMILES: CC(C)(C)CC(=O)N1CCN(c2ccccc2NS(=O)(=O)c2ccc(C(F)(F)F)cc2)CC1]
N-(2-(4-(3,3-dimethylbutanoyl)piperazin-1-yl)phenyl)-4-(trifluoromethyl)benzenesulfonamide
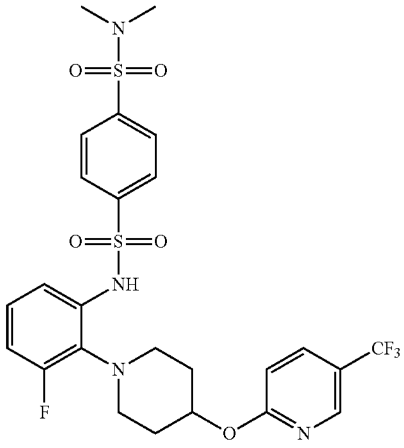 [SMILES: CN(C)S(=O)(=O)c1ccc(S(=O)(=O)Nc2cccc(F)c2N2CCC(Oc3ccc(C(F)(F)F)cn3)CC2)cc1]
$N^1$-(3-fluoro-2-(4-((5-(trifluoromethyl)pyridin-2-yl)oxy)piperidin-1-yl)phenyl)-$N^4$,$N^4$-dimethylbenzene-1,4-disulfonamide -continued

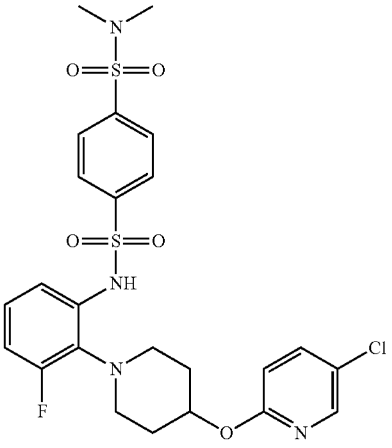 [SMILES: CN(C)S(=O)(=O)c1ccc(S(=O)(=O)Nc2cccc(F)c2N2CCC(Oc3ccc(Cl)cn3)CC2)cc1]

$N^1$-(2-(4-((5-chloropyridin-2-yl)oxy)piperidin-1-yl)-3-fluorophenyl)-$N^4$,$N^4$-dimethylbenzene-1,4-disulfonamide

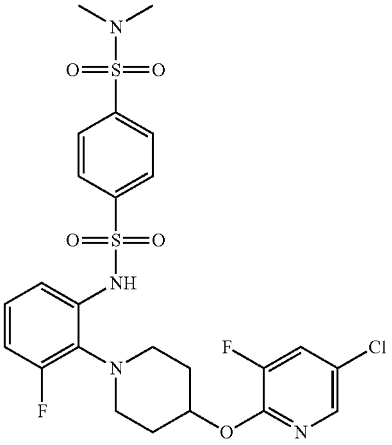 [SMILES: CN(C)S(=O)(=O)c1ccc(S(=O)(=O)Nc2cccc(F)c2N2CCC(Oc3ncc(Cl)cc3F)CC2)cc1]

$N^1$-(2-(4-((5-chloro-3-fluoropyridin-2-yl)oxy)piperidin-1-yl)-3-fluorophenyl)-$N^4$,$N^4$-dimethylbenzene-1,4-disulfonamide or a pharmaceutically acceptable salt, solvate, or stereoisomer thereof.

19. A pharmaceutical composition comprising a compound of claim 1, or a pharmaceutically acceptable salt, solvate, or stereoisomer thereof, and a pharmaceutically acceptable excipient.

20. A method of treating a TRPML1-mediated disorder or disease; the method comprising administering a therapeutically effective amount of a compound of claim 1, or a pharmaceutically acceptable salt, solvate, or stereoisomer thereof.

* * * * *